(12) United States Patent
Butzke et al.

(10) Patent No.: US 8,784,813 B2
(45) Date of Patent: Jul. 22, 2014

(54) **L-AMINO ACID OXIDASE WITH CYTOTOXIC ACTIVITY FROM *APLYSIA PUNCTATA***

(75) Inventors: Daniel Butzke, Bonn (DE); Sigrid Goedert, Falkensee (DE); Michael Dittrich, Seesen am Harz (DE); Thomas Rudel, Berlin (DE); Thomas Meyer, Berlin (DE)

(73) Assignee: Thomas Rudel, Würzburg (DE)

( * ) Notice: Subject to any disclaimer, the term of this patent is extended or adjusted under 35 U.S.C. 154(b) by 877 days.

(21) Appl. No.: 12/163,261

(22) Filed: Jun. 27, 2008

(65) Prior Publication Data

US 2009/0028864 A1 Jan. 29, 2009

Related U.S. Application Data

(62) Division of application No. 10/542,769, filed as application No. PCT/EP2004/000423 on Jan. 20, 2004, now Pat. No. 7,407,784.

(30) Foreign Application Priority Data

Jan. 20, 2003 (EP) ..................................... 03001232
Nov. 19, 2003 (EP) ..................................... 03026613

(51) Int. Cl.
  *A61K 39/395* (2006.01)
  *C12P 21/06* (2006.01)
(52) U.S. Cl.
  USPC ........................ 424/139.1; 424/191; 435/69.1
(58) Field of Classification Search
  None
  See application file for complete search history.

(56) References Cited

U.S. PATENT DOCUMENTS

| 6,171,818 B1 | 1/2001 | Petzelt |
| 6,372,211 B1 | 4/2002 | Isaac et al. |
| 7,271,242 B2 * | 9/2007 | Petzelt .......................... 530/350 |
| 2004/0101940 A1 | 5/2004 | Butzke et al. |

FOREIGN PATENT DOCUMENTS

| WO | WO 97/16457 A | 5/1997 |
| WO | WO 02/31144 A | 4/2002 |
| WO | WO 03/057726 A | 7/2003 |

OTHER PUBLICATIONS

Garrett et al European J. of cancer 1999, 35, 2010-2030.*
Petzel et al.; "Cytotoxic Cyplasin of the Sea Hare, *Aplysia punctata*, CDNA Cloning, and Expression of Bioactive Recombinants in Insect Cells"; Neoplasia Doyma, Barcelona, ES, vol. 4, No. 1, Jan. 2002; pp. 49-59, XP008016612; ISSN: 0212-9787.
Yamazaki, "Antitumor and Antimicrobial Glycoproteins from Sea Hares" Comperative Biochemistry and Physiology, Elmsford, NY, US, vol. 105C, No. 2, 1993, pp. 141-146, XP002034987.
Yamazaki et al., "Purification of A Cytolytic Factor From Purple Fluid of a Sea Hare" FEBS Letters, Elsevier Science Publishers, Amsterdam, NL, vol. 198, No. 1, Mar. 1986, pp. 5-28, XP001002735, ISSN: 0014-5793.

* cited by examiner

*Primary Examiner* — Tekchand Saidha
*Assistant Examiner* — Younus Meah
(74) *Attorney, Agent, or Firm* — Michael Fedrick; Loza & Loza, LLP

(57) ABSTRACT

The present invention relates to a cytotoxic polypeptide which is an L-amino acid oxidase isolated from the ink of the sea hare *Aplysia punctata*.

12 Claims, 19 Drawing Sheets

Fig. 4A

Figure 1A:
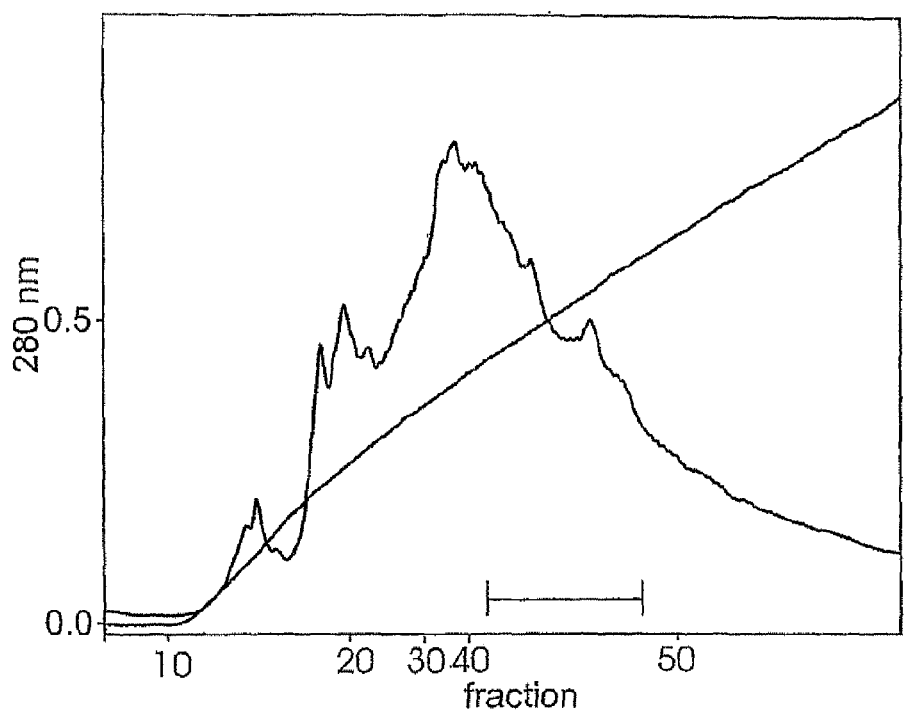
Figure 1B:
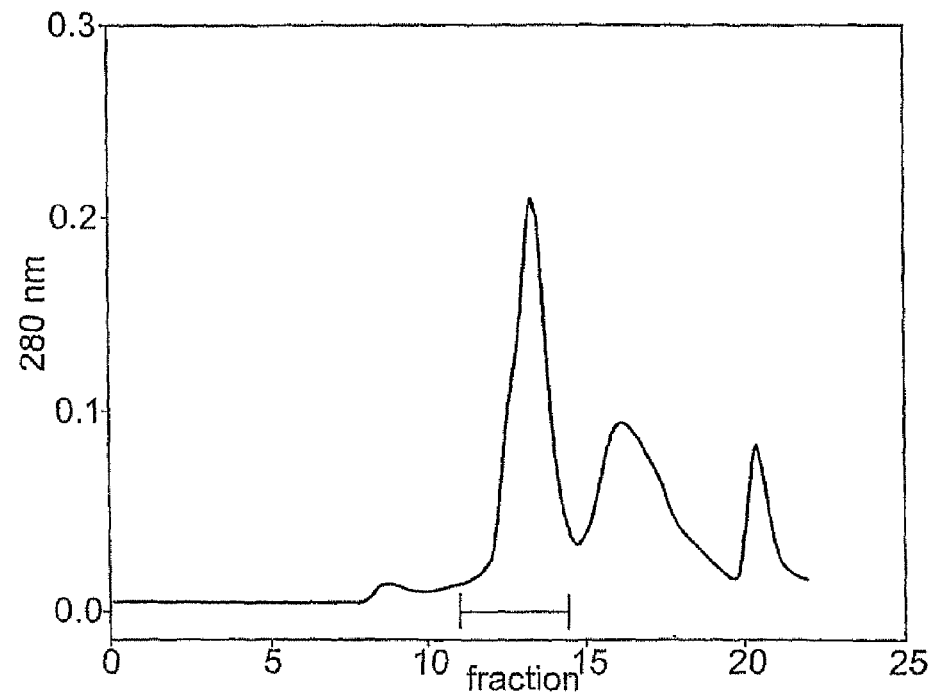

N-terminal sequence:  D-G-I-C-R-N-Q-R-Q
                      Q       V       R   P Internal peptide sequences

| | Sequence |
|---|---|
| 1 | DSGLDIA<u>VFEYSDR</u> |
| 2 | LFXYQLPNTPDVNLEI |
| 3 | VISELGLTPK |
| 4 | XGDVPYDLSPEEK |
| 5 | VILAXPVYALN |
| 6 | ATQAYAAVRPIPASK |
| 7 | VFMTFDQP |
| 8 | SDALFFQMYD |
| 9 | SEASGDYILIASYADGLK |
| 10 | NQGEDIPGSDPQYNQVTEP(L)(K) |

X = not determinable
underlined: primer sequence for RT-PCR

Fig. 4B

| 1 | Oligo-dT DBuTag1 | tcc taa cgt agg tct aga cct gtt gca ttt ttt ttt ttt ttt ttt |
|---|---|---|
| 2 | V-Fey 3 DTS 5' | tc gtg ttc gar tac tci gay cg |
| 3 | DBuTag1 DTS 3' | ctg tag gtc tag acc tgt tgc a |
| 4 | ATF Race 3' 660 | ccg tgt aga tct cac tgc cat a |
| 5 | Abriged Anchor Primer | ggc cac gcg tcg act agt acg ggi igg gii ggg iig |
| 6 | ATF Race 3' 436 | ccg ttg agt tgt aga cct |
| 7 | AUAP-EcoRI | aatt ggc cac gcg tcg act agt ac |
| 8 | ATF 5' Sign Eco RI GEX/ET | aa ttc tcg tct gct gtg ctt ctc ct |
| 9 | ATF 3' XhoI | gac tta gag gaa gta gtc gtt ga |

Fig. 4C

```
         M   S   S   A   V   L   L   L   A   C   A   L   V   I   S   V   H   A   D   G   IV  C
         ATGTCGTCTGCTGTGCTTCTCCTGGCTTGTGCGTTGGTCATCTCTGTCCACGCCGACGGTATCTGC
         ...TCGTCTGCTGTGCTTCTCCTGGCTTGTGCGTTGGTCATCTCTGTCCACGCCGACGGTGTCTGC
         ................................................GACGGTATCTGC

R   N   R   Q   C   N   R   E   V   C   G   S   T   Y   D   V   A   V   V   G   A
         AGAAACAGACGTCAATGTAACAGAGAGGTGTGCGGTTCTACCTACGATGTGGCCGTCGTGGGGGCG
         AGAAACAGACGTCAATGTAACAGAGAGGTGTGCGGTTCTACCTACGATGTGGCCGTCGTGGGGGCG
         AGAAACAGACGTCAATGTAACAGAGAGGTGTGCGGTTCTACCTACGATGTGGCTGTCGTGGGGGCG

G   P   G   G   A   N   S   A   Y   M   L   R   D   S   G   L   D   I   A   V   F   E
         GGGCCTGGGGGAGCTAACTCCGCCTACATGCTGAGGGACTCCGGCCTGGACATCGCTGTGTTCGAG
         GGGCCTGGGGGAGCTAACTCCGCCTACATGCTGAGGGACTCCGGCCTGGACATCGCTGTGTTCGAG
         GGGCCTGGGGGAGCTAACTCCGCCTACATGCTGAGGGACTCCGGCCTGGACATCGCTGTGTTCGAG

Y   S   D   R   V   G   G   R   L   F   T   Y   Q   L   P   N   T   P   D   V   N   L
         TACTCGGACCGAGTGGGCGGCCGGCTGTTCACCTACCAGCTGCCCAACACACCCGACGTTAACCTG
         TACTCAGACCGAGTGGGCGGCCGGCTGTTCACCTACCAGCTGCCCAACACACCCGACGTTAATCTC
         TACTCAGACCGAGTGGGCGGCCGGCTGTTCACCTACCAGCTGCCCAACACACCCGACGTTAATCTC

E   I   G   G   M   R   F   I   E   G   A   M   H   R   L   W   R   V   I   S   E   L
         GAGATTGGCGGCATGAGGTTCATCGAAGGCGCCATGCACAGGCTCTGGAGGGTCATTTCAGAACTC
         GAGATTGGCGGCATGAGGTTCATCGAGGGCGCCATGCACAGGCTCTGGAGGGTCATTTCAGAACTC
         GAGATTGGCGGCATGAGGTTCATCGAGGGCGCCATGCACAGGCTCTGGAGGGTCATTTCAGAACTC

G   L   T   P   K   V   F   K   E   G   F   G   K   E   G   R   Q   R   F   Y   L   R
         GGCCTAACCCCCAAGGTGTTCAAGGAAGGTTTCGGCAAGGAGGGCAGACAAAGATTTTACCTGCGG
         GGCCTAACCCCCAAGGTGTTCAAGGAAGGTTTCGGAAAGGAGGGCAGACAGAGATTTTACCTGCGG
         GGCCTAACCCCCAAGGTGTTCAAGGAAGGTTTCGGAAAGGAGGGCAGACAGAGATTTTACCTGCGG

G   Q   S   L   T   K   K   Q   V   K   S   G   D   V   P   Y   D   L   S   P   E   E
         GGACAGAGCCTGACCAAGAAACAGGTCAAGAGTGGGGACGTACCCTATGACCTCAGCCCGGAGGAG
         GGACAGAGCCTGACCAAGAAACAGGTCAAGAGTGGGGACGTACCCTATGACCTCAGCCCGGAGGAG
         GGACAGAGCCTGACCAAGAAACAGGTCAAGAGTGGGGACGTACCCTATGACCTCAGCCCGGAGGAG

K   E   N   Q   G   N   L   V   E   Y   Y   L   E   K   L   T   G   L   QK  L   N   G
         AAAGAAAACCAGGGAAATCTGGTCGAATACTACCTGGAGAAACTGACAGGTCTACAACTCAACGGC
         AAAGAAAACCAGGGAAATCTGGTCGAATACTACCTGGAGAAACTGACAGGTCTACAACTCAATGGT
         AAAGAAAACCAGGGAAATCTGGTCGAATACTACCTGGAGAAACTGACAGGTCTAAAACTCAACGGC

EG  P   L   K   R   E   V   A   L   K   L   T   V   P   D   G   R   F   L   Y   D   L
         GAGCCGCTCAAACGTGAGGTTGCGCTTAAACTAACCGTGCCGGACGGCAGATTCCTCTATGACCTC
         GAACCGCTCAAACGTGAGGTTGCGCTTAAACTAACCGTGCCGGACGGCAGATTCCTCTATGACCTC
         GGGACCGCTCAAACGTGAGGTTGCGCTTAAACTAACCGTGCCGGACGGCAGATTCCTCTATGACCTC

S   F   D   E   A   M   D   L   V   A   S   P   E   G   K   E   F   T   R   D   T   H
         TCGTTTGACGAAGCCATGGATCTGGTTGCCTCCCCTGAGGGCAAAGAGTTCACCCGAGACACGCAC
         TCGTTTGACGAAGCCATGGATCTGGTTGCCTCCCCTGAGGGCAAAGAGTTCACCCGAGACACGCAC
         TCGTTTGACGAAGCCATGGACCTGGTTGCCTCCCCTGAGGGCAAAGAGTTCACCCGAGACACGCAC
```

Fig. 4C (continued)

```
        V  F  T  G  E  V  T  L  DG A  S  A  V  S  L  F  D  D  H  L  G  E
     GTCTTCACAGGAGAGGTCACCCTGGACGCGTCGGCTGTCTCCCTCTTCGACGACCACCTGGGAGAG
     GTCTTCACCGGAGAGGTCACCCTGGGCGCGTCGGCTGTCTCCCTCTTCGACGACCACCTGGGAGAG
     GTGTTCACCGGAGAAGTCACCCTGGACGCGTCGGCTGTCTCCCTCTTCGACGACCACCTGGGAGAG

D  Y  Y  G  S  E  I  Y  T  L  K  E  G  L  S  S  V  P  Q  G  L  L
     GACTACTATGGCAGTGAGATCTACACCCTAAAGGAAGGACTGTCTTCCGTCCCACAAGGGCTCCTA
     GACTACTACGGCAGTGAGATCTACACCCTCAAGGAAGGACTGTCTTCCGTCCCTCAAGGGCTCCTA
     GACTACTATGGCAGTGAGATCTACACCCTAAAGGAAGGACTGTCTTCCGTCCCACAAGGGCTCCTA

Q  AT F  L  D  A  A  D  S  N  E  F  Y  P  N  S  H  L  K  A  L  R
     CAGGCTTTTCTGGACGCCGCAGACTCCAACGAGTTCTATCCCAACAGCCACCTGAAGGCCCTGAGA
     CAGGCTTTTCTGGACGCCGCAGACTCCAACGAGTTCTATCCCAACAGCCACCTGAAGGCCCTGAGA
     CAGACTTTTCTGGACGCCGCAGACTCCAACGAGTTCTATCCCAACAGCCACCTGAAGGCCCTGAGA

R  K  T  N  G  Q  Y  V  L  Y  F  E  P  T  T  S  K  D  G  Q  T  T
     CGTAAGACCAACGGTCAGTATGTTCTTTACTTTGAGCCCACCACCTCAAGGATGGACAAACCACA
     CGTAAGACCAACGGTCAGTATGTTCTTTACTTTGAGCCCACCACCTCCAAGGATGGACAAACCACA
     CGTAAGACCAACGGTCAGTATGTTCTTTACTTTGAGCCCACCACCTCCAAGGATGGACAAACCACA

I  N  Y  L  E  P  L  Q  V  V  C  A  Q  R  V  I  L  A  M  P  V  Y
     ATCAACTATCTGGAACCCCTGCAGGTTGTGTGTGCACAAAGAGTCATCCTGGCCATGCCGGTATAC
     ATCAACTATCTGGAACCCCTGCAGGTTGTGTGTGCACAGAGAGTCATTCTGGCCATGCCGGTCTAC
     ATCAACTATCTGGAACCCCTGCAGGTTGTGTGTGCACAGAGAGTCATCCTGGCCATGCCGGTCTAC

A  L  N  Q  L  D  W  N  Q  L  R  N  D  R  A  T  Q  A  Y  A  A  V
     GCTCTGAACCAACTAGACTGGAATCAGCTCAGAAATGACCGAGCCACCCAAGCGTACGCTGCCGTT
     GCTCTCAACCAGTTGGATTGGAATCAGCTCAGAAATGACCGAGCCACCCAAGCGTACGCTGCCGTG
     GCTCTCAACCAACTGGACTGGAATCAGCTCAGAAATGACCGAGCCACCCAAGCGTACGCTGCCGTG

R  P  I  P  A  S  K  V  F  M  TS F  D  Q  P  W  W  L  E  N  E  R
     CGCCCGATTCCTGCAAGTAAGGTGTTCATGTCCTTTGATCAGCCCTGGTGGTTGGAGAACGAGAGG
     CGCCCGATTCCTGCAAGTAAGGTGTTCATGACCTTTGATCAGCCCTGGTGGTTGGAGAACGAGAGG
     CGCCCGATTCCTGCAAGTAAAGTGTTCATGACCTTTGATCAGCCCTGGTGGTTGGAGAACGAGAGG

K  S  W  V  T  K  S  D  A  L  F  S  Q  M  Y  D  W  Q  K  S  E  A
     AAATCCTGGGTCACCAAGTCGGACGCGCTTTTCAGCCAAATGTACGACTGGCAGAAGTCTGAGGCG
     AAATCCTGGGTCACCAAGTCGGACGCGCTTTTCAGTCAAATGTACGACTGGCAGAAGTCTGAGGCG
     AAATCCTGGGTCACCAAGTCGGACGCGCTTTTCAGCCAAATGTACGACTGGCAGAAGTCTGAGGCG

S  G  D  Y  I  L  I  A  S  Y  A  D  G  L  K  A  Q  Y  L  R  E  L
     TCCGGAGACTACATCCTGATCGCCAGCTACGCCGACGGCCTCAAAGCCCAGTACCTGCGGGAGCTG
     TCCGGAGACTACATCCTGATCGCCAGCTACGCCGACGGCCTCAAAGCCCAGTACCTGCGGGAGCTG
     TCCGGAGACTACATCCTGATCGCCAGCTACGCCGACGGCCTCAAAGCCCAGTACCTGCGGGAGCTG

K  N  Q  G  E  D  I  P  G  S  D  P  G  Y  N  Q  V  T  E  P  I  K
     AAGAATCAGGGAGAGGACATCCCAGGCTCTGACCCAGGCTACAACCAGGTTACCGAACCCCTCAAG
     AAGAATCAGGGAGAGGACATCCCAGGCTCTGACCCAGGCTACAACCAGGTCACCGAACCCCTCAAG
     AAGAATCAGGGAGAGGACATCCCAGGCTCTGACCCAGGCTACAACCAGGTCACCGAACCCCTCAAG
```

Fig. 4C (continued)

```
       D  T  I  L  D  H  L  T  E  A  Y  G  V  E  R  D  S  I  PR E  P  V
     GACACCATTCTTGACCACCTCACTGAGGCTTATGGCGTGGAGCGAGACTCGATCCCGGAACCCGTG
     GACACCATTCTTGACCACCTCACTGAGGCCTATGGCGTGGAGCGAGACTCGATCCGGGAACCCGTG
     GACACCATTGTTGACCACCTCACTGAGGCTTATGGCGTGGAACGAGACTCGATCCCGGAACCCGTG

T  A  A  S  Q  F  W  T  D  Y  P  F  G  C  W  I  T  W  R  A  G
     ACCGCCGCTTCCCAGTTCTGGACAGACTACCCGTTTGGCTGTGGATGGATCACCTGGAGGGCCGGC
     ACCGCCGCTTCCCAGTTCTGGACAGACTACCCGTTTGGCTGTGGATGGATCACCTGGAGGGCCGGC
     ACCGCCGCTTCCCAGTTCTGGACCGACTACCCGTTCGGCTGTGGATGGATCACCTGGAGGGCAGGC

F  H  F  D  D  V  I  S  T  M  R  R  P  S  L  K  D  E  V  Y  V  V
     TTCCATTTCGATGACGTCATCAGCACCATGCGTCGCCCGTCACTGAAAGATGAGGTATACGTGGTG
     TTCCATTTCGATGACGTCATCAGCACCATGCGTCGCCCGTCACTGAAAGATGAGGTCTACGTGGTG
     TTCCATTTTGATGACGTCATCAGCACCATGCGTCGCCCGTCACTGAAAGATGAGGTCTACGTGGTG

G  A  D  Y  S  W  G  L  I  S  S  W  I  E  G  A  L  E  T  S  E  N
     GGAGCCGACTACTCCTGGGGACTTATCTCCTCCTGGATAGAGGGCGCTCTGGAGACCTCGGAAAAC
     GGAGCCGATTACTCCTGGGGACTTATCTCCTCCTGGATAGAGGGCGCTCTGGAGACCTCAGAAAAC
     GGAGCCGATTACTCCTGGGGACTTATCTCCTCCTGGATAGAGGGCGCTCTGGAGACCTCGGAAAAC

V  I  N  D  Y  F  L  -
     GTCATCAACGACTACTTCCTCTAA
     GTCATCAACGACTACTTCCTCTAA
     GTCATCAACGACTACTTCCTCTAA
```

Fig. 4D

```
                              VS
     MSSAVLLLACALVISVHADGICRNRRQCNREVCGSTYDVAVVGA
              ^          ^          ^         ^
             10         20         30         40

T      Q         H       S
     GPGGANSAYMLRDSGLDIAVFEYSDRVGGRLFTYQLPNTPDVNL
              ^          ^          ^         ^
             50         60         70         80
```

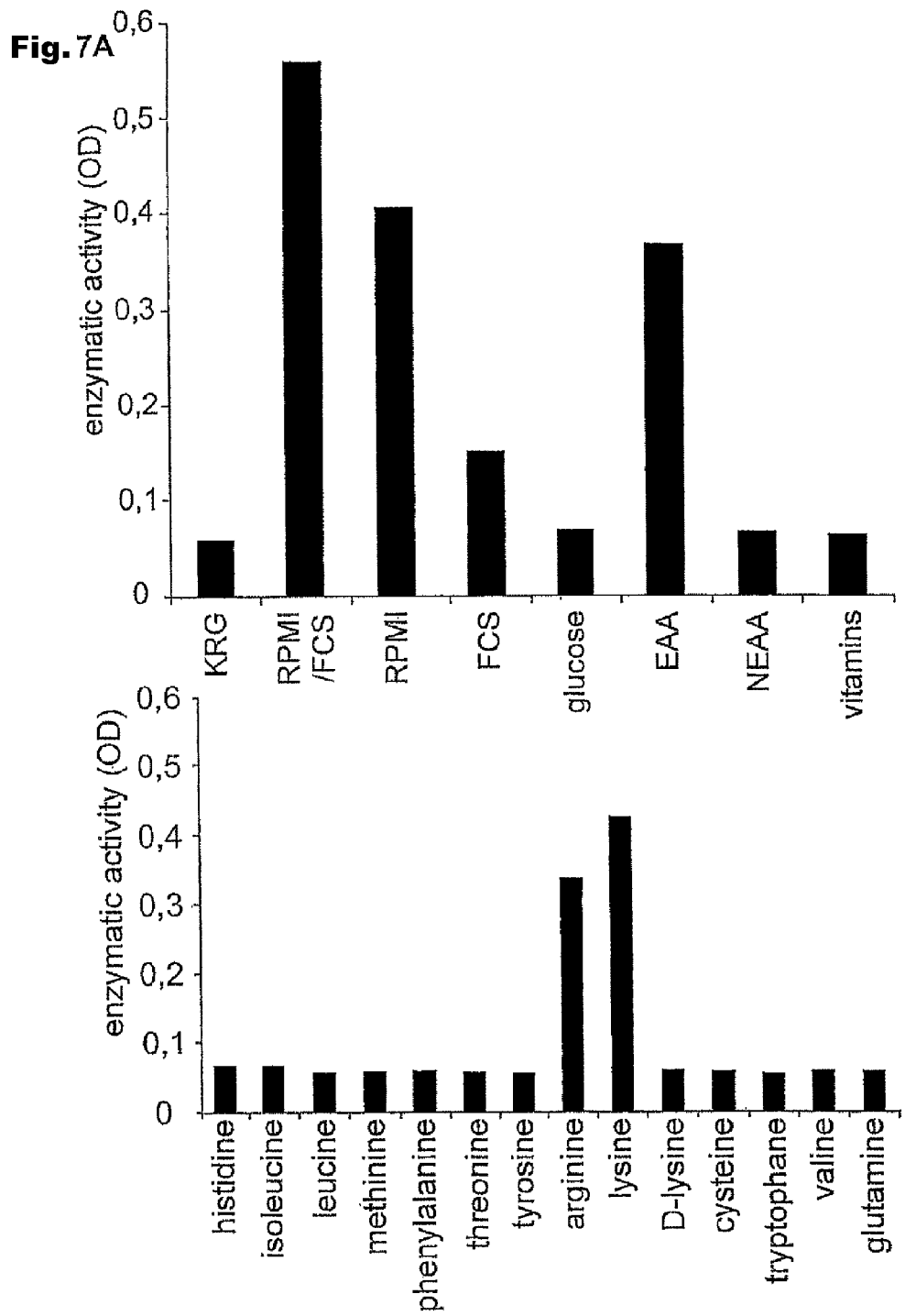

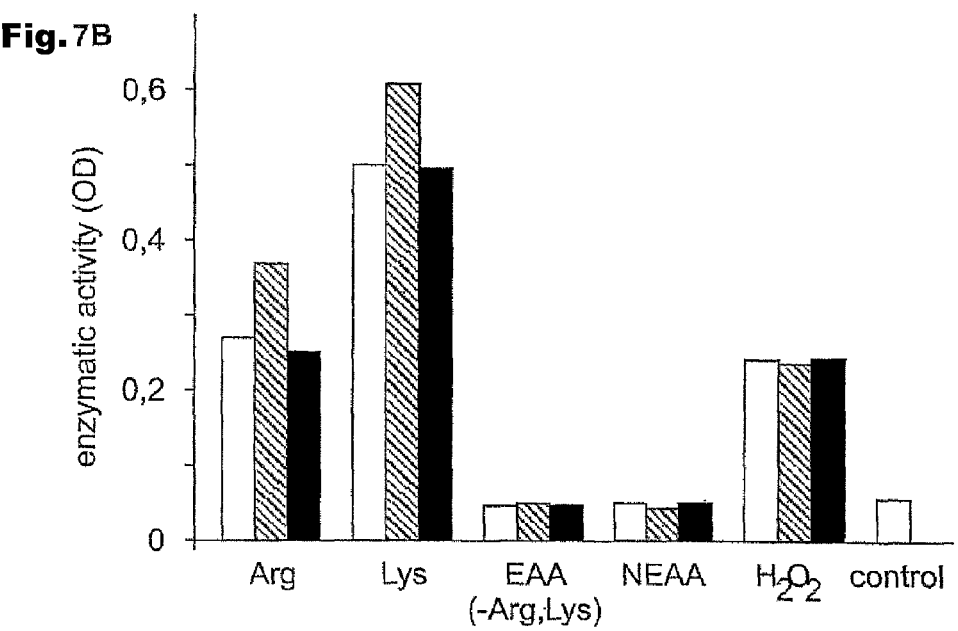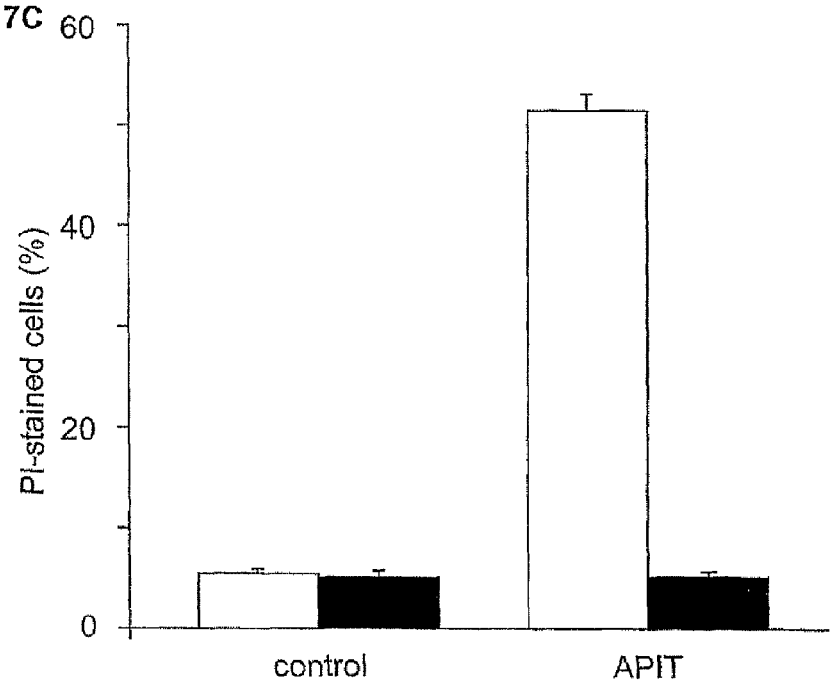

SEQUENCE LISTING

```
<160> NUMBER OF SEQ ID NOS: 78

<210> SEQ ID NO 1
<211> LENGTH: 1608
<212> TYPE: DNA
<213> ORGANISM: Aplysia punctata
<220> FEATURE:
<221> NAME/KEY: CDS
<222> LOCATION: (1)..(1608)

<400> SEQUENCE: 1 atg tcg tct gct gtg ctt ctc ctg gct tgt gcg ttg gtc atc tct gtc        48
Met Ser Ser Ala Val Leu Leu Leu Ala Cys Ala Leu Val Ile Ser Val
  1               5                  10                  15 cac gcc gac ggt atc tgc aga aac aga cgt caa tgt aac aga gag gtg        96
His Ala Asp Gly Ile Cys Arg Asn Arg Arg Gln Cys Asn Arg Glu Val
             20                  25                  30 tgc ggt tct acc tac gat gtg gcc gtc gtg ggg gcg ggg cct ggg gga       144
Cys Gly Ser Thr Tyr Asp Val Ala Val Val Gly Ala Gly Pro Gly Gly
         35                  40                  45 gct aac tcc gcc tac atg ctg agg gac tcc ggc ctg gac atc gct gtg       192
Ala Asn Ser Ala Tyr Met Leu Arg Asp Ser Gly Leu Asp Ile Ala Val
     50                  55                  60 ttc gag tac tcg gac cga gtg ggc ggc cgg ctg ttc acc tac cag ctg       240
Phe Glu Tyr Ser Asp Arg Val Gly Gly Arg Leu Phe Thr Tyr Gln Leu
 65                  70                  75                  80 ccc aac aca ccc gac gtt aac ctg gag att ggc ggc atg agg ttc atc       288
Pro Asn Thr Pro Asp Val Asn Leu Glu Ile Gly Gly Met Arg Phe Ile
                 85                  90                  95 gaa ggc gcc atg cac agg ctc tgg agg gtc att tca gaa ctc ggc cta       336
```

|   |   |   |   |   |   |   |   |   |   |   |   |   |   |   |   |   |
|---|---|---|---|---|---|---|---|---|---|---|---|---|---|---|---|---|
| Glu | Gly | Ala | Met | His | Arg | Leu | Trp | Arg | Val | Ile | Ser | Glu | Leu | Gly | Leu | |
|   |   |   |   | 100 |   |   |   | 105 |   |   |   | 110 |   |   |   | |

```
acc ccc aag gtg ttc aag gaa ggt ttc ggc aag gag ggc aga caa aga       384
Thr Pro Lys Val Phe Lys Glu Gly Phe Gly Lys Glu Gly Arg Gln Arg
            115                 120                 125 ttt tac ctg cgg gga cag agc ctg acc aag aaa cag gtc aag agt ggg       432
Phe Tyr Leu Arg Gly Gln Ser Leu Thr Lys Lys Gln Val Lys Ser Gly
130                 135                 140 gac gta ccc tat gac ctc agc ccg gag gag aaa gaa aac cag gga aat       480
Asp Val Pro Tyr Asp Leu Ser Pro Glu Glu Lys Glu Asn Gln Gly Asn
145                 150                 155                 160 ctg gtc gaa tac tac ctg gag aaa ctg aca ggt cta caa ctc aac ggc       528
Leu Val Glu Tyr Tyr Leu Glu Lys Leu Thr Gly Leu Gln Leu Asn Gly
            165                 170                 175 gag ccg ctc aaa cgt gag gtt gcg ctt aaa cta acc gtg ccg gac ggc       576
Glu Pro Leu Lys Arg Glu Val Ala Leu Lys Leu Thr Val Pro Asp Gly
            180                 185                 190 aga ttc ctc tat gac ctc tcg ttt gac gaa gcc atg gat ctg gtt gcc       624
Arg Phe Leu Tyr Asp Leu Ser Phe Asp Glu Ala Met Asp Leu Val Ala
            195                 200                 205 tcc cct gag ggc aaa gag ttc acc cga gac acg cac gtc ttc aca gga       672
Ser Pro Glu Gly Lys Glu Phe Thr Arg Asp Thr His Val Phe Thr Gly
210                 215                 220 gag gtc acc ctg gac gcg tcg gct gtc tcc ctc ttc gac gac cac ctg       720
Glu Val Thr Leu Asp Ala Ser Ala Val Ser Leu Phe Asp Asp His Leu
225                 230                 235                 240 gga gag gac tac tat ggc agt gag atc tac acc cta aag gaa gga ctg       768
Gly Glu Asp Tyr Tyr Gly Ser Glu Ile Tyr Thr Leu Lys Glu Gly Leu
            245                 250                 255 tct tcc gtc cca caa ggg ctc cta cag gct ttt ctg gac gcc gca gac       816
Ser Ser Val Pro Gln Gly Leu Leu Gln Ala Phe Leu Asp Ala Ala Asp
            260                 265                 270 tcc aac gag ttc tat ccc aac agc cac ctg aag gcc ctg aga cgt aag       864
Ser Asn Glu Phe Tyr Pro Asn Ser His Leu Lys Ala Leu Arg Arg Lys
            275                 280                 285 acc aac ggt cag tat gtt ctt tac ttt gag ccc acc acc tcc aag gat       912
Thr Asn Gly Gln Tyr Val Leu Tyr Phe Glu Pro Thr Thr Ser Lys Asp
290                 295                 300 gga caa acc aca atc aac tat ctg gaa ccc ctg cag gtt gtg tgt gca       960
Gly Gln Thr Thr Ile Asn Tyr Leu Glu Pro Leu Gln Val Val Cys Ala
305                 310                 315                 320 caa aga gtc atc ctg gcc atg ccg gta tac gct ctg aac caa cta gac      1008
Gln Arg Val Ile Leu Ala Met Pro Val Tyr Ala Leu Asn Gln Leu Asp
            325                 330                 335 tgg aat cag ctc aga aat gac cga gcc acc caa gcg tac gct gcc gtt      1056
Trp Asn Gln Leu Arg Asn Asp Arg Ala Thr Gln Ala Tyr Ala Ala Val
            340                 345                 350 cgc ccg att cct gca agt aag gtg ttc atg tcc ttt gat cag ccc tgg      1104
Arg Pro Ile Pro Ala Ser Lys Val Phe Met Ser Phe Asp Gln Pro Trp
            355                 360                 365 tgg ttg gag aac gag agg aaa tcc tgg gtc acc aag tcg gac gcg ctt      1152
Trp Leu Glu Asn Glu Arg Lys Ser Trp Val Thr Lys Ser Asp Ala Leu
370                 375                 380 ttc agc caa atg tac gac tgg cag aag tct gag gcg tcc gga gac tac      1200
Phe Ser Gln Met Tyr Asp Trp Gln Lys Ser Glu Ala Ser Gly Asp Tyr
385                 390                 395                 400 atc ctg atc gcc agc tac gcc gac ggc ctc aaa gcc cag tac ctg cgg      1248
Ile Leu Ile Ala Ser Tyr Ala Asp Gly Leu Lys Ala Gln Tyr Leu Arg
            405                 410                 415
```

| | | |
|---|---|---|
| gag ctg aag aat cag gga gag gac atc cca ggc tct gac cca ggc tac<br>Glu Leu Lys Asn Gln Gly Glu Asp Ile Pro Gly Ser Asp Pro Gly Tyr<br>420                 425                 430 | | 1296 |
| aac cag gtt acc gaa ccc ctc aag gac acc att ctt gac cac ctc act<br>Asn Gln Val Thr Glu Pro Leu Lys Asp Thr Ile Leu Asp His Leu Thr<br>      435                 440                 445 | | 1344 |
| gag gct tat ggc gtg gag cga gac tcg atc ccg gaa ccc gtg acc gcc<br>Glu Ala Tyr Gly Val Glu Arg Asp Ser Ile Pro Glu Pro Val Thr Ala<br>450                 455                 460 | | 1392 |
| gct tcc cag ttc tgg aca gac tac ccg ttt ggc tgt gga tgg atc acc<br>Ala Ser Gln Phe Trp Thr Asp Tyr Pro Phe Gly Cys Gly Trp Ile Thr<br>465                 470                 475                 480 | | 1440 |
| tgg agg gcc ggc ttc cat ttc gat gac gtc atc agc acc atg cgt cgc<br>Trp Arg Ala Gly Phe His Phe Asp Asp Val Ile Ser Thr Met Arg Arg<br>                485                 490                 495 | | 1488 |
| ccg tca ctg aaa gat gag gta tac gtg gtg gga gcc gac tac tcc tgg<br>Pro Ser Leu Lys Asp Glu Val Tyr Val Val Gly Ala Asp Tyr Ser Trp<br>                500                 505                 510 | | 1536 |
| gga ctt atc tcc tcc tgg ata gag ggc gct ctg gag acc tcg gaa aac<br>Gly Leu Ile Ser Ser Trp Ile Glu Gly Ala Leu Glu Thr Ser Glu Asn<br>                515                 520                 525 | | 1584 |
| gtc atc aac gac tac ttc ctc taa<br>Val Ile Asn Asp Tyr Phe Leu<br>530                 535 | | 1608 |

<210> SEQ ID NO 2
<211> LENGTH: 535
<212> TYPE: PRT
<213> ORGANISM: Aplysia punctata

<400> SEQUENCE: 2

Met Ser Ser Ala Val Leu Leu Ala Cys Ala Leu Val Ile Ser Val
1               5                   10                  15

His Ala Asp Gly Ile Cys Arg Asn Arg Arg Gln Cys Asn Arg Glu Val
            20                  25                  30

Cys Gly Ser Thr Tyr Asp Val Ala Val Gly Ala Gly Pro Gly Gly
        35                  40                  45

Ala Asn Ser Ala Tyr Met Leu Arg Asp Ser Gly Leu Asp Ile Ala Val
    50                  55                  60

Phe Glu Tyr Ser Asp Arg Val Gly Gly Arg Leu Phe Thr Tyr Gln Leu
65                  70                  75                  80

Pro Asn Thr Pro Asp Val Asn Leu Glu Ile Gly Gly Met Arg Phe Ile
                85                  90                  95

Glu Gly Ala Met His Arg Leu Trp Arg Val Ile Ser Glu Leu Gly Leu
            100                 105                 110

Thr Pro Lys Val Phe Lys Glu Gly Phe Gly Lys Glu Gly Arg Gln Arg
        115                 120                 125

Phe Tyr Leu Arg Gly Gln Ser Leu Thr Lys Lys Gln Val Lys Ser Gly
    130                 135                 140

Asp Val Pro Tyr Asp Leu Ser Pro Glu Glu Lys Glu Asn Gln Gly Asn
145                 150                 155                 160

Leu Val Glu Tyr Tyr Leu Glu Lys Leu Thr Gly Leu Gln Leu Asn Gly
                165                 170                 175

Glu Pro Leu Lys Arg Glu Val Ala Leu Lys Leu Thr Val Pro Asp Gly
            180                 185                 190

Arg Phe Leu Tyr Asp Leu Ser Phe Asp Glu Ala Met Asp Leu Val Ala
        195                 200                 205

```
Ser Pro Glu Gly Lys Glu Phe Thr Arg Asp Thr His Val Phe Thr Gly
    210                 215                 220
Glu Val Thr Leu Asp Ala Ser Ala Val Ser Leu Phe Asp Asp His Leu
225                 230                 235                 240
Gly Glu Asp Tyr Tyr Gly Ser Glu Ile Tyr Thr Leu Lys Glu Gly Leu
            245                 250                 255
Ser Ser Val Pro Gln Gly Leu Leu Gln Ala Phe Leu Asp Ala Ala Asp
        260                 265                 270
Ser Asn Glu Phe Tyr Pro Asn Ser His Leu Lys Ala Leu Arg Arg Lys
    275                 280                 285
Thr Asn Gly Gln Tyr Val Leu Tyr Phe Glu Pro Thr Thr Ser Lys Asp
290                 295                 300
Gly Gln Thr Thr Ile Asn Tyr Leu Glu Pro Leu Gln Val Val Cys Ala
305                 310                 315                 320
Gln Arg Val Ile Leu Ala Met Pro Val Tyr Ala Leu Asn Gln Leu Asp
            325                 330                 335
Trp Asn Gln Leu Arg Asn Asp Arg Ala Thr Gln Ala Tyr Ala Ala Val
        340                 345                 350
Arg Pro Ile Pro Ala Ser Lys Val Phe Met Ser Phe Asp Gln Pro Trp
    355                 360                 365
Trp Leu Glu Asn Glu Arg Lys Ser Trp Val Thr Lys Ser Asp Ala Leu
370                 375                 380
Phe Ser Gln Met Tyr Asp Trp Gln Lys Ser Glu Ala Ser Gly Asp Tyr
385                 390                 395                 400
Ile Leu Ile Ala Ser Tyr Ala Asp Gly Leu Lys Ala Gln Tyr Leu Arg
            405                 410                 415
Glu Leu Lys Asn Gln Gly Glu Asp Ile Pro Gly Ser Asp Pro Gly Tyr
        420                 425                 430
Asn Gln Val Thr Glu Pro Leu Lys Asp Thr Ile Leu Asp His Leu Thr
    435                 440                 445
Glu Ala Tyr Gly Val Glu Arg Asp Ser Ile Pro Glu Pro Val Thr Ala
450                 455                 460
Ala Ser Gln Phe Trp Thr Asp Tyr Pro Phe Gly Cys Gly Trp Ile Thr
465                 470                 475                 480
Trp Arg Ala Gly Phe His Phe Asp Asp Val Ile Ser Thr Met Arg Arg
            485                 490                 495
Pro Ser Leu Lys Asp Glu Val Tyr Val Val Gly Ala Asp Tyr Ser Trp
        500                 505                 510
Gly Leu Ile Ser Ser Trp Ile Glu Gly Ala Leu Glu Thr Ser Glu Asn
    515                 520                 525
Val Ile Asn Asp Tyr Phe Leu
530                 535

<210> SEQ ID NO 3
<211> LENGTH: 1605
<212> TYPE: DNA
<213> ORGANISM: Aplysia punctata
<220> FEATURE:
<221> NAME/KEY: CDS
<222> LOCATION: (1)..(1605)

<400> SEQUENCE: 3 tcg tct gct gtg ctt ctc ctg gct tgt gcg ttg gtc atc tct gtc cac      48
Ser Ser Ala Val Leu Leu Leu Ala Cys Ala Leu Val Ile Ser Val His
  1               5                  10                  15 gcc gac ggt gtc tgc aga aac aga cgt caa tgt aac aga gag gtg tgc      96
```

|     |     |     |     |     |     |     |     |     |     |     |     |     |     |     |
|-----|-----|-----|-----|-----|-----|-----|-----|-----|-----|-----|-----|-----|-----|-----|
| Ala | Asp | Gly | Val | Cys | Arg | Asn | Arg | Arg | Gln | Cys | Asn | Arg | Glu | Val | Cys |
|     |     |     | 20  |     |     |     | 25  |     |     |     | 30  |     |     |     |

```
ggt tct acc tac gat gtg gcc gtc gtg ggg gcg ggg cct ggg gga gct       144
Gly Ser Thr Tyr Asp Val Ala Val Val Gly Ala Gly Pro Gly Gly Ala
         35                  40                  45 aac tcc gcc tac atg ctg agg gac tcc ggc ctg gac atc gct gtg ttc       192
Asn Ser Ala Tyr Met Leu Arg Asp Ser Gly Leu Asp Ile Ala Val Phe
     50                  55                  60 gag tac tca gac cga gtg ggc ggc cgg ctg ttc acc tac cag ctg ccc       240
Glu Tyr Ser Asp Arg Val Gly Gly Arg Leu Phe Thr Tyr Gln Leu Pro
 65                  70                  75                  80 aac aca ccc gac gtt aat ctc gag att ggc ggc atg agg ttc atc gag       288
Asn Thr Pro Asp Val Asn Leu Glu Ile Gly Gly Met Arg Phe Ile Glu
                 85                  90                  95 ggc gcc atg cac agg ctc tgg agg gtc att tca gaa ctc ggc cta acc       336
Gly Ala Met His Arg Leu Trp Arg Val Ile Ser Glu Leu Gly Leu Thr
             100                 105                 110 ccc aag gtg ttc aag gaa ggt ttc gga aag gag ggc aga cag aga ttt       384
Pro Lys Val Phe Lys Glu Gly Phe Gly Lys Glu Gly Arg Gln Arg Phe
         115                 120                 125 tac ctg cgg gga cag agc ctg acc aag aaa cag gtc aag agt ggg gac       432
Tyr Leu Arg Gly Gln Ser Leu Thr Lys Lys Gln Val Lys Ser Gly Asp
 130                 135                 140 gta ccc tat gac ctc agc ccg gag gag aaa gaa aac cag gga aat ctg       480
Val Pro Tyr Asp Leu Ser Pro Glu Glu Lys Glu Asn Gln Gly Asn Leu
145                 150                 155                 160 gtc gaa tac tac ctg gag aaa ctg aca ggt cta caa ctc aat ggt gaa       528
Val Glu Tyr Tyr Leu Glu Lys Leu Thr Gly Leu Gln Leu Asn Gly Glu
                 165                 170                 175 ccg ctc aaa cgt gag gtt gcg ctt aaa cta acc gtg ccg gac ggc aga       576
Pro Leu Lys Arg Glu Val Ala Leu Lys Leu Thr Val Pro Asp Gly Arg
             180                 185                 190 ttc ctc tat gac ctc tcg ttt gac gaa gcc atg gat ctg gtt gcc tcc       624
Phe Leu Tyr Asp Leu Ser Phe Asp Glu Ala Met Asp Leu Val Ala Ser
         195                 200                 205 cct gag ggc aaa gag ttc acc cga gac acg cac gtc ttc acc gga gag       672
Pro Glu Gly Lys Glu Phe Thr Arg Asp Thr His Val Phe Thr Gly Glu
 210                 215                 220 gtc acc ctg ggc gcg tcg gct gtc tcc ctc ttc gac gac cac ctg gga       720
Val Thr Leu Gly Ala Ser Ala Val Ser Leu Phe Asp Asp His Leu Gly
225                 230                 235                 240 gag gac tac tac ggc agt gag atc tac acc ctc aag gaa gga ctg tct       768
Glu Asp Tyr Tyr Gly Ser Glu Ile Tyr Thr Leu Lys Glu Gly Leu Ser
                 245                 250                 255 tcc gtc cct caa ggg ctc cta cag gct ttt ctg gac gcc gca gac tcc       816
Ser Val Pro Gln Gly Leu Leu Gln Ala Phe Leu Asp Ala Ala Asp Ser
             260                 265                 270 aac gag ttc tat ccc aac agc cac ctg aag gcc ctg aga cgt aag acc       864
Asn Glu Phe Tyr Pro Asn Ser His Leu Lys Ala Leu Arg Arg Lys Thr
         275                 280                 285 aac ggt cag tat gtt ctt tac ttt gag ccc acc acc tcc aag gat gga       912
Asn Gly Gln Tyr Val Leu Tyr Phe Glu Pro Thr Thr Ser Lys Asp Gly
 290                 295                 300 caa acc aca atc aac tat ctg gaa ccc ctg cag gtt gtg tgt gca cag       960
Gln Thr Thr Ile Asn Tyr Leu Glu Pro Leu Gln Val Val Cys Ala Gln
305                 310                 315                 320 aga gtc att ctg gcc atg ccg gtc tac gct ctc aac cag ttg gat tgg      1008
Arg Val Ile Leu Ala Met Pro Val Tyr Ala Leu Asn Gln Leu Asp Trp
                 325                 330                 335
```

```
aat cag ctc aga aat gac cga gcc acc caa gcg tac gct gcc gtg cgc      1056
Asn Gln Leu Arg Asn Asp Arg Ala Thr Gln Ala Tyr Ala Ala Val Arg
            340                 345                 350 ccg att cct gca agt aag gtg ttc atg acc ttt gat cag ccc tgg tgg      1104
Pro Ile Pro Ala Ser Lys Val Phe Met Thr Phe Asp Gln Pro Trp Trp
        355                 360                 365 ttg gag aac gag agg aaa tcc tgg gtc acc aag tcg gac gcg ctt ttc      1152
Leu Glu Asn Glu Arg Lys Ser Trp Val Thr Lys Ser Asp Ala Leu Phe
    370                 375                 380 agt caa atg tac gac tgg cag aag tct gag gcg tcc gga gac tac atc      1200
Ser Gln Met Tyr Asp Trp Gln Lys Ser Glu Ala Ser Gly Asp Tyr Ile
385                 390                 395                 400 ctg atc gcc agc tac gcc gac ggc ctc aaa gcc cag tac ctg cgg gag      1248
Leu Ile Ala Ser Tyr Ala Asp Gly Leu Lys Ala Gln Tyr Leu Arg Glu
                405                 410                 415 ctg aag aat cag gga gag gac atc cca ggc tct gac cca ggc tac aac      1296
Leu Lys Asn Gln Gly Glu Asp Ile Pro Gly Ser Asp Pro Gly Tyr Asn
            420                 425                 430 cag gtc acc gaa ccc ctc aag gac acc att ctt gac cac ctc act gag      1344
Gln Val Thr Glu Pro Leu Lys Asp Thr Ile Leu Asp His Leu Thr Glu
        435                 440                 445 gcc tat ggc gtg gag cga gac tcg atc cgg gaa ccc gtg acc gcc gct      1392
Ala Tyr Gly Val Glu Arg Asp Ser Ile Arg Glu Pro Val Thr Ala Ala
    450                 455                 460 tcc cag ttc tgg aca gac tac ccg ttt ggc tgt gga tgg atc acc tgg      1440
Ser Gln Phe Trp Thr Asp Tyr Pro Phe Gly Cys Gly Trp Ile Thr Trp
465                 470                 475                 480 agg gcc ggc ttc cat ttc gat gac gtc atc agc acc atg cgt cgc ccg      1488
Arg Ala Gly Phe His Phe Asp Asp Val Ile Ser Thr Met Arg Arg Pro
                485                 490                 495 tca ctg aaa gat gag gtc tac gtg gtg gga gcc gat tac tcc tgg gga      1536
Ser Leu Lys Asp Glu Val Tyr Val Val Gly Ala Asp Tyr Ser Trp Gly
            500                 505                 510 ctt atc tcc tcc tgg ata gag ggc gct ctg gag acc tca gaa aac gtc      1584
Leu Ile Ser Ser Trp Ile Glu Gly Ala Leu Glu Thr Ser Glu Asn Val
        515                 520                 525 atc aac gac tac ttc ctc taa                                          1605
Ile Asn Asp Tyr Phe Leu
    530
```

<210> SEQ ID NO 4
<211> LENGTH: 534
<212> TYPE: PRT
<213> ORGANISM: Aplysia punctata

<400> SEQUENCE: 4

```
Ser Ser Ala Val Leu Leu Leu Ala Cys Ala Leu Val Ile Ser Val His
1               5                   10                  15

Ala Asp Gly Val Cys Arg Asn Arg Arg Gln Cys Asn Arg Glu Val Cys
            20                  25                  30

Gly Ser Thr Tyr Asp Val Ala Val Val Gly Ala Gly Pro Gly Gly Ala
        35                  40                  45

Asn Ser Ala Tyr Met Leu Arg Asp Ser Gly Leu Asp Ile Ala Val Phe
    50                  55                  60

Glu Tyr Ser Asp Arg Val Gly Gly Arg Leu Phe Thr Tyr Gln Leu Pro
65                  70                  75                  80

Asn Thr Pro Asp Val Asn Leu Glu Ile Gly Gly Met Arg Phe Ile Glu
                85                  90                  95

Gly Ala Met His Arg Leu Trp Arg Val Ile Ser Glu Leu Gly Leu Thr
```

```
                   100                 105                 110
Pro Lys Val Phe Lys Glu Gly Phe Gly Lys Glu Gly Arg Gln Arg Phe
                115                 120                 125

Tyr Leu Arg Gly Gln Ser Leu Thr Lys Lys Gln Val Lys Ser Gly Asp
    130                 135                 140

Val Pro Tyr Asp Leu Ser Pro Glu Glu Lys Glu Asn Gln Gly Asn Leu
145                 150                 155                 160

Val Glu Tyr Tyr Leu Glu Lys Leu Thr Gly Leu Gln Leu Asn Gly Glu
                165                 170                 175

Pro Leu Lys Arg Glu Val Ala Leu Lys Leu Thr Val Pro Asp Gly Arg
            180                 185                 190

Phe Leu Tyr Asp Leu Ser Phe Asp Glu Ala Met Asp Leu Val Ala Ser
        195                 200                 205

Pro Glu Gly Lys Glu Phe Thr Arg Asp Thr His Val Phe Thr Gly Glu
    210                 215                 220

Val Thr Leu Gly Ala Ser Ala Val Ser Leu Phe Asp Asp His Leu Gly
225                 230                 235                 240

Glu Asp Tyr Tyr Gly Ser Glu Ile Tyr Thr Leu Lys Glu Gly Leu Ser
                245                 250                 255

Ser Val Pro Gln Gly Leu Leu Gln Ala Phe Leu Asp Ala Ala Asp Ser
            260                 265                 270

Asn Glu Phe Tyr Pro Asn Ser His Leu Lys Ala Leu Arg Arg Lys Thr
        275                 280                 285

Asn Gly Gln Tyr Val Leu Tyr Phe Glu Pro Thr Thr Ser Lys Asp Gly
    290                 295                 300

Gln Thr Thr Ile Asn Tyr Leu Glu Pro Leu Gln Val Val Cys Ala Gln
305                 310                 315                 320

Arg Val Ile Leu Ala Met Pro Val Tyr Ala Leu Asn Gln Leu Asp Trp
                325                 330                 335

Asn Gln Leu Arg Asn Asp Arg Ala Thr Gln Ala Tyr Ala Ala Val Arg
            340                 345                 350

Pro Ile Pro Ala Ser Lys Val Phe Met Thr Phe Asp Gln Pro Trp Trp
        355                 360                 365

Leu Glu Asn Glu Arg Lys Ser Trp Val Thr Lys Ser Asp Ala Leu Phe
    370                 375                 380

Ser Gln Met Tyr Asp Trp Gln Lys Ser Glu Ala Ser Gly Asp Tyr Ile
385                 390                 395                 400

Leu Ile Ala Ser Tyr Ala Asp Gly Leu Lys Ala Gln Tyr Leu Arg Glu
                405                 410                 415

Leu Lys Asn Gln Gly Glu Asp Ile Pro Gly Ser Asp Pro Gly Tyr Asn
            420                 425                 430

Gln Val Thr Glu Pro Leu Lys Asp Thr Ile Leu Asp His Leu Thr Glu
        435                 440                 445

Ala Tyr Gly Val Glu Arg Asp Ser Ile Arg Glu Pro Val Thr Ala Ala
    450                 455                 460

Ser Gln Phe Trp Thr Asp Tyr Pro Phe Gly Cys Gly Trp Ile Thr Trp
465                 470                 475                 480

Arg Ala Gly Phe His Phe Asp Asp Val Ile Ser Thr Met Arg Arg Pro
                485                 490                 495

Ser Leu Lys Asp Glu Val Tyr Val Val Gly Ala Asp Tyr Ser Trp Gly
            500                 505                 510

Leu Ile Ser Ser Trp Ile Glu Gly Ala Leu Glu Thr Ser Glu Asn Val
        515                 520                 525
```

```
Ile Asn Asp Tyr Phe Leu
        530

<210> SEQ ID NO 5
<211> LENGTH: 1554
<212> TYPE: DNA
<213> ORGANISM: Aplysia punctata
<220> FEATURE:
<221> NAME/KEY: CDS
<222> LOCATION: (1)..(1554)

<400> SEQUENCE: 5 gac ggt atc tgc aga aac aga cgt caa tgt aac aga gag gtg tgc ggt       48
Asp Gly Ile Cys Arg Asn Arg Arg Gln Cys Asn Arg Glu Val Cys Gly
1               5                   10                  15 tct acc tac gat gtg gct gtc gtg ggg gcg ggg cct ggg gga gct aac       96
Ser Thr Tyr Asp Val Ala Val Val Gly Ala Gly Pro Gly Gly Ala Asn
            20                  25                  30 tcc gcc tac atg ctg agg gac tcc ggc ctg gac atc gct gtg ttc gag      144
Ser Ala Tyr Met Leu Arg Asp Ser Gly Leu Asp Ile Ala Val Phe Glu
        35                  40                  45 tac tca gac cga gtg ggc ggc cgg ctg ttc acc tac cag ctg ccc aac      192
Tyr Ser Asp Arg Val Gly Gly Arg Leu Phe Thr Tyr Gln Leu Pro Asn
    50                  55                  60 aca ccc gac gtt aat ctc gag att ggc ggc atg agg ttc atc gag ggc      240
Thr Pro Asp Val Asn Leu Glu Ile Gly Gly Met Arg Phe Ile Glu Gly
65                  70                  75                  80 gcc atg cac agg ctc tgg agg gtc att tca gaa ctc ggc cta acc ccc      288
Ala Met His Arg Leu Trp Arg Val Ile Ser Glu Leu Gly Leu Thr Pro
                85                  90                  95 aag gtg ttc aag gaa ggt ttc gga aag gag ggc aga cag aga ttt tac      336
Lys Val Phe Lys Glu Gly Phe Gly Lys Glu Gly Arg Gln Arg Phe Tyr
            100                 105                 110 ctg cgg gga cag agc ctg acc aag aaa cag gtc aag agt ggg gac gta      384
Leu Arg Gly Gln Ser Leu Thr Lys Lys Gln Val Lys Ser Gly Asp Val
        115                 120                 125 ccc tat gac ctc agc ccg gag gag aaa gaa aac cag gga aat ctg gtc      432
Pro Tyr Asp Leu Ser Pro Glu Glu Lys Glu Asn Gln Gly Asn Leu Val
    130                 135                 140 gaa tac tac ctg gag aaa ctg aca ggt cta aaa ctc aac ggc gga ccg      480
Glu Tyr Tyr Leu Glu Lys Leu Thr Gly Leu Lys Leu Asn Gly Gly Pro
145                 150                 155                 160 ctc aaa cgt gag gtt gcg ctt aaa cta acc gtg ccg gac ggc aga ttc      528
Leu Lys Arg Glu Val Ala Leu Lys Leu Thr Val Pro Asp Gly Arg Phe
                165                 170                 175 ctc tat gac ctc tcg ttt gac gaa gcc atg gac ctg gtt gcc tcc cct      576
Leu Tyr Asp Leu Ser Phe Asp Glu Ala Met Asp Leu Val Ala Ser Pro
            180                 185                 190 gag ggc aaa gag ttc acc cga gac acg cac gtg ttc acc gga gaa gtc      624
Glu Gly Lys Glu Phe Thr Arg Asp Thr His Val Phe Thr Gly Glu Val
        195                 200                 205 acc ctg gac gcg tcg gct gtc tcc ctc ttc gac gac cac ctg gga gag      672
Thr Leu Asp Ala Ser Ala Val Ser Leu Phe Asp Asp His Leu Gly Glu
    210                 215                 220 gac tac tat ggc agt gag atc tac acc cta aag gaa gga ctg tct tcc      720
Asp Tyr Tyr Gly Ser Glu Ile Tyr Thr Leu Lys Glu Gly Leu Ser Ser
225                 230                 235                 240 gtc cca caa ggg ctc cta cag act ttt ctg gac gcc gca gac tcc aac      768
Val Pro Gln Gly Leu Leu Gln Thr Phe Leu Asp Ala Ala Asp Ser Asn
                245                 250                 255
```

```
gag ttc tat ccc aac agc cac ctg aag gcc ctg aga cgt aag acc aac      816
Glu Phe Tyr Pro Asn Ser His Leu Lys Ala Leu Arg Arg Lys Thr Asn
                260                 265                 270 ggt cag tat gtt ctt tac ttt gag ccc acc acc tcc aag gat gga caa      864
Gly Gln Tyr Val Leu Tyr Phe Glu Pro Thr Thr Ser Lys Asp Gly Gln
            275                 280                 285 acc aca atc aac tat ctg gaa ccc ctg cag gtt gtg tgt gca cag aga      912
Thr Thr Ile Asn Tyr Leu Glu Pro Leu Gln Val Val Cys Ala Gln Arg
        290                 295                 300 gtc atc ctg gcc atg ccg gtc tac gct ctc aac caa ctg gac tgg aat      960
Val Ile Leu Ala Met Pro Val Tyr Ala Leu Asn Gln Leu Asp Trp Asn
305                 310                 315                 320 cag ctc aga aat gac cga gcc acc caa gcg tac gct gcc gtg cgc ccg     1008
Gln Leu Arg Asn Asp Arg Ala Thr Gln Ala Tyr Ala Ala Val Arg Pro
                325                 330                 335 att cct gca agt aaa gtg ttc atg acc ttt gat cag ccc tgg tgg ttg     1056
Ile Pro Ala Ser Lys Val Phe Met Thr Phe Asp Gln Pro Trp Trp Leu
            340                 345                 350 gag aac gag agg aaa tcc tgg gtc acc aag tcg gac gcg ctt ttc agc     1104
Glu Asn Glu Arg Lys Ser Trp Val Thr Lys Ser Asp Ala Leu Phe Ser
        355                 360                 365 caa atg tac gac tgg cag aag tct gag gcg tcc gga gac tac atc ctg     1152
Gln Met Tyr Asp Trp Gln Lys Ser Glu Ala Ser Gly Asp Tyr Ile Leu
370                 375                 380 atc gcc agc tac gcc gac ggc ctc aaa gcc cag tac ctg cgg gag ctg     1200
Ile Ala Ser Tyr Ala Asp Gly Leu Lys Ala Gln Tyr Leu Arg Glu Leu
385                 390                 395                 400 aag aat cag gga gag gac atc cca ggc tct gac cca ggc tac aac cag     1248
Lys Asn Gln Gly Glu Asp Ile Pro Gly Ser Asp Pro Gly Tyr Asn Gln
                405                 410                 415 gtc acc gaa ccc ctc aag gac acc att ctt gac cac ctc act gag gct     1296
Val Thr Glu Pro Leu Lys Asp Thr Ile Leu Asp His Leu Thr Glu Ala
            420                 425                 430 tat ggc gtg gaa cga gac tcg atc ccg gaa ccc gtg acc gcc gct tcc     1344
Tyr Gly Val Glu Arg Asp Ser Ile Pro Glu Pro Val Thr Ala Ala Ser
        435                 440                 445 cag ttc tgg acc gac tac ccg ttc ggc tgt gga tgg atc acc tgg agg     1392
Gln Phe Trp Thr Asp Tyr Pro Phe Gly Cys Gly Trp Ile Thr Trp Arg
    450                 455                 460 gca ggc ttc cat ttt gat gac gtc atc agc acc atg cgt cgc ccg tca     1440
Ala Gly Phe His Phe Asp Asp Val Ile Ser Thr Met Arg Arg Pro Ser
465                 470                 475                 480 ctg aaa gat gag gtc tac gtg gtg gga gcc gat tac tcc tgg gga ctt     1488
Leu Lys Asp Glu Val Tyr Val Val Gly Ala Asp Tyr Ser Trp Gly Leu
                485                 490                 495 atc tcc tcc tgg ata gag ggc gct ctg gag acc tcg gaa aac gtc atc     1536
Ile Ser Ser Trp Ile Glu Gly Ala Leu Glu Thr Ser Glu Asn Val Ile
            500                 505                 510 aac gac tac ttc ctc taa                                             1554
Asn Asp Tyr Phe Leu
        515

<210> SEQ ID NO 6
<211> LENGTH: 517
<212> TYPE: PRT
<213> ORGANISM: Aplysia punctata

<400> SEQUENCE: 6

Asp Gly Ile Cys Arg Asn Arg Arg Gln Cys Asn Arg Glu Val Cys Gly
1               5                   10                  15
```

-continued

```
Ser Thr Tyr Asp Val Ala Val Val Gly Ala Gly Pro Gly Gly Ala Asn
             20                  25                  30

Ser Ala Tyr Met Leu Arg Asp Ser Gly Leu Asp Ile Ala Val Phe Glu
         35                  40                  45

Tyr Ser Asp Arg Val Gly Gly Arg Leu Phe Thr Tyr Gln Leu Pro Asn
     50                  55                  60

Thr Pro Asp Val Asn Leu Glu Ile Gly Gly Met Arg Phe Ile Glu Gly
 65                  70                  75                  80

Ala Met His Arg Leu Trp Arg Val Ile Ser Glu Leu Gly Leu Thr Pro
                 85                  90                  95

Lys Val Phe Lys Glu Gly Phe Gly Lys Glu Gly Arg Gln Arg Phe Tyr
             100                 105                 110

Leu Arg Gly Gln Ser Leu Thr Lys Lys Gln Val Lys Ser Gly Asp Val
         115                 120                 125

Pro Tyr Asp Leu Ser Pro Glu Glu Lys Glu Asn Gln Gly Asn Leu Val
     130                 135                 140

Glu Tyr Tyr Leu Glu Lys Leu Thr Gly Leu Lys Leu Asn Gly Gly Pro
145                 150                 155                 160

Leu Lys Arg Glu Val Ala Leu Lys Leu Thr Val Pro Asp Gly Arg Phe
                 165                 170                 175

Leu Tyr Asp Leu Ser Phe Asp Glu Ala Met Asp Leu Val Ala Ser Pro
             180                 185                 190

Glu Gly Lys Glu Phe Thr Arg Asp Thr His Val Phe Thr Gly Glu Val
         195                 200                 205

Thr Leu Asp Ala Ser Ala Val Ser Leu Phe Asp His Leu Gly Glu
210                 215                 220

Asp Tyr Tyr Gly Ser Glu Ile Tyr Thr Leu Lys Glu Gly Leu Ser Ser
225                 230                 235                 240

Val Pro Gln Gly Leu Leu Gln Thr Phe Leu Asp Ala Ala Asp Ser Asn
                 245                 250                 255

Glu Phe Tyr Pro Asn Ser His Leu Lys Ala Leu Arg Arg Lys Thr Asn
             260                 265                 270

Gly Gln Tyr Val Leu Tyr Phe Glu Pro Thr Thr Ser Lys Asp Gly Gln
         275                 280                 285

Thr Thr Ile Asn Tyr Leu Glu Pro Leu Gln Val Val Cys Ala Gln Arg
     290                 295                 300

Val Ile Leu Ala Met Pro Val Tyr Ala Leu Asn Gln Leu Asp Trp Asn
305                 310                 315                 320

Gln Leu Arg Asn Asp Arg Ala Thr Gln Ala Tyr Ala Ala Val Arg Pro
                 325                 330                 335

Ile Pro Ala Ser Lys Val Phe Met Thr Phe Asp Gln Pro Trp Trp Leu
             340                 345                 350

Glu Asn Glu Arg Lys Ser Trp Val Thr Lys Ser Asp Ala Leu Phe Ser
         355                 360                 365

Gln Met Tyr Asp Trp Gln Lys Ser Glu Ala Ser Gly Asp Tyr Ile Leu
     370                 375                 380

Ile Ala Ser Tyr Ala Asp Gly Leu Lys Ala Gln Tyr Leu Arg Glu Leu
385                 390                 395                 400

Lys Asn Gln Gly Glu Asp Ile Pro Gly Ser Asp Pro Gly Tyr Asn Gln
                 405                 410                 415

Val Thr Glu Pro Leu Lys Asp Thr Ile Leu Asp His Leu Thr Glu Ala
             420                 425                 430

Tyr Gly Val Glu Arg Asp Ser Ile Pro Glu Pro Val Thr Ala Ala Ser
```

```
                435              440              445
Gln Phe Trp Thr Asp Tyr Pro Phe Gly Cys Gly Trp Ile Thr Trp Arg
    450              455              460

Ala Gly Phe His Phe Asp Asp Val Ile Ser Thr Met Arg Arg Pro Ser
465              470              475              480

Leu Lys Asp Glu Val Tyr Val Gly Ala Asp Tyr Ser Trp Gly Leu
                485              490              495

Ile Ser Ser Trp Ile Glu Gly Ala Leu Glu Thr Ser Glu Asn Val Ile
        500              505              510

Asn Asp Tyr Phe Leu
        515

<210> SEQ ID NO 7
<211> LENGTH: 600
<212> TYPE: DNA
<213> ORGANISM: Homo sapiens
<220> FEATURE:
<221> NAME/KEY: CDS
<222> LOCATION: (1)..(600)

<400> SEQUENCE: 7 atg tct tca gga aat gct aaa att ggg cac cct gcc ccc aac ttc aaa        48
Met Ser Ser Gly Asn Ala Lys Ile Gly His Pro Ala Pro Asn Phe Lys
1               5                   10                  15 gcc aca gct gtt atg cca gat ggt cag ttt aaa gat atc agc ctg tct        96
Ala Thr Ala Val Met Pro Asp Gly Gln Phe Lys Asp Ile Ser Leu Ser
            20                  25                  30 gac tac aaa gga aaa tat gtt gtg ttc ttc ttt tac cct ctt gac ttc       144
Asp Tyr Lys Gly Lys Tyr Val Val Phe Phe Phe Tyr Pro Leu Asp Phe
        35                  40                  45 acc ttt gtg tgc ccc acg gag atc att gct ttc agt gat agg gca gaa       192
Thr Phe Val Cys Pro Thr Glu Ile Ile Ala Phe Ser Asp Arg Ala Glu
    50                  55                  60 gaa ttt aag aaa ctc aac tgc caa gtg att ggt gct tct gtg gat tct       240
Glu Phe Lys Lys Leu Asn Cys Gln Val Ile Gly Ala Ser Val Asp Ser
65                  70                  75                  80 cac ttc tgt cat cta gca tgg gtc aat aca cct aag aaa caa gga gga       288
His Phe Cys His Leu Ala Trp Val Asn Thr Pro Lys Lys Gln Gly Gly
                85                  90                  95 ctg gga ccc atg aac att cct ttg gta tca gac ccg aag cgc acc att       336
Leu Gly Pro Met Asn Ile Pro Leu Val Ser Asp Pro Lys Arg Thr Ile
            100                 105                 110 gct cag gat tat ggg gtc tta aag gct gat gaa ggc atc tcg ttc agg       384
Ala Gln Asp Tyr Gly Val Leu Lys Ala Asp Glu Gly Ile Ser Phe Arg
        115                 120                 125 ggc ctt ttt atc att gat gat aag ggt att ctt cgg cag atc act gta       432
Gly Leu Phe Ile Ile Asp Asp Lys Gly Ile Leu Arg Gln Ile Thr Val
    130                 135                 140 aat gac ctc cct gtt ggc cgc tct gtg gat gag act ttg aga cta gtt       480
Asn Asp Leu Pro Val Gly Arg Ser Val Asp Glu Thr Leu Arg Leu Val
145                 150                 155                 160 cag gcc ttc cag ttc act gac aaa cat ggg gaa gtg tgc cca gct ggc       528
Gln Ala Phe Gln Phe Thr Asp Lys His Gly Glu Val Cys Pro Ala Gly
                165                 170                 175 tgg aaa cct ggc agt gat acc atc aag cct gat gtc caa aag agc aaa       576
Trp Lys Pro Gly Ser Asp Thr Ile Lys Pro Asp Val Gln Lys Ser Lys
            180                 185                 190 gaa tat ttc tcc aag cag aag tga                                       600
Glu Tyr Phe Ser Lys Gln Lys
        195
```

<210> SEQ ID NO 8
<211> LENGTH: 199
<212> TYPE: PRT
<213> ORGANISM: Homo sapiens

<400> SEQUENCE: 8

Met Ser Ser Gly Asn Ala Lys Ile Gly His Pro Ala Pro Asn Phe Lys
1               5                   10                  15

Ala Thr Ala Val Met Pro Asp Gly Gln Phe Lys Asp Ile Ser Leu Ser
            20                  25                  30

Asp Tyr Lys Gly Lys Tyr Val Val Phe Phe Phe Tyr Pro Leu Asp Phe
        35                  40                  45

Thr Phe Val Cys Pro Thr Glu Ile Ile Ala Phe Ser Asp Arg Ala Glu
    50                  55                  60

Glu Phe Lys Lys Leu Asn Cys Gln Val Ile Gly Ala Ser Val Asp Ser
65                  70                  75                  80

His Phe Cys His Leu Ala Trp Val Asn Thr Pro Lys Lys Gln Gly Gly
                85                  90                  95

Leu Gly Pro Met Asn Ile Pro Leu Val Ser Asp Pro Lys Arg Thr Ile
            100                 105                 110

Ala Gln Asp Tyr Gly Val Leu Lys Ala Asp Glu Gly Ile Ser Phe Arg
        115                 120                 125

Gly Leu Phe Ile Ile Asp Asp Lys Gly Ile Leu Arg Gln Ile Thr Val
    130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Gln Lys Ser Lys
            180                 185                 190

Glu Tyr Phe Ser Lys Gln Lys
        195

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
    Synthetic oligonucleotide
<220> FEATURE:
<223> OTHER INFORMATION: Description of Artificial Sequence: Synthetic
    oligonucleotide

<400> SEQUENCE: 9
ggcugaugaa ggcaucucgt t                                          21

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 10
augcuaaaau ugggcaccc                                             19

<210> SEQ ID NO 11

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ugcuaaaauu gggcacccu                                                     19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cuucaaagcc acagcuguu                                                     19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
agccacagcu guuaugcca                                                     19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gccacagcug uuaugccag                                                     19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
agauaucagc cugucugac                                                     19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gauaucagcc ugucugacu                                                     19

<210> SEQ ID NO 17
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gaaacucaac ugccaagug                                                    19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
acucaacugc caagugauu                                                    19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cucaacugcc aagugauug                                                    19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cugccaagug auuggugcu                                                    19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gugauuggug cuucugugg                                                    19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
gaaacaagga ggacuggga                                                    19

<210> SEQ ID NO 23
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 23
cauuccuuug guaucagac                                                    19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
aggcugauga aggcaucuc                                                    19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgcaccauu gcucaggau                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggguauucuu cggcagauc                                                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
accuggcagu gauaccauc                                                    19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
ccuggcagug auaccauca                                                    19

<210> SEQ ID NO 29
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
gccugauguc caaaagagc                                                     19

<210> SEQ ID NO 30
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 30
cuggacuucc agaagaacat t                                                  21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 31
cuuacgcuga guacuucgat t                                                  21

<210> SEQ ID NO 32
<211> LENGTH: 7
<212> TYPE: PRT
<213> ORGANISM: Aplysia punctata

<400> SEQUENCE: 32

Asp Gly Glu Asp Ala Ala Val
 1               5

<210> SEQ ID NO 33
<211> LENGTH: 9
<212> TYPE: PRT
<213> ORGANISM: Aplysia punctata
<220> FEATURE:
<221> NAME/KEY: MOD_RES
<222> LOCATION: (1)
<223> OTHER INFORMATION: Asp or Gln
<220> FEATURE:
<221> NAME/KEY: MOD_RES
<222> LOCATION: (3)
<223> OTHER INFORMATION: Ile or Val
<220> FEATURE:
<221> NAME/KEY: MOD_RES
<222> LOCATION: (7)
<223> OTHER INFORMATION: Gln or Arg
<220> FEATURE:
<221> NAME/KEY: MOD_RES
<222> LOCATION: (9)
<223> OTHER INFORMATION: Gln or Pro

<400> SEQUENCE: 33

Xaa Gly Xaa Cys Arg Asn Xaa Arg Xaa
 1               5
```

```
<210> SEQ ID NO 34
<211> LENGTH: 4
<212> TYPE: PRT
<213> ORGANISM: Aplysia punctata

<400> SEQUENCE: 34

Phe Ala Asp Ser
  1

<210> SEQ ID NO 35
<211> LENGTH: 8
<212> TYPE: PRT
<213> ORGANISM: Aplysia punctata
<220> FEATURE:
<221> NAME/KEY: MOD_RES
<222> LOCATION: (5)
<223> OTHER INFORMATION: Ile or Leu

<400> SEQUENCE: 35

Gly Pro Asp Gly Xaa Val Ala Asp
  1               5

<210> SEQ ID NO 36
<211> LENGTH: 7
<212> TYPE: PRT
<213> ORGANISM: Aplysia punctata
<220> FEATURE:
<221> NAME/KEY: MOD_RES
<222> LOCATION: (6)
<223> OTHER INFORMATION: Lys or Gln
<220> FEATURE:
<221> NAME/KEY: MOD_RES
<222> LOCATION: (7)
<223> OTHER INFORMATION: Ile or Leu

<400> SEQUENCE: 36

Pro Gly Glu Val Ser Xaa Xaa
  1               5

<210> SEQ ID NO 37
<211> LENGTH: 15
<212> TYPE: PRT
<213> ORGANISM: Aplysia punctata

<400> SEQUENCE: 37

Ala Thr Gln Ala Tyr Ala Ala Val Arg Pro Ile Pro Ala Ser Lys
  1               5                   10                  15

<210> SEQ ID NO 38
<211> LENGTH: 13
<212> TYPE: PRT
<213> ORGANISM: Aplysia punctata

<400> SEQUENCE: 38

Asp Ser Gly Leu Asp Ile Ala Val Glu Tyr Ser Asp Arg
  1               5                   10

<210> SEQ ID NO 39
<211> LENGTH: 12
<212> TYPE: PRT
<213> ORGANISM: Aplysia punctata

<400> SEQUENCE: 39

Gly Asp Val Pro Tyr Asp Leu Ser Pro Glu Glu Lys
  1               5                   10

<210> SEQ ID NO 40
```

```
<211> LENGTH: 442
<212> TYPE: DNA
<213> ORGANISM: Aplysia punctata

<400> SEQUENCE: 40
caagacgggg aagacaagga gtttgacgga gaaatcgtca gcgtcagagt gctgaaggcg      60
ttcggcaagc ctggctacgg ttacaagcag ccctcgtgca aggaaggcaa ggactacgtg     120
agcagcggca gcgttcttca cgtgctgcag tgtgccggct tcttcgaggt gtgctacgag     180
gagaggatca ccacccagcc agccacgact gtcgctgcag cagaggtaca atgcaaaaag     240
ttcatcgcaa cccacaaatt ggaggagact gttgatggaa ggatcgtcag catcgagctt     300
gtccagagac tgaagaaaca atccggatac ggtccaagtg gcggttctgg ttatggcaac     360
ggtcatggtc aaagacccgg ttacggatac ggttctggta gtggaagtgg ctacgccccc     420
agaggaggat acaacccaaa ag                                              442

<210> SEQ ID NO 41
<211> LENGTH: 147
<212> TYPE: PRT
<213> ORGANISM: Aplysia punctata

<400> SEQUENCE: 41

Gln Asp Gly Glu Asp Lys Glu Phe Asp Gly Glu Ile Val Ser Val Arg
  1               5                  10                  15

Val Leu Lys Ala Phe Gly Lys Pro Gly Tyr Gly Tyr Lys Gln Pro Ser
             20                  25                  30

Cys Lys Glu Gly Lys Asp Tyr Val Ser Ser Gly Ser Val Leu His Val
         35                  40                  45

Leu Gln Cys Ala Gly Phe Phe Glu Val Cys Tyr Glu Glu Arg Ile Thr
     50                  55                  60

Thr Gln Pro Ala Thr Thr Val Ala Ala Ala Glu Val Gln Cys Lys Lys
 65                  70                  75                  80

Phe Ile Ala Thr His Lys Leu Glu Glu Thr Val Asp Gly Arg Ile Val
                 85                  90                  95

Ser Ile Glu Leu Val Gln Arg Leu Lys Lys Gln Ser Gly Tyr Gly Pro
            100                 105                 110

Ser Gly Gly Ser Gly Tyr Gly Asn Gly His Gly Gln Arg Pro Gly Tyr
        115                 120                 125

Gly Tyr Gly Ser Gly Ser Gly Ser Gly Tyr Ala Pro Arg Gly Gly Tyr
    130                 135                 140

Asn Pro Lys
145

<210> SEQ ID NO 42
<211> LENGTH: 462
<212> TYPE: DNA
<213> ORGANISM: Aplysia punctata
<220> FEATURE:
<221> NAME/KEY: modified_base
<222> LOCATION: (20)
<223> OTHER INFORMATION: a, c, g, t, unknown or other
<220> FEATURE:
<221> NAME/KEY: modified_base
<222> LOCATION: (22)
<223> OTHER INFORMATION: a, c, g, t, unknown or other
<220> FEATURE:
<221> NAME/KEY: modified_base
<222> LOCATION: (58)
<223> OTHER INFORMATION: a, c, g, t, unknown or other
<220> FEATURE:
<221> NAME/KEY: modified_base
```

```
<222> LOCATION: (73)
<223> OTHER INFORMATION: a, c, g, t, unknown or other
<220> FEATURE:
<221> NAME/KEY: modified_base
<222> LOCATION: (132)
<223> OTHER INFORMATION: a, c, g, t, unknown or other
<220> FEATURE:
<221> NAME/KEY: modified_base
<222> LOCATION: (150)
<223> OTHER INFORMATION: a, c, g, t, unknown or other
<220> FEATURE:
<221> NAME/KEY: modified_base
<222> LOCATION: (182)
<223> OTHER INFORMATION: a, c, g, t, unknown or other
<220> FEATURE:
<221> NAME/KEY: modified_base
<222> LOCATION: (220)
<223> OTHER INFORMATION: a, c, g, t, unknown or other
<220> FEATURE:
<221> NAME/KEY: modified_base
<222> LOCATION: (254)
<223> OTHER INFORMATION: a, c, g, t, unknown or other
<220> FEATURE:
<221> NAME/KEY: modified_base
<222> LOCATION: (317)
<223> OTHER INFORMATION: a, c, g, t, unknown or other
<220> FEATURE:
<221> NAME/KEY: modified_base
<222> LOCATION: (338)
<223> OTHER INFORMATION: a, c, g, t, unknown or other

<400> SEQUENCE: 42
taccgccccc gccaccactn tngcaccagc agaaccaacc tgcgagaagc tgtccgtntg    60
gttcaacgtg ganaagaaat tcgaaggttc cagaatcgtg agtttcaagc tcatccgcct   120
gttcaacagg tncaagaagt gcaagaaagn ccagtattcc gtgtctggcg atgatgagga   180
cncattcgtt gtcagtggtt gttctggcgt gttccaggtn tgctacgaag aacaaacggc   240
gcccgctaca accnccacag aagccccgaa gccagagcca agaagaccca agaggaaaaa   300
tttcccaatc aaatttngta aacactgatg ggttaatntg acgaccagtg cgtctgcgaa   360
agaatcatgt tatggttcat gatgtcatgc tcttaatata ggttgtaacg tttaacgcga   420
tacagacatt aaaactcatt gttcaaaaaa aaaaaaaaaa aa                      462

<210> SEQ ID NO 43
<211> LENGTH: 155
<212> TYPE: PRT
<213> ORGANISM: Aplysia punctata
<220> FEATURE:
<221> NAME/KEY: MOD_RES
<222> LOCATION: (7)..(8)
<223> OTHER INFORMATION: variable amino acid
<220> FEATURE:
<221> NAME/KEY: MOD_RES
<222> LOCATION: (20)
<223> OTHER INFORMATION: variable amino acid
<220> FEATURE:
<221> NAME/KEY: MOD_RES
<222> LOCATION: (25)
<223> OTHER INFORMATION: variable amino acid
<220> FEATURE:
<221> NAME/KEY: MOD_RES
<222> LOCATION: (44)
<223> OTHER INFORMATION: variable amino acid
<220> FEATURE:
<221> NAME/KEY: MOD_RES
<222> LOCATION: (50)
<223> OTHER INFORMATION: variable amino acid
<220> FEATURE:
<221> NAME/KEY: MOD_RES
<222> LOCATION: (58)..(59)
<223> OTHER INFORMATION: variable amino acid
<220> FEATURE:
```

```
<221> NAME/KEY: MOD_RES
<222> LOCATION: (61)
<223> OTHER INFORMATION: variable amino acid
<220> FEATURE:
<221> NAME/KEY: MOD_RES
<222> LOCATION: (74)
<223> OTHER INFORMATION: variable amino acid
<220> FEATURE:
<221> NAME/KEY: MOD_RES
<222> LOCATION: (85)
<223> OTHER INFORMATION: variable amino acid
<220> FEATURE:
<221> NAME/KEY: MOD_RES
<222> LOCATION: (106)..(107)
<223> OTHER INFORMATION: variable amino acid
<220> FEATURE:
<221> NAME/KEY: MOD_RES
<222> LOCATION: (112)..(113)
<223> OTHER INFORMATION: variable amino acid
<220> FEATURE:
<221> NAME/KEY: MOD_RES
<222> LOCATION: (132)..(133)
<223> OTHER INFORMATION: variable amino acid
<220> FEATURE:
<221> NAME/KEY: MOD_RES
<222> LOCATION: (137)
<223> OTHER INFORMATION: variable amino acid
<220> FEATURE:
<221> NAME/KEY: MOD_RES
<222> LOCATION: (145)
<223> OTHER INFORMATION: variable amino acid

<400> SEQUENCE: 43

Tyr Arg Pro Arg His His Xaa Xaa Thr Ser Arg Thr Asn Leu Arg Glu
 1               5                  10                  15

Ala Val Arg Xaa Val Gln Arg Gly Xaa Glu Ile Arg Arg Phe Gln Asn
            20                  25                  30

Arg Glu Phe Gln Ala His Pro Pro Val Gln Gln Xaa Gln Glu Val Gln
        35                  40                  45

Glu Xaa Pro Val Phe Arg Val Trp Arg Xaa Xaa Gly Xaa Ile Arg Cys
    50                  55                  60

Gln Trp Leu Phe Trp Arg Val Pro Gly Xaa Leu Arg Arg Thr Asn Gly
65                  70                  75                  80

Ala Arg Tyr Asn Xaa His Arg Ser Pro Glu Ala Arg Ala Lys Lys Thr
                85                  90                  95

Gln Glu Glu Lys Phe Pro Asn Gln Ile Xaa Xaa Thr Leu Met Gly Xaa
            100                 105                 110

Xaa Asp Asp Gln Cys Val Cys Glu Arg Ile Met Leu Trp Phe Met Met
        115                 120                 125

Ser Cys Ser Xaa Xaa Tyr Arg Leu Xaa Arg Leu Thr Arg Tyr Arg His
    130                 135                 140

Xaa Asn Ser Leu Phe Lys Lys Lys Lys Lys
145                 150                 155

<210> SEQ ID NO 44
<211> LENGTH: 153
<212> TYPE: PRT
<213> ORGANISM: Aplysia punctata
<220> FEATURE:
<221> NAME/KEY: MOD_RES
<222> LOCATION: (7)
<223> OTHER INFORMATION: variable amino acid
<220> FEATURE:
<221> NAME/KEY: MOD_RES
<222> LOCATION: (19)
<223> OTHER INFORMATION: variable amino acid
<220> FEATURE:
<221> NAME/KEY: MOD_RES
```

```
<222> LOCATION: (24)
<223> OTHER INFORMATION: variable amino acid
<220> FEATURE:
<221> NAME/KEY: MOD_RES
<222> LOCATION: (44)
<223> OTHER INFORMATION: variable amino acid
<220> FEATURE:
<221> NAME/KEY: MOD_RES
<222> LOCATION: (50)
<223> OTHER INFORMATION: variable amino acid
<220> FEATURE:
<221> NAME/KEY: MOD_RES
<222> LOCATION: (61)
<223> OTHER INFORMATION: variable amino acid
<220> FEATURE:
<221> NAME/KEY: MOD_RES
<222> LOCATION: (73)
<223> OTHER INFORMATION: variable amino acid
<220> FEATURE:
<221> NAME/KEY: MOD_RES
<222> LOCATION: (85)
<223> OTHER INFORMATION: variable amino acid
<220> FEATURE:
<221> NAME/KEY: MOD_RES
<222> LOCATION: (106)
<223> OTHER INFORMATION: variable amino acid
<220> FEATURE:
<221> NAME/KEY: MOD_RES
<222> LOCATION: (109)
<223> OTHER INFORMATION: variable amino acid
<220> FEATURE:
<221> NAME/KEY: MOD_RES
<222> LOCATION: (113)
<223> OTHER INFORMATION: variable amino acid
<220> FEATURE:
<221> NAME/KEY: MOD_RES
<222> LOCATION: (127)
<223> OTHER INFORMATION: variable amino acid
<220> FEATURE:
<221> NAME/KEY: MOD_RES
<222> LOCATION: (138)
<223> OTHER INFORMATION: variable amino acid

<400> SEQUENCE: 44

Thr Ala Pro Ala Thr Thr Xaa Ala Pro Ala Glu Pro Thr Cys Glu Lys
  1               5                  10                  15

Leu Ser Xaa Trp Phe Asn Val Xaa Lys Lys Phe Glu Gly Ser Arg Ile
             20                  25                  30

Val Ser Phe Lys Leu Ile Arg Leu Phe Asn Arg Xaa Lys Lys Cys Lys
         35                  40                  45

Lys Xaa Gln Tyr Ser Val Ser Gly Asp Asp Glu Asp Xaa Phe Val Val
     50                  55                  60

Ser Gly Cys Ser Gly Val Phe Gln Xaa Cys Tyr Glu Glu Gln Thr Ala
 65                  70                  75                  80

Pro Ala Thr Thr Xaa Thr Glu Ala Pro Lys Pro Glu Pro Arg Arg Pro
                 85                  90                  95

Lys Arg Lys Asn Phe Pro Ile Lys Phe Xaa Lys His Xaa Trp Val Asn
            100                 105                 110

Xaa Thr Thr Ser Ala Ser Ala Lys Glu Ser Cys Tyr Gly Ser Xaa Cys
        115                 120                 125

His Ala Leu Asn Ile Gly Cys Asn Val Xaa Arg Asp Thr Asp Ile Lys
    130                 135                 140

Thr His Cys Ser Lys Lys Lys Lys
145                 150

<210> SEQ ID NO 45
<211> LENGTH: 153
<212> TYPE: PRT
```

```
<213> ORGANISM: Aplysia punctata
<220> FEATURE:
<221> NAME/KEY: MOD_RES
<222> LOCATION: (6)..(7)
<223> OTHER INFORMATION: variable amino acid
<220> FEATURE:
<221> NAME/KEY: MOD_RES
<222> LOCATION: (19)
<223> OTHER INFORMATION: variable amino acid
<220> FEATURE:
<221> NAME/KEY: MOD_RES
<222> LOCATION: (24)
<223> OTHER INFORMATION: variable amino acid
<220> FEATURE:
<221> NAME/KEY: MOD_RES
<222> LOCATION: (33)
<223> OTHER INFORMATION: variable amino acid
<220> FEATURE:
<221> NAME/KEY: MOD_RES
<222> LOCATION: (44)
<223> OTHER INFORMATION: variable amino acid
<220> FEATURE:
<221> NAME/KEY: MOD_RES
<222> LOCATION: (50)
<223> OTHER INFORMATION: variable amino acid
<220> FEATURE:
<221> NAME/KEY: MOD_RES
<222> LOCATION: (60)
<223> OTHER INFORMATION: variable amino acid
<220> FEATURE:
<221> NAME/KEY: MOD_RES
<222> LOCATION: (73)
<223> OTHER INFORMATION: variable amino acid
<220> FEATURE:
<221> NAME/KEY: MOD_RES
<222> LOCATION: (84)
<223> OTHER INFORMATION: variable amino acid
<220> FEATURE:
<221> NAME/KEY: MOD_RES
<222> LOCATION: (105)
<223> OTHER INFORMATION: variable amino acid
<220> FEATURE:
<221> NAME/KEY: MOD_RES
<222> LOCATION: (112)..(113)
<223> OTHER INFORMATION: variable amino acid
<220> FEATURE:
<221> NAME/KEY: MOD_RES
<222> LOCATION: (133)
<223> OTHER INFORMATION: variable amino acid

<400> SEQUENCE: 45

Pro Pro Pro Pro Pro Xaa Xaa His Gln Gln Asn Gln Pro Ala Arg Ser
 1               5                  10                  15

Cys Pro Xaa Gly Ser Thr Trp Xaa Arg Asn Ser Lys Val Pro Glu Ser
            20                  25                  30

Xaa Val Ser Ser Ser Ala Cys Ser Thr Gly Xaa Arg Ser Ala Arg
        35                  40                  45

Lys Xaa Ser Ile Pro Cys Leu Ala Met Met Arg Xaa His Ser Leu Ser
 50                  55                  60

Val Val Val Leu Ala Cys Ser Arg Xaa Ala Thr Lys Asn Lys Arg Arg
 65                  70                  75                  80

Pro Leu Gln Xaa Pro Gln Lys Pro Arg Ser Gln Ser Gln Glu Asp Pro
                85                  90                  95

Arg Gly Lys Ile Ser Gln Ser Asn Xaa Val Asn Thr Asp Gly Leu Xaa
            100                 105                 110

Xaa Arg Pro Val Arg Leu Arg Lys Asn His Val Met Val His Asp Val
        115                 120                 125

Met Leu Leu Ile Xaa Val Val Thr Phe Asn Ala Ile Gln Thr Leu Lys
130                 135                 140
```

Leu Ile Val Gln Lys Lys Lys Lys Lys
145                 150

<210> SEQ ID NO 46
<211> LENGTH: 9
<212> TYPE: PRT
<213> ORGANISM: Aplysia punctata
<220> FEATURE:
<221> NAME/KEY: MOD_RES
<222> LOCATION: (3)
<223> OTHER INFORMATION: Ile or Val

<400> SEQUENCE: 46

Asp Gly Xaa Cys Arg Asn Arg Arg Gln
1               5

<210> SEQ ID NO 47
<211> LENGTH: 14
<212> TYPE: PRT
<213> ORGANISM: Aplysia punctata

<400> SEQUENCE: 47

Asp Ser Gly Leu Asp Ile Ala Val Phe Glu Tyr Ser Asp Arg
1               5                   10

<210> SEQ ID NO 48
<211> LENGTH: 7
<212> TYPE: PRT
<213> ORGANISM: Aplysia punctata

<400> SEQUENCE: 48

Val Phe Glu Tyr Ser Asp Arg
1               5

<210> SEQ ID NO 49
<211> LENGTH: 16
<212> TYPE: PRT
<213> ORGANISM: Aplysia punctata
<220> FEATURE:
<221> NAME/KEY: MOD_RES
<222> LOCATION: (3)
<223> OTHER INFORMATION: variable amino acid

<400> SEQUENCE: 49

Leu Phe Xaa Tyr Gln Leu Pro Asn Thr Pro Asp Val Asn Leu Glu Ile
1               5                   10                  15

<210> SEQ ID NO 50
<211> LENGTH: 10
<212> TYPE: PRT
<213> ORGANISM: Aplysia punctata

<400> SEQUENCE: 50

Val Ile Ser Glu Leu Gly Leu Thr Pro Lys
1               5                   10

<210> SEQ ID NO 51
<211> LENGTH: 11
<212> TYPE: PRT
<213> ORGANISM: Aplysia punctata
<220> FEATURE:
<221> NAME/KEY: MOD_RES
<222> LOCATION: (5)
<223> OTHER INFORMATION: variable amino acid

<400> SEQUENCE: 51

Val Ile Leu Ala Xaa Pro Val Tyr Ala Leu Asn

<210> SEQ ID NO 52
<211> LENGTH: 8
<212> TYPE: PRT
<213> ORGANISM: Aplysia punctata

<400> SEQUENCE: 52

Val Phe Met Thr Phe Asp Gln Pro
1               5

<210> SEQ ID NO 53
<211> LENGTH: 10
<212> TYPE: PRT
<213> ORGANISM: Aplysia punctata

<400> SEQUENCE: 53

Ser Asp Ala Leu Phe Phe Gln Met Tyr Asp
1               5                   10

<210> SEQ ID NO 54
<211> LENGTH: 18
<212> TYPE: PRT
<213> ORGANISM: Aplysia punctata

<400> SEQUENCE: 54

Ser Glu Ala Ser Gly Asp Tyr Ile Leu Ile Ala Ser Tyr Ala Asp Gly
1               5                   10                  15

Leu Lys

<210> SEQ ID NO 55
<211> LENGTH: 21
<212> TYPE: PRT
<213> ORGANISM: Aplysia punctata

<400> SEQUENCE: 55

Asn Gln Gly Glu Asp Ile Pro Gly Ser Asp Pro Gln Tyr Asn Gln Val
1               5                   10                  15

Thr Glu Pro Leu Lys
            20

<210> SEQ ID NO 56
<211> LENGTH: 28
<212> TYPE: PRT
<213> ORGANISM: Aplysia punctata

<400> SEQUENCE: 56

Val Ala Val Val Gly Ala Gly Pro Gly Gly Ala Asn Ser Ala Tyr Met
1               5                   10                  15

Leu Arg Asp Ser Gly Leu Asp Ile Ala Val Phe Glu
            20                  25

<210> SEQ ID NO 57
<211> LENGTH: 8
<212> TYPE: PRT
<213> ORGANISM: Aplysia punctata

<400> SEQUENCE: 57

Arg Val Gly Gly Arg Leu Phe Thr
1               5

<210> SEQ ID NO 58
<211> LENGTH: 45

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tcctaacgta ggtctagacc tgttgcattt ttttttttttt ttttt                    45

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)
<223> OTHER INFORMATION: a, c, g, t, unknown or other

<400> SEQUENCE: 59
tcgtgttcga rtactcngay cg                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgtaggtct agacctgttg ca                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ccgtgtagat ctcactgcca ta                                              22

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccgttgagtt gtagacct                                                   18

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)
<223> OTHER INFORMATION: inosine
<220> FEATURE:
```

```
<221> NAME/KEY: modified_base
<222> LOCATION: (25)
<223> OTHER INFORMATION: inosine
<220> FEATURE:
<221> NAME/KEY: modified_base
<222> LOCATION: (29)
<223> OTHER INFORMATION: inosine
<220> FEATURE:
<221> NAME/KEY: modified_base
<222> LOCATION: (30)
<223> OTHER INFORMATION: inosine
<220> FEATURE:
<221> NAME/KEY: modified_base
<222> LOCATION: (34)
<223> OTHER INFORMATION: inosine
<220> FEATURE:
<221> NAME/KEY: modified_base
<222> LOCATION: (35)
<223> OTHER INFORMATION: inosine

<400> SEQUENCE: 63
ggccacgcgt cgactagtac gggnngggnn gggnng                                  36

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
aattggccac gcgtcgacta gtac                                               24

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aattctcgtc tgctgtgctt ctcct                                              25

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gacttagagg aagtagtcgt tga                                                23

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctgttatgcc agatggtcag                                                    20

<210> SEQ ID NO 68
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gataccaaag gaatgttcat g                                             21

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
caagaaggag ggtgacctga                                               20

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttcgttgaag tcctactcta cg                                            22

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ggtatcgtgg aaggactcat gac                                           23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gacttgccct tcgagtgacc gta                                           23

<210> SEQ ID NO 73
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
cgagaugccu ucaucagcct t                                             21
```

```
<210> SEQ ID NO 74
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
uguucuucug gaaguccagt t                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 75
ucgaaguacu cagcguaagt t                                              21

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (7)
<223> OTHER INFORMATION: variable amino acid
<220> FEATURE:
<221> NAME/KEY: MOD_RES
<222> LOCATION: (8)
<223> OTHER INFORMATION: Thr or Ser

<400> SEQUENCE: 76

Arg His Gly Gly Arg His Xaa Xaa
 1               5

<210> SEQ ID NO 77
<211> LENGTH: 13
<212> TYPE: PRT
<213> ORGANISM: Aplysia punctata
<220> FEATURE:
<221> NAME/KEY: MOD_RES
<222> LOCATION: (1)
<223> OTHER INFORMATION: variable amino acid

<400> SEQUENCE: 77

Xaa Gly Asp Val Pro Tyr Asp Leu Ser Pro Glu Glu Lys
 1               5                  10

<210> SEQ ID NO 78
<211> LENGTH: 88
<212> TYPE: PRT
<213> ORGANISM: Aplysia punctata
<220> FEATURE:
<221> NAME/KEY: MOD_RES
<222> LOCATION: (21)..(22)
<223> OTHER INFORMATION: variable amino acid
<220> FEATURE:
<221> NAME/KEY: MOD_RES
```

```
<222> LOCATION: (52)
<223> OTHER INFORMATION: variable amino acid
<220> FEATURE:
<221> NAME/KEY: MOD_RES
<222> LOCATION: (60)
<223> OTHER INFORMATION: variable amino acid
<220> FEATURE:
<221> NAME/KEY: MOD_RES
<222> LOCATION: (69)
<223> OTHER INFORMATION: variable amino acid
<220> FEATURE:
<221> NAME/KEY: MOD_RES
<222> LOCATION: (77)
<223> OTHER INFORMATION: variable amino acid

<400> SEQUENCE: 78

Met Ser Ser Ala Val Leu Leu Leu Ala Cys Ala Leu Val Ile Ser Val
 1               5                  10                  15

His Ala Asp Gly Xaa Xaa Arg Asn Arg Arg Gln Cys Asn Arg Glu Val
            20                  25                  30

Cys Gly Ser Thr Tyr Asp Val Ala Val Val Gly Ala Gly Pro Gly Gly
         35                  40                  45

Ala Asn Ser Xaa Tyr Met Leu Arg Asp Ser Gly Xaa Asp Ile Ala Val
     50                  55                  60

Phe Glu Tyr Ser Xaa Arg Val Gly Gly Arg Leu Phe Xaa Tyr Gln Leu
 65                  70                  75                  80

Pro Asn Thr Pro Asp Val Asn Leu
             85
```

L-AMINO ACID OXIDASE WITH CYTOTOXIC ACTIVITY FROM *APLYSIA PUNCTATA*

This application is a divisional application of U.S. application Ser. No. 10/542,769, filed on Mar. 6, 2006 now U.S. Pat. No. 7,407,784, which was the National Stage application under §371 of PCT/EP04/00423, filed Jan. 20, 2004.

DESCRIPTION

The present invention relates to a cytotoxic polypeptide which is an L-amino acid oxidase isolated from the ink of the sea hare *Aplysia punctata*.

The sea hare *Aplysia* produces a pink-coloured ink, which has cytotoxic activity towards several eukaryotic cell lines. WO97/16457 discloses a partial sequence from an *Aplysia* protein, which allegedly has anti-tumor activity. Cyplasin L (558 aa, NCBI accession number 11967690) and cyplasin S (421 aa, 11967688; Petzelt and Werner, 2001, Cell Biology International, 25(2):A23) both include parts of sequences disclosed in WO 97/16457. Cyplasin S exhibits 95% sequence identity to cyplasin L. Cyplasin L is produced in the nidamental gland but neither in the ink gland (including the mantle region) nor in the opaline gland of *Aplysia punctata*. Thus, it is concluded that cyplasin is not a component of *Aplysia* ink and is not responsible for the cytotoxic activity of the *Aplysia* ink. A detailed description of *Aplysia* anatomy and a dissection guide can be found in the internet in Richard Fox, Invertebrate anatomy (1994, available via the world wide web at science.lander.edu/rsfox/).

The overall aim in tumor therapy is the selective eradication of transformed cells without harming healthy cells. Several glycoproteins isolated from sea hares (*Aplysia* species) have attracted attention because of their anti-tumor activity, e.g. aplysianin A from *Aplysia kurodai*, or cyplasins. The underlying mechanism for such activity has however not been elucidated so far. Recombinant intracellular cyplasins seem to be non-toxic, whereas the extracellular cyplasin is cytotoxic (Petzelt et al., Neoplasia, 4:49-59, 2002).

WO 03/057726 discloses a cyplasin which is devoid of a functional secretory signal sequence. Since cyplasin only causes eukaryotic cell death from outside, the cyplasin of WO 03/057726 can thus be functionally expressed in eukaryotic cells without killing these cells. When acting from outside, cyplasin induced cell death is accompanied by fast depolymerization of the actin filaments. Expression of bioactive cyplasin S and L in prokaryotic host cells is not possible.

WO 02/31144 discloses a further cytotoxic factor isolated from the ink of *Aplysia punctata*. Fragments of the amino acid sequence of the factor are disclosed. No data were presented demonstrating that this factor has any oxidase function or has any properties related to an oxidase.

At least two main phenotypes of cell death are described: apoptosis, a genetically fixed physiological form of cell death, is accompanied by shrinkage, membrane blebbing, nuclear fragmentation, and final disintegration into so-called apoptotic bodies. In contrast, necrosis is a pathological process characterized by membrane disruption and cell swelling. Cell death induced by reactive oxygen and nitrogen species (ROS/NOS) might lead to apoptosis and necrosis but also to other forms of cell death, which cannot be clearly assigned to one of these main forms of cell death.

The cytotoxic factors derived from the sea hares so far have several disadvantages which might hamper its application. The biological function and the nature of the cytotoxic activity, which are prerequisites for the development of a lead compound, are not known so far. Aplysianin A contains a dinucleotide binding fold and the so-called "GG motif" which are found in many flavoproteins. The GG motif has also been described in cyplasins (Petzelt et al., supra). Based on this knowledge, the factors can be applied in its entirety only, because the domains relevant for proper function and cellular receptors are unknown. The administration of an entire non-self protein to an animal or a human might cause severe immunologic complications.

The dinucleotide binding fold and the GG motif are found e.g. within the N-terminal domain of FAD containing enzymes (e.g. reductases, dehydrogenases, hydroxylases, peroxidases, and oxidases). FAD containing enzymes can be classified into five groups GR1, GR2, FR, PCMH, and PO according to the sequences of their FAD binding domains and additional conserved sequence motifs (Dym and Eisenberg, Protein Science, 10:1712-1728, 2001). The consensus sequence of GR1 and GR2 is GxGxxG. The GG motif RhG-GRhxxT/S (SEQ ID NO: 76) is commonly found in oxidases, e.g. L-amino acid oxidases, monoamino oxidases, polyamine oxidases, and putrescine oxidases, wherein x describes any amino acid, and h describes a hydrophobic amino acid.

L-amino acid oxidases catalyse the formation of $H_2O_2$, ammonia, and an alpha keto acid from an amino acid in the presence of oxygen and $H_2O$ (Geyer et al, 2001, Eur. J. Biochem. 268, 4044-4053). An L-lysine alpha oxidase (EC 1.4.3.14) for instance can be obtained from the fungus *Trichoderma* spec. (Kusakabe et al., J. Biol. Chem. 10:976-981, 1980) which shows antimetastatic effects (Umanskii et al., Biull Eksp Biol Med. 109:458-9, 1990, Khaduev et al., Biull Eksp Biol Med. 112:419-22, 1991). The *Trichoderma* L-lysine oxidase is a dimer with a molecular weight of 112-119 kDa. A further L-lysine oxidase obtained from the fish Chub mackerel is a dimer and has a molecular weight of 135 kDa Jung et al., J. Immunol. 165:1491-1497, 2000) and induces apoptosis. Apoxin is an L-leucin oxidase from the rattlesnake (*Crotalus atrox*) venom which induces apoptosis in tumor cells and vascular endothelial cells in vitro (Torii et al., J. Biol. Chem. 272:9539-9542, 1997). A cytotoxic L-lysine alpha oxidase is described in the art which penetrates into Jurkat cells and there activates oxidative deamination of L-lysine and correspondingly the peroxide formation. Conjugates of the enzyme with monoclonal antibodies against the CD5 receptor cannot penetrate into the cells and are assumed to produce toxic $H_2O_2$ outside the cells. The conjugates have a reduced cytotoxic effect, although the effect of conjugation upon enzymatic activity is negligible (Zhukova et al., Vopr Med Khim 2001, 47:588-592). Another L-lysine oxidase obtained from the snail *Achatina fulica* and producing $H_2O_2$ is found to have an antimicrobial effect. This oxidase might be useful as an agent against pathogenic bacteria (Ehare et al., 2002, FEBS Letters, 531:509-512).

Most known alpha amino acid oxidases which produce $H_2O_2$ possess a broad substrate specificity. The L-lysine alpha oxidase from *Trichoderma viride* (EC 1.4.3.14, Kusakabe et al., supra) is specific for lysine, but also oxidizes L-ornithine, L-phenylalanine, L-tyrosine, L-arginine, and L-histidine to a lesser extent. The L-lysine oxidase of Chub mackerel (EMBL, AJ400781; Jung et al., supra) is specific for lysine and in addition transforms arginine, histidin, leucine, methionine, phenylalanine, and ornithine (specificity 40 fold reduced). Even if these enzymes could be cytotoxic due to their ability to produce $H_2O_2$, a therapeutic use is hampered because substrates of these enzymes are available in the body fluid in amounts sufficient to release $H_2O_2$ everywhere in the body. Under these conditions, possible negative side effects of $H_2O_2$ are difficult to eliminate.

In addition to $H_2O_2$ producing enzymes, cells possess a detoxification system which eliminates reactive oxygen species (ROS), in particular $H_2O_2$. An important class of detoxifying peroxidases are peroxiredoxins. Peroxiredoxins comprise a class of highly conserved oxidases. In mammals, six different isoforms are known which catalyze the reduction of peroxides by using reducing equivalents that are provided by thioredoxin or glutathone. During catalysis, peroxiredoxin I (Prx I) is inactivated by oxidation of the active site cysteine to cysteine sulfinic acid, a modification which is reversible upon removal of $H_2O_2$. Previously, overexpression of both Prx I and Prx II has been shown to render cells resistant to $H_2O_2$ induced apoptosis.

The problem underlying the present invention is the provision of a means for selective generation of $H_2O_2$ in target tissues, e.g. in tumor tissues with less toxic side effects upon normal cells. The solution is a cytotoxic polypeptide which can be isolated from the ink of the sea hare *Aplysia punctata* and which is a specific L-lysine and/or L-arginine oxidase producing $H_2O_2$ or a fragment or derivative of said polypeptide. The activity of the enzyme can be modulated be administration of substrate. The enzyme provides a lead structure, and it can be used for target identification.

A first aspect of the present invention is a purified polypeptide which exhibits cytotoxic activity on tumor cells and which comprises the amino acid sequence shown in SEQ ID NO: 2, 4, or 6, or a cytotoxic fragment thereof. These sequences are derived from a cytotoxic 60 kDa protein purified from crude ink of *Aplysia punctata* via anion exchange chromatography and gel filtration (see examples 1 and 4). Thus, the polypeptide or the fragment is termed APIT (*Aplysia punctata* ink toxin). The purity of the fractions can be determined by SDS-PAGE and silver staining.

The cytotoxic activity of APIT or the diluted crude ink can be measured by the reduction of the metabolic activity of eukaryotic cells. A person skilled in the art knows suitable methods and cell lines. For example, the metabolic activity of Jurkat T cells can be measured by the addition of WST-1, which is a tetrazolium salt converted by cellular enzymes of viable cells, e.g. by the mitochondrial dehydrogenase, to a dark red formazan. Therefore, the amount of formazan correlates with cell vitality. Formazan can be determined photometrically at 450 nm. Further, dead eukaryotic cells killed by APIT or the diluted crude ink can be counted by adding propidium iodide (PI) at 1 µg/ml in PBS and subsequent flow cytometer analysis. PI is a DNA binding dye which is taken up by dead cells with permeable membranes.

The cytotoxic activity of APIT is reduced by at least 70% after 10 min incubation at 60° C. At 70° C., the activity is almost absent, whereas 0° C. to 50° C. have no effect upon the activity. APIT shows a loss of activity with decrease of pH, with complete inactivation after 10 min pre-incubation at pH 3. After 30 min treatment with 6 M urea, the activity of APIT is almost unaffected. At 8M urea, the activity is reduced by about 50% (example 3).

Tumor cells treated with APIT displays a morphology which is neither typical for apoptosis nor for necrosis but rather is typical for oxidative damage induced cell death. Shrunken nuclei and lack of cell swelling are apoptotic, and early membrane permeabilization is a necrotic characteristic (example 2). The phenotype induced by APIT could be reproduced in Jurkat cells by treatment of the cells with concentrations of $H_2O_2$ >200 µM, indicating that $H_2O_2$ is the active compound in APIT cytotoxic effect. $H_2O_2$ concentrations <100 µM induced apoptosis in Jurkat cells. In contrast to the mode of action of cyplasins, a depolymerization of the active filaments cannot be observed in APIT induced cell death, indicating that the mechanism of APIT action is distinct from that of cyplasins (Example 12).

By depriving possible substrates which can be converted into $H_2O_2$ from the culture medium of the tumor cells, it can be demonstrated that no further toxic effect of APIT upon tumor cells is present. Deprivation of L-lysine and L-arginine from the medium prevents cell death completely. This phenomenon can be observed within a period of 6 to 8 hours during cultivation of tumor cells. In a detailed analysis of the enzymatic activity of APIT, media containing single amino acids (20 L-amino acids, D-lysine) confirmed that L-lysine and/or L-arginine is converted into $H_2O_2$ and the respective alpha keto acid to the same extent, whereas no conversion could be measured with any other of the remaining 18 L-amino acids and D-lysine (example 7). The production of $H_2O_2$ is independent of the presence of cells, however, the presence of cells reduces the amount of free $H_2O_2$, which might be due to detoxification of the medium by the cells. Catalase (a $H_2O_2$ hydrolyzing enzyme) prevents tumor cell death induced by purified APIT and by crude ink as well, confirming the conclusion that $H_2O_2$ is responsible for the ink mediated killing of tumor cells (example 6).

Anti-tumor activity also appears after long-term in vitro treatment (>18 hours) of tumor cells by the cytotoxic factor isolated from the ink of *Aplysia punctata* in combination with an $H_2O_2$ consuming factor, like catalase. In comparison to tumor treatment with the cytotoxic factor from *Aplysia punctata* alone, this alternative tumor treatment takes a much longer time to become effective. The interplay of both enzyme activities continuously reduces L-lysine and L-arginine in the medium which are essential for the living of tumor cells. The tumor cells die as a result.

In summary, the data demonstrate that the polypeptide of SEQ ID NO: 2, 4, or 6 (APIT) is an oxidase which is capable to produce $H_2O_2$. Particularly, the polypeptide is an alpha amino acid oxidase. More particularly, the polypeptide specifically converts L-lysine and/or L-arginine in the presence of $O_2$ and $H_2O$ into an alpha keto acid, ammonia, and $H_2O_2$. Thus, the polypeptide is preferably an L-lysine and/or L-arginine oxidase.

A characteristic feature of the active fractions containing APIT purified from crude ink were two absorption maxima at 390 nm and 470 nm, a hallmark of flavoproteins. A flavine nucleoside, particularly FAD is required as a co-factor for the anti-tumor and oxidase activity of APIT as removal of FAD inactivated APIT (example 5).

Analysis of the sequences SEQ ID NO: 2, 4, and 6 revealed that APIT comprises a sequence similar to known dinucleotide binding folds which are characteristic for flavoproteins (FIG. 4c). The GG-motif (consensus sequence RhGGRhxT/S) (SEQ ID NO: 76) is found adjacent to the dinucleotide binding fold.

A further aspect of the present invention is a polypeptide comprising a fragment of the polypeptides of the sequences of SEQ ID NO: 2, 4, or 6 which can be used as a lead structure for drug development. APIT can be digested by a protease without loss of activity. Digestion leaves the substrate specificity unaltered. Thus, the fragment exhibiting cytotoxic activity is an L-lysine and/or L-arginine oxidase. Preferably, proteinase K is used which is a relative unspecific protease resulting in small fragments. Other proteases which can be selected among specific or unspecific proteases known by a person skilled in the art can be used instead of proteinase K. The cytotoxic proteinase resistant domain of APIT is of particular importance for the development of a non-immunogenic, fully active small compound.

Further preferred fragments comprise partial amino acid sequences of APIT which are obtained by peptide mass fingerprinting, ESI/MS, and Edman degradation:

```
DG(I/V)CRNRRQ,                  (SEQ ID NO: 46)

DSGLDIAVFEYSDR,                 (SEQ ID NO: 47)

VFEYSDR,                        (SEQ ID NO: 48)

LFXYQLPNTPDVNLEI                (SEQ ID NO: 49)
(X = T in SEQ ID NO: 2, 4 and 6),

VISELGLTPK,                     (SEQ ID NO: 50)

GDVPYDLSPEEK,                   (SEQ ID NO: 39)

VILAXPVYALN                     (SEQ ID NO: 51)
(X = M in SEQ ID NO: 2, 4 and 6),

ATQAYAAVRPIPASK,                (SEQ ID NO: 37)

VFMTFDQP,                       (SEQ ID NO: 52)

SDALFFQMYD                      (SEQ ID NO: 53)
(FFQ is FSQ in SEQ ID NO: 2, 4 and 6),

SEASGDYILIASYADGLK,             (SEQ ID NO: 54)

NQGEDIPGSDPQYNQVTEPLK           (SEQ ID NO: 55)
(PQY is PGY in SEQ ID NO: 2, 4 and 6)
```

While not wishing to be bound by theory, the FAD group which is tightly bound to the amino acid chain, e.g. by a covalent bond, might cover possible protease cleavage sites. Thus, protease treatment results in a fragment comprising the active centre of the enzyme, including the prosthetic group FAD. This conclusion is confirmed by the finding that native APIT cannot be cleaved by trypsin, but trypsin can digest denaturated APIT.

Thus, an especially preferred fragment of APIT which is an oxidase exhibiting cytotoxic activity is a sequence comprising the dinucleotide binding fold and the GG motif corresponding to amino acid residues No. 39 to 77 in SEQ ID NO: 2. This sequence is identical to the sequence of amino acid residues No. 38 to 76 in SEQ ID NO: 4 and No. 21 to 59 in SEQ ID NO: 6. More preferably, the fragment has an L-lysine and/or an L-arginine oxidase activity.

Further, the fragment can comprise a stretch of additional amino acid residues which may be selected from SEQ ID NO: 2 or 4 from the sequences adjacent to the residues No. 39 to 77 in SEQ ID NO: 2 or No. 38 to 76 in SEQ ID NO: 4. Preferably, 1-20 additional amino acid can be present at the N-terminus and/or the C-terminus. More preferably, 1-10 additional amino acid can be present at the N-terminus and/or the C-terminus. Most preferably, 1-5 additional amino acid can be present.

A further aspect are polypeptides which are homologous to the polypeptides of SEQ ID NO: 2, 4, or 6, or to fragments thereof, which have an identity of at least 70%, preferably at least 80%, more preferably at least 90%, or most preferably at least 95%. SEQ ID NO: 2, 4, or 6 describe natural variations of APIT by replacements of single amino acids not affecting its function. In further 11 clones, four mutations were found within the sequence comprising the dinucleotide binding fold and the GG motif (Pos. 39 to 77 in SEQ ID NO: 2, see example 4). Taking into account that a fragment obtained by proteolytic digestion is still active as a L-lysine and/or L-arginine oxidase, it can be expected that further modifications of the sequence, e.g. by amino acid substitutions, deletions and/or insertions will not substantially affect the function of APIT.

A modified sequence exhibits an identity of preferably at least 70%, more preferably at least 80% and most preferably at least 90% to a reference sequence, e.g. SEQ ID NO: 2. Preferably, the sequence of Pos. 39 to 77 in SEQ ID NO: 2 has a higher degree of identity to the reference sequence than the total amino acid sequence, e.g. preferably at least 33 of 39 amino acid residues (at least about 85%), more preferably 35 of 39 residues (at least about 90%), and most preferably 37 of 39 residues (at least about 95%).

A still further aspect is a polypeptide of the present invention as described above which is a recombinant polypeptide. The recombinant polypeptide is characterized as being manufactured in a heterologous, i.e. non-*Aplysia* host cell, e.g. in a bacterial cell such as *E. coli* or *Bacillus*, in a yeast cell such as *saccharomyces cerevisiae*, in an insect cell or in a mammalian cell. The recombinant polypeptide has preferably an oxidase, or, more preferably, an L-lysine and/or an L-arginine oxidase activity. Expression of the polypeptide can be done by standard expression systems known by a person skilled in the art. For proper enzymatic function, the prosthetic group FAD may have to be introduced into the polypeptide.

The protein of the invention or a fragment thereof may be in the form of a fusion protein, i.e. fused to heterologous peptide or polypeptide sequences. Preferably fusion proteins are genetic fusions, wherein the nucleic acid sequence encoding a protein or a protein fragment as described above is fused to a nucleic acid sequence encoding a heterologous peptide or polypeptide sequence. The heterologous peptide or polypeptide sequence may be selected from signal sequences, which provide desired processing and/or transport in a host cell. The signal sequence is preferably located at the N- and/or C-terminus of the APIT sequence. Further examples of heterologous sequences are domains which assist expression in host cells and/or purification from cellular extracts or culture media. Still further examples of heterologous sequences are targeting sequences which may direct the APIT polypeptide to a desired target site, e.g. in an organism. Suitable targeting sequences may be e.g. single chain antibodies, which may be directed against tumor specific antigens or proteinaceous ligand sequences, which may be directed against tumor specific receptors.

A further aspect of the present invention is a nucleic acid coding for the polypeptide as described above. The total mRNA of the mantle gland, the nidamental gland, the digestive gland, and the opaline gland can be prepared by standard methods. The mRNA can be reverse transcribed using the tagged oligo dT oligonucleotide (Oligo 1, FIG. 4*b*). The tag is a random sequence not expected to be present within *Aplysia* mRNA to be reverse transcribed. PCR can be performed using the degenerated primer (Oligo 2) derived from the APIT peptide VFEYSDR (SEQ ID NO: 48) and the specific primer (Oligo 3) directed against the tag sequence of the oligo dT primer Oligo 1. The amplified sequence can be cloned into a standard vector and can be sequenced by standard techniques. By this strategy, the 3' terminal sequence of the APIT gene can be obtained. The 5' terminal sequence can be obtained by the RACE strategy. The mRNA from selected tissues (see above) is reverse transcribed using an oligonucleotide derived from the known 3' terminal sequence (e.g. Oligo 4, or Oligo 6) and can be treated with a terminal transferase in the presence of CTP, resulting in a 3'-poly-C-sequence (at the minus strand). PCR can be performed using a tagged primer against the poly-C-sequence (Oligo 5) and a specific primer, e.g. Oligo 4, or Oligo 6. The amplified product can be cloned and sequenced by standard techniques. Finally, for obtaining full-length cDNA clones, specific primers, e.g. Oligo 8 and Oligo 9 can be used. By this strategy, three different clones were obtained and sequenced. The nucleotide sequences are described in SEQ. ID. No. 1, 3, and 5 which are identical to 97% (1560 of 1608) of the nucleotides. 42 of 48 mutations are silent mutations which have no effect upon the amino acid sequence.

By this strategy, further clones of APIT can be obtained which might have a differing sequence. Since more than ten sequences of APIT are known, specific or degenerated primers may be selected from these sequences, and new clones can be obtained by a single PCR of reverse transcribed mRNA. Thus, the nucleic acid encoding a polypeptide as specified above preferably comprises
  (a) a nucleotide sequence as shown in SEQ ID NO: 1, 3, or 5, or at least the polypeptide coding portion thereof, or the complement thereof, or
  (b) a nucleotide sequence corresponding to the sequence of (a) within the scope of degeneracy of the genetic code, or the complement thereof, or
  (c) a nucleotide sequence hybridizing under stringent condition with the sequence of (a) and/or (b), or
  (d) a nucleotide sequence which is homologous to the sequences of (a) and/or (b).

The nucleic acid may be a single stranded or double stranded nucleic acid (DNA or RNA). The nucleic acid is obtainable from natural sources e.g. from *Aplysia* by extraction of RNA, construction of cDNA libraries and screening of the library using degenerated oligonucleotides which were deduced from the peptide sequences described above. The nucleic acid is further obtainable by RT-PCR using RNA extracted from *Aplysia* and oligo-dT-primers or degenerated primers. On the other hand, the nucleic acid is obtainable by chemical synthesis.

Hybridization under stringent conditions preferably means that after washing for 1 h with 1×SSC and 0.1% SDS at 55° C., preferably at 62° C. and more preferably at 68° C., particularly after washing for 1 h with 0.2×SSC and 0.1% SDS at 55° C., preferably at 62° C. and more preferably at 68° C., a hybridization signal is detected.

The degree of identity of the nucleic acid is at least 70%, preferably at least 80%, more preferably at least 90%, and most preferably at least 95% to a reference sequence, e.g. SEQ ID NO: 1, 3 or 5.

Further, the nucleic acid encoding a cytotoxic polypeptide can comprise a partial sequence of the nucleotide sequence as disclosed in SEQ ID NO: 1, 3, or 5. Preferably, the partial sequence is selected from nucleotide No. 115 to 231 in SEQ ID NO: 1, or nucleotide No. 112 to 228 in SEQ ID NO: 3, or nucleic acid residue No. 61 to 177 in SEQ ID NO: 5, or the partial sequence codes for at least one of the eleven fragments of APIT obtained by peptide mass fingerprinting, ESI/MS, and Edman degradation. Further, the partial sequence can comprise a stretch of additional nucleotides selected from the sequences adjacent to the sequence selected from SEQ ID NO: 1, 3, or 5. Preferably, 1-60 additional nucleotides can be present at the 5' and/or the 3'-terminus. More preferably, 1-30 additional nucleotides can be present at the 5' and/or the 3'-terminus. Most preferably, 1-10 additional nucleotides can be present at the 5' and/or the 3'-terminus.

Furthermore, the nucleic acid may encode a fusion polypeptide as described above.

In a preferred embodiment of the invention the nucleic acid is operatively linked to an expression control sequence, e.g. a sequence which is capable of directing expression in a suitable host cell, e.g. a prokaryotic or eukaryotic host cell. The expression control sequence usually comprises a promoter and optionally operator or enhancer sequences which enable a transcription of the nucleic acid operatively linked thereto.

Furthermore, the expression control sequence may contain a translation signal, e.g. a ribosome binding sequence.

The nucleic acid of the present invention may be a recombinant vector which contains in addition usual vector sequences such as an origin of replication, a selection marker gene and/or a cloning site. Examples of suitable vectors such as plasmids, phages or viral vectors are known to the skilled person and are described e.g. in Sambrook et al., Molecular Cloning, A Laboratory Manual (2nd ed. 1998), Cold Spring Harbor, Laboratory Press.

A further aspect of the present invention is a recombinant cell transformed or transfected with a nucleic acid as described above. The recombinant cell may be a prokaryotic cell, e.g. a gram-negative prokaryotic cell such as *E. coli* or an eukaryotic cell, e.g. an insect cell or a vertebrate cell such as a mammalian cell. Techniques for transforming or transfecting host cells with nucleic acids are known to the skilled person and e.g. described in Sambrook et al., supra.

Still a further subject matter of the present invention is an antibody directed against the polypeptide as described above. The antibody may inhibit the cytotoxic activity of the polypeptide. The antibody may be a polyclonal or monoclonal antibody or a recombinant antibody, e.g. a chimeric antibody, a humanized antibody or a single chain antibody. Furthermore, the antibody may be an antibody fragment containing the antigen-binding site of the antibody, e.g. a Fab fragment. The antibody may be obtained by immunizing suitable experimental animals with an *Aplysia* polypeptide as described above or a partial fragment thereof or a peptide antigen optionally coupled to a suitable macromolecular carrier according to known protocols, e.g. by techniques which are described in Borrebaeck, Carl A. K. (Ed.), Antibody engineering (1992), or Clark, M. (Ed.), Protein engineering of antibody molecules for prophylactic and therapeutic applications in man (1993). By techniques for producing hybridoma cell lines according to Köhler and Milstein monoclonal antibodies may be obtained.

Methods for introducing a prosthetic group into a polypeptide are known in the art. Preferably, the FAD is introduced by a method comprising surface display of the polypeptide on a prokaryotic host, comprising the steps:
  (a) providing a prokaryotic host cell transformed with a nucleic acid fusion operatively linked with an expression control sequence, said nucleic acid fusion comprising sequences necessary for displaying the protein on the outer membrane, and
  (b) culturing the host cell under condition wherein the nucleic acid fusion is expressed and the expression product comprising the recombinant polypeptide is displayed on the surface of the host cell, and
  (c) contacting the recombinant polypeptide with FAD under conditions wherein FAD combines with the recombinant polypeptide and a functional recombinant polypeptide containing the prosthetic group is formed.

The nucleic acid fusion may be formed using a nucleic acid sequence as described above and further sequences necessary for surface display. Details describing the prokaryotic host cells, the sequences necessary for surface display of the polypeptide, culture conditions, and the conditions under which the recombinant polypeptide is contacted with FAD are described in WO 02/070645, which is included by reference herein.

A further aspect of the present invention relates to diagnostic or therapeutic applications in humans or animals. The polypeptide, and/or a nucleic acid, and/or a recombinant cell, and/or an effector, e.g. an inhibitor or activator of the polypeptide as described above can be used in such applications. The polypeptide as described above is able to selectively kill tumor cells. For example, T and B leukemia cell lines, a chronic myeloid leukemia cell line (K562), cells from an orphan and aggressive osteosarcoma (Ewings tumor: RDES, A673), a small cell lung cancer cell line (GLC4, GLC4/ADR), cervix cancer (Chang), and acute monocytic leukemia (THP-1) show an $IC_{50} \leq 10$ ng/ml APIT.

Healthy human cells are resistant against APIT-induced cell death. At a concentration of 40 ng/ml, APIT induces a cell death below 10% in normal HUVEC cells (Example 13). This indicates that the APIT $IC_{50}$ values of healthy cells are at least one order of magnitude higher than the $IC_{50}$ of tumor cells.

Resistance to apoptosis as well as multi drug resistance (MDR) represent severe problems in cancer therapy. It is therefore of particular interest that the polypeptide of the present invention kills apoptosis resistant cell lines as well as MDR cancer cell lines to the same extent as their non resistant counter parts. Over-expression of apoptosis inhibitors of the Bcl-2 family in cancer cell lines does not protect from APIT mediated cell death, confirming that APIT induces cell death in an apoptosis independent way. The MDR cell line GLC4/ADR possess almost the same sensitivity to APIT $IC_{50}$ 10 ng/ml) as the parental cancer line GLC4 does $IC_{50}$ 9 ng/ml).

Thus, the diagnostic or therapeutic application preferably relates to a method for diagnosis or treatment of hyperproliferative diseases, e.g. cancer. More preferably, the method is a method for diagnosis or treatment of lung cancer, breast cancer, prostate cancer, colon cancer, cervix cancer, uterus cancer, larynx cancer, stomach cancer, liver cancer, Ewings sarcoma, acute lymphoid leukemia, acute and chronic myeloid leukemia, apoptosis resistant leukemia, and/or MDR lung cancer. Moreover other tumor types can also be treated with the polypeptide, like pancreas cancer, gastric cancer, kidney cancer, gliomas, melanomas, chronic lymphoid leukemia, and/or lymphoma. Since all cancer cell lines tested (in total 24) were effectively killed by APIT, the polypeptide can be used for the treatment of solid tumors and leukemias in general including apoptosis resistant and multi drug resistant cancer forms.

A further aspect of the present invention is a pharmaceutical composition comprising the polypeptide of the present invention as described above, in a pharmaceutically effective amount and optionally together with suitable diluents and carriers or kit containing the composition together with other active ingredients, e.g. modulators of the polypeptide or other cytostatic or cytotoxic agents. The composition can be administered locally or systemically by any suitable means, e.g. orally, nasally or by injection (i.v., i.p., s.c., or i.m.) to a subject in need thereof. The components of a kit, which consists of at least two different compositions may be administered together or separately, e.g. at different times and/or by different routes.

In another embodiment, the pharmaceutical composition or the kit comprises a nucleic acid encoding for the polypeptide of the present invention as described above. Further, the pharmaceutical composition or kit may comprise both the polypeptide and the nucleic acid of the present invention.

From many studies it is known that tumor cells have an increased rate of metabolism compared to normal cells. A result of this high metabolic rate is a high concentration of reactive oxygen species (ROS, comprising $H_2O_2$) which originate from oxidative phosphorylation reactions by the electron transport chain of the mitochondria. As a consequence ROS detoxification reactions are increased in tumor cells, and interference with detoxification has a selective toxic effect on the tumor cells but not on normal cells. Likewise, increasing the concentration of $H_2O_2$ by administering the polypeptide of the invention in a predetermined amount may overcome the detoxification reactions and kill the tumor cells. The level of extra $H_2O_2$ produced by exogenous APIT does not affect normal cells because of their higher tolerance for additional $H_2O_2$. An administration of the polypeptide in a varying amount, e.g. a gradually changing, e.g. increasing amount leads to the production of a defined amount of $H_2O_2$ could thus be used for a selective killing of cancer cells.

The pharmaceutical composition or kit as described above can comprise a further component which is a substance capable of modulating the cytotoxic activity of the polypeptide, in a pharmaceutically effective amount and optionally together with suitable diluents, and carriers. In FCS (100%) at 37° C. and 5% $CO_2$ which reflect in vivo conditions, or in a medium containing 10% FCS (typical in vitro conditions) devoid of L-lysine and L-arginine, the activity of APIT (20 ng/ml) can be dose-dependently increased by the addition of L-lysine in a final concentration of 2-50 µg/ml. Thus, the high specifity of APIT for L-lysine (and L-arginine) allows for modulating the enzymatic activity of APIT and thus its cytotoxic activity by providing an additional substrate in vivo or in vitro. The substance capable of modulating the cytotoxic activity of the polypeptide can be L-lysine, L-arginine, a derivative or metabolic precursor of L-lysine, or L-arginine, or a mixture thereof. A derivative is a compound which is an APIT substrate. A metabolic precursor is a compound, which can be metabolized to a compound, which is an APIT substrate. Further, the modulator may be selected from flavine nucleosides, particularly FAD, since the presence of a flavine nucleoside prosthetic group leads to a great increase in APIT activity.

The pharmaceutical composition may comprise the polypeptide and at least one modulating substance as a mixture. Preferably, the modulating substances are provided in a kit consisting of separate preparations. More preferable, the polypeptide is provided for administration before the modulating substances.

During the passage through body fluids before reaching the tumor tissue, the cytotoxic activity of the polypeptide would be undesired, due to the toxic properties of $H_2O_2$. Thus, the composition may further comprise an inhibitor of the polypeptide. The inhibitor could have a short half-life time in the body fluid. A preferred inhibitor of the polypeptide is an antibody against the polypeptide (see above).

Modulating the activity of the polypeptide of the present invention can also be accomplished by modulating the product level, i.e. the $H_2O_2$ level. The degradation of at least one of the products, namely $H_2O_2$, results further on in consumption of the substrates L-lysine and L-arginine by the polypeptide of the present invention. Thus, these amino acids may be deprived. Since L-lysine and L-arginine are essential for living and growing of tumor cells, deprivation of these amino acids by a combination of the polypeptide of the present invention and an $H_2O_2$ scavenger may lead to the death of tumor cells. Thus, in another embodiment, the pharmaceutical composition may comprise the polypeptide of the present invention and an $H_2O_2$ scavenger. A preferred $H_2O_2$ scavenger is catalase. Preferably, a kit is provided consisting of separate preparations of the polypeptide of the present invention and catalase.

Further the polypeptide can be coupled with a substance and/or a particle which targets the polypeptide to the tumor tissue.

Further components of the pharmaceutical composition can be a nucleic acid coding for the polypeptide as described above, and/or a recombinant vector or cell containing the nucleic acid.

A further aspect of the present invention is a substance modified by interaction with APIT (termed target substance of APIT). A direct interaction is a contact of APIT with this substance. In an indirect interaction, the effect upon the substance includes at least one mediator substance, e.g a substance formed by APIT, or a receptor interacting with APIT and the components of the related transduction cascade.

As described above, a mediator of APIT acting on cellular polypeptides is $H_2O_2$. Thus, preferred target substances of APIT comprise cellular polypeptides, which can be modified by $H_2O_2$. A major modification identified in 2-DE SDS gel patterns of cells treated with APIT was a shift of peroxiredoxin I (Prx I, Swiss-Prot No. Q06830, Genbank identifier No. 548453, SEQ ID NO: 8), which was also detected in cells treated with $H_2O_2$. Prx I belongs to a class of peroxidases which are involved in the detoxification of ROS. Although the nature of the modification of Prx is not known, Prx I can be used as a marker for APIT anti-tumor activity.

Thus, particularly preferred substances which can be used as target substances of the polypeptide as described above are peroxidases, especially preferably peroxiredoxin I or a polypeptide having substantially the same biological activity as peroxiredoxin I. Peroxiredoxin I may comprise
  (a) the amino acid sequence shown in SEQ ID NO: 8, or/and
  (b) an amino acid sequence which is homologous to the sequence of (a) with at least 70%, preferably 80%, particularly preferably 90%, especially preferably 95%, or/and
  (c) a fragment of the amino acid sequence of (a) or (b).

Further, peroxiredoxin I may comprise an amino acid sequence or a fragment thereof as disclosed in at least one of the Genbank entries selected from gi:4505591 (NP_002565.1), gi:13626803 (XP_001393.2), gi:32455264 (NP_859047.1), gi: 32455266 (NP_859048.1), gi: 423025 (A46711), gi: 287641 (CAA48137.1), gi: 13937907 (AAH07063.1), gi: 18204954 (AHH21683.1) or gi:440306 (AAA50464.1).

WO 02/31144 discloses proteins modified by $H_2O_2$ which are targets of APIT: thioredoxin peroxidase 2 (Swiss Prot No. Q06830, Genbank identifier 548453), 60S ribosomal protein P0 (12654583), Hsp-60 (N-term) (14603309), stathmin (5031851), Rho GDI 2 (P52566, 1707893), 60S ribosomal protein P0(4506667), RNA binding regulatory subunit (O14805,12720028), hnRNP C1/C2 (4758544), hnRNP C1/C2 (4758544), proteasome subunit beta type 1 (P20618, 130853), pre-mRNA cleavage factor Im (5901926), proteasome subunit alpha type 7 (O14818,12643540), U2 small nuclear ribonucleo-protein A' (P09661, 134094), GAP SH3 binding protein (5031703), DNA replication licensing factor MCM4 (P33991, 1705520), thioredoxin peroxidase 1 (P32119, 2507169), 40S ribosomal protein S21 (P35265, 464710), 40S ribosomal protein S12 (P25398, 133742), phosphoglycerate mutase 1 (P18669, 130348), HCC-1 protein (13940310), HnRNP A2/B1 (4504447/14043072), IMP dehydro-genase 2 (P12268, 124419), hnRNP A/B (14724990).

Further targets of APIT identified by 2 DE gel electrophoresis, in-gel tryptic digestion, peptide mass fingerprinting by MALDI-MS, and identification of the proteins are summarized in Table 3.

Still a further target of APIT is a nucleic acid. The target nucleic acid can be a DNA or an RNA, which is a mRNA. The transcription of the mRNA is up- or downregulated in the presence of APIT and/or $H_2O_2$. Preferably, the transcription is changed by a factor of at least 2, and more preferably, by a factor of at least 4.

By a microarray of specific 60 mer oligonucleotides representing about 8500 human genes, about 70 mRNAs were identified which are targets of APIT. The information about the mRNAs are summarized in Table 4. Each mRNA is referenced by a "unigene cluster" which represents a number of nucleotide sequences belonging to the same gene or to closely related genes. Details of the nomenclature and the nucleotide sequences of the unigene clusters are public available under available via the world wide web at ncbi.nlm.nih.gov/ (Homepage of the National Center for Biotechnology Information).

For most of the unigene clusters of Table 4, the gene and/or the protein is known. It is a general principle that modulation of the transcription of a messenger RNA influences the amount of protein expressed. Thus, the proteins coded by the sequences of the unigene clusters of Table 4 are also targets of APIT, because APIT may influence their expression. The sequences of the proteins and of the nucleic acids coding for these proteins are referenced by the genbank identifier, accession number and/or version number (see Table 4). The sequences are public available under available via the world wide web at ncbi.nlm.nih.gov/.

Additional targets of APIT (nucleic acids, proteins) obtained by microarray analysis as described above are summarized in Table 5.

A preferred substance which can be used as a target substance for the polypeptide as described above is a nucleic acid coding for a peroxidase, particularly preferably peroxiredoxin I or a polypeptide having substantially the same biological activity as peroxredoxin I. The nucleic acid coding for peroxiredoxin I may comprise
  (a) the nucleotide sequence shown in SEQ ID NO: 7, or/and
  (b) a nucleotide sequence which corresponds to the sequence of (a) within the scope of the degeneracy of the genetic code, or/and
  (c) a nucleotide sequence hybridizing to the sequence of (a) or/and (b) under stringent conditions, or/and
  (d) a fragment of the nucleotide sequence of (a), (b) or (c).

SEQ ID NO: 7 is disclosed in Genbank entry gi:14721336 (XM001393).

Preferably, the nucleic acid encoding peroxiredoxin I may comprise a nucleotide sequence which is homologous to SEQ ID NO: 7 with at least 70%, particularly preferably at least 80%, especially preferably at least 90%.

In further preferred embodiments, the nucleic acid encoding peroxiredoxin I may comprise a nucleotide sequence or a fragment thereof as disclosed in at least one of the Genbank entries selected from gi: 13937906 (BC007063.1, PRDX1 transcript 3), gi: 18204953 (BC021683.1, PRDX1 transcript variant 3), gi: 32455265 (NM_181697.1, PRDX1 transcript variant 3), gi: 34528302 (AK131049.1, clone highly similar to PRDX1), gi: 287640 (X679851.1, PAG), gi: 32455263 (NM_181696.1, PRDX1 transcript variant 2), gi: 32455267 (NM_002574.2, PRDX1 transcript variant 2) or gi:440305, (L19184, NKEF A).

The target substance of the present invention (see Table 3, 4 and 5), which is identified by one of the methods as described above, may be used for the development of new pharmaceutical agents, e.g. by known high-throughput screening procedures which may be cellular screening procedures or molecular based screening procedures. These pharmaceutical agents may act upon cellular receptors and/or components of the signal transduction pathways activated or inhibited by APIT.

Degenerative diseases like Alzheimer's and Parkinson's disease are characterised by excessive ROS production of the affected tissue. Drugs which either activate $H_2O_2$ detoxification or inhibit $H_2O_2$ production may be used for therapy of degenerative diseases like Alzheimer's or Parkinson's disease. Fast growing tumor cells produce more ROS and thus require an efficient $H_2O_2$ detoxification system. Drugs which either activate $H_2O_2$ production or which interfere with $H_2O_2$ detoxification may be used for therapy of proliferative diseases like tumors. Since e.g. thioredoxin peroxidases 1 and 2 have been shown to be overexpressed in cells at risk for diseases related to ROS toxicity including degenerative diseases like Alzheimer's and Parkinson's disease, and have been shown to be overexpressed in tumor cells (Butterfield et al., 1999, *Antioxidants & Redox Signalling*, 1, 385-402), the targets of Table 3 and 4 might be important targets for the development of drugs for treatment of degenerative diseases like Alzheimer's and Parkinson's disease and of proliferative diseases like tumors.

NK-cells have been shown to protect against malignant cells in chronic myelogenous leukemia (CML), but their number and inducibility is reduced during the progression of the disease. This reduction and dysfunction is due to the production of $H_2O_2$ by CML-cells (Mellqvist, Blood 2000, 96, 1961-1968). NK-cells encountering $H_2O_2$ are inhibited in their lytic activity, are made resistant to IL-2 activation and undergo apoptosis/necrosis. Any therapy providing CML-patients with ROS-hyposensitive NK-cells therefore would be of great benefit. The targets described above could be used to modulate the $H_2O_2$ sensitivity of NK-cells or to inhibit the $H_2O_2$ production of malignant cells, e.g. CML-cells.

Arteriosclerosis with its progression to heart disease, stroke and peripheral vascular disease continues to be the leading cause of death in all western civilisations. Enhanced ROS-production (via endothelial NADPH-oxidase) is required and sufficient to generate the pathologic phenotype (Meyer, FEBS Letters 2000, 472, 1-4). Therefore, targets mediating the effect of $H_2O_2$ are useful to develop new drugs for treatment of arteriosclerosis and the associated diseases like heart disease, stroke and other vascular diseases. These targets are suitable to detoxify $H_2O_2$ and/or to block the $H_2O_2$ induced signalling pathways.

Target compounds, e.g. peptides, polypeptides or low-molecular weight organic compounds, which are capable of modulating the effect of $H_2O_2$ may be identified in a screening system comprising the use of the APIT polypeptide as described above. Particularly, a modulation of the APIT activity, i.e. L-amino oxidase activity, may be determined.

Thus the present invention further relates to a pharmaceutical composition comprising as an active agent at least one of the target substances as described above.

Still a further aspect of the present invention is an inhibitor of a target as described above, in particular an inhibitor of the detoxification system of the cell which eliminates reactive oxygen species, e.g. $H_2O_2$. Surprisingly, it was found that the inhibition of detoxifying enzymes sensitized tumor cells to the cytotoxic activity of the polypeptide of the present invention as described above. Example 11 demonstrates that knock-down of peroxiredoxin I sensitized tumor cells for APIT-induced cell death.

Preferably, the inhibitor is an inhibitor of peroxidase, particularly of peroxiredoxin I. The inhibitor may be an antibody or a nucleic acid molecule, i.e. useful for antisense inhibition or as an siRNA molecule. It is particularly preferred that the inhibitor is an inhibitor of peroxiredoxin I activity which is an RNA molecule, particularly a double-stranded RNA molecule comprising a nucleic acid sequence of at least 15 nucleotides complementary to a peroxiredoxin I transcript. It is especially preferred that the peroxiredoxin I transcript is derived from SEQ ID NO:7.

The one or two strands of the RNA molecule as described above may, independently, have a length of 19 to 25 nucleotides, preferably 19 to 23 nucleotides. Especially preferred is a length of the one or two strands of 19, 20, 21, 22 or 23 nucleotides. The RNA molecule as described above may comprise at least one modified nucleotide. Preferably, modified nucleotides are selected from the group consisting of oxetane[1-(1',3'-O-anhydro-β-D-psicofuranosyl)-nucleotides, locked nucleic acid (LNA) nucleotides, hexitol nucleotides, altritol nucleotides, cyclohexane nucleotides, neutral phosphatate analogs.

The double-stranded RNA molecule as described above may have one or two 3' overhangs with, independently, a length of 1 to 5 nucleotides, preferably 1 to 3 nucleotides, particularly preferably 2 nucleotides. The one or two overhangs may consist of ribonucleotides, deoxyribonucleotides, modified nucleotides as described above or combinations thereof.

The double-stranded RNA molecule as described above may comprise a sequence selected from the group of sequences consisting of SEQ ID NO: 9, SEQ ID NO: 10, SEQ ID NO: 11; SEQ ID NO: 12; SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29.

Yet another aspect of the present invention is a pharmaceutical composition or kit comprising an inhibitor as described above, preferably an RNA molecule, particularly preferred a double-stranded RNA molecule, or a nucleic acid encoding such an RNA molecule. The pharmaceutical composition or kit may comprise the inhibitor as sole active agent in order to increase the amount of reactive oxygen species present in the cell due to endogenous production. More importantly, the pharmaceutical composition or kit may comprise the inhibitor and a substance capable of producing reactive oxygen species. In a preferred embodiment, the pharmaceutical composition or kit comprises as an active agent a combination of APIT and at least one inhibitor of a target substance as described in Table 3 or/and Table 4 or/and Table 5, more preferably at least one inhibitor of peroxiredoxin I. In another preferred embodiment, the pharmaceutical composition or kit comprises at least one inhibitor of a target substance as described in Table 3 or/and Table 4 or/and Table 5, more preferably at least one inhibitor of peroxiredoxin I, and the polypeptide of the present invention having cytotoxic activity as described above. In yet another preferred embodiment, the pharmaceutical composition or kit comprises at least one inhibitor of a target substance as described in Table 3 or/and Table 4 or/and Table 5, more preferably at least one inhibitor of peroxiredoxin I, and a cytotoxic polypeptide producing reactive oxygen species or/and a nucleic acid encoding such a cytotoxic polypeptide, wherein the cytotoxic polypeptide is selected from cytotoxic polypeptides obtainable from sea hares, e.g. Cyplasin C, Cyplasin L, Aplysianin A, Aplysianin P, Aplysianin E, Dolabellin A, Dolabellin C, Dolabellin P, Julianin G, Julianin S, or is selected from L-Lysine oxidases like EC 1.4.3.14 from *Trichoderma*, AIP from Chub mackerel (AJ400871), Apoxin from *Crotalus* (AAD45200.1), or from other L-amino acid oxidases like EC 1.4.3.2 or from other enzymes which produce $H_2O_2$. More preferably, the pharmaceutical composition or kit comprises (I) a polypeptide obtainable from *Aplysia* comprising an amino acid sequence selected from:

(a)
D-G-E-D-A-A-V                    (SEQ ID NO:32)
and/or (b)
(D/Q)-G-(I/V)-C-R-N-(Q/R)-R-(Q/P),    (SEQ ID NO:33)

(c)
F-A-D-S,                         (SEQ ID NO:34)

(d)
G-P-D-G-(I/L)-V-A-D,             (SEQ ID NO:35)

(e)
P-G-E-V-S-(K/Q)-(I/L),           (SEQ ID NO:36)

(f)
A-T-Q-A-Y-A-A-V-R-P-I-P-A-S-K,   (SEQ ID NO:37)

(g)
D-S-G-L-D-I-A-V-E-Y-S-D-R,       (SEQ ID NO:38)

(h)
G-D-V-P-Y-D-L-S-P-E-E-K          (SEQ ID NO:39)
or/and (i)                              SEQ ID NO:41,
                                 43, 44, 45.

or a fragment thereof wherein the polypeptide or the fragment has cytotoxic activity, or/and a nucleic acid encoding the cytotoxic polypeptide obtainable from *Aplysia* comprising
(i) a nucleotide sequence as shown in SEQ ID NO:40 or 42 or at least the polypeptide coding portion thereof or the complement thereof,
(ii) a nucleotide sequence corresponding to the sequence of (a) within the scope of degeneracy of the genetic code, or the complement thereof, or/and
(iii) a nucleotide sequence hybridizing under stringent conditions with the sequence of (a) or/and (b), and
(II) an inhibitor of a target substance as described in Table 3 or/and Table 4 or/and Table 5.

The inhibitor of the present invention may be coupled to carriers, (e.g. lipids, peptides, biodegradable polymers, dendrimers, vitamins, carbohydrate receptors) for in vivo targeting to predetermined tissues or/and cell types.

Delivery of the inhibitors of the present invention may be improved by linking the inhibitors with lipids, liposomes, PEG, nanoparticles or/and polymers, for example.

Yet another aspect of the present invention is a gene therapy delivery system suitable for delivery of a nucleic acid encoding an inhibitor which is an RNA molecule, preferably a double-stranded RNA molecule as described above, capable of inhibiting peroxidase, particularly peroxiredoxin I activity. Suitable delivery systems for gene therapy are commonly known in the art, for instance a recombinant adenoviral delivery system, a recombinant adenoviral-derived system or a recombinant lentiviral system. Further, the nucleic acid may be delivered by virus-like particles from *Papillomaviridae* and *Polyomaviridae*. Further, bacteria may be used as a delivery system, e.g. attenuated gram negative bacteria, particularly attenuated *salmonella* strains. The nucleic acid encoding the inhibitor is operatively linked with expression control sequences which are adapted to the host and to the delivery system. Such expression control sequences are known to a person skilled in the art. Expression of the two strands of the RNA molecule may be performed together in a self-complementary configuration which allows formation of a small hairpin RNA (shRNA) in which the two strands of the double-stranded molecule are interconnected by an additional loop, or may be performed as two separate strands which hybridize later on in the host.

Yet another aspect is a pharmaceutical composition or kit comprising a delivery system suitable for delivery of a nucleic acid encoding an inhibitor which is an RNA molecule, particularly a double-stranded RNA molecule preferably comprising a nucleic acid of at least 15 nucleotides complementary to a peroxiredoxin I transcript as described above, to predetermined tissues or/and cell types.

In yet another embodiment, the invention concerns a method for diagnosis or treatment of cancer, wherein a pharmaceutical composition as described above is administered to a subject in need thereof.

SEQ ID NO: 1, 3 and 5 show the APIT nucleotide sequences as shown in FIG. 4c. SEQ ID NO: 2, 4 and 6 show the amino acid sequences derived from SEQ ID NO: 1, 3 and 5, respectively. SEQ ID NO: 7 and 8 show the nucleotide sequence and the amino acid sequence of Prx I. SEQ ID NOs: 9 to 29 show the nucleotide sequences of double-stranded siRNA molecules capable of inhibiting Prx I activity. SEQ ID NOs: 30 and 31 show sequences of double stranded siRNA molecules obtained from the Lamin AC and the luciferase sequence, respectively. SEQ ID NOs: 32 to 39 show the amino acid sequences of fragments of cytotoxic *Aplysia* polypeptides. SEQ ID NO: 40 and 42 show partial sequences of nucleic acids encoding cytotoxic polypeptides of *Aplysia punctata*. SEQ ID NOs: 41, 43, 44 and 45 show the derived amino acid sequences of SEQ ID NOs: 40 and 42. SEQ ID NOs: 46 to 55 show the amino acid sequences of fragments of cytotoxic *Aplysia* polypeptides.

The invention is explained in more detail by the following figures, tables and examples.

FIG. 1

A, Anion exchange chromatography. Filtrated and concentrated ink was loaded onto a Source Q15 column. Proteins were eluted by a linear gradient from 0 to 800 mM NaCl, fractions were collected every minute (2 ml/min). Absorption was measured at 280 nm. Horizontal bar indicates active fractions.

B, Gelfiltration. Active fractions from the Source Q15 were pooled and concentrated and applied to a Superose 12 HR 10/30 column. Proteins were eluted with 100 mM potassium phosphate buffer (pH 7.2). Fractions were collected every minute (0.5 ml/min). Horizontal bar indicates active fractions.

FIG. 2

A, Phenotype of APIT-induced cell death. Jurkat cells were cultured for 7 hours in the presence (APIT) or absence (medium) of APIT (30 ng/ml) and phase contrast images were recorded.

B, Lack of apoptotic DNA fragmentation in ink-treated cells. Jurkat cells were incubated in medium (control) or treated with cycloheximide (chx; 10 µg/ml) or ink (ink, 1/500 diluted) for 2, 4 and 6 h. Isolated DNA was visualized on a 1.6% agarose gel by ethidium bromide staining.

C, APIT mediated loss of metabolic activity. APIT (10 ng/ml) and the tetrazolium-salt WST-1 were added simultaneously to Jurkat cells and turnover of WST-1 was measured photometrically. White circles: medium control; black circles: APIT-treated samples; mean absorbance of 8 replicates "SD.

D, Cell death induced by ink. Jurkat cells were treated with ink (1/500 diluted) and propidium iodide (PI) uptake was measured as indicator for dead cells.

FIG. 3

A, Heat sensitivity of ink. Dialysed ink was incubated for 10 min at the indicated temperatures and enzymatic activity was measured as $H_2O_2$-production (mean of triplicates "SD). Blank: medium control.

B, pH-sensitivity of APIT. APIT (60 ng) was incubated for 10 min at 25° C. in 0.1 M potassium phosphate at indicated pH values. Enzymatic activity was measured as $H_2O_2$-production (mean of triplicates "SD).

C, Sensitivity to increasing amounts of urea: Dialyzed ink (black bars, 1/500 diluted) and as positive control 0.625 mM á-keto isocaproic acid (open bars) were treated with indicated concentrations of urea for 30 min at 25° C. Enzymatic activity (15 min. 25° C.) was measured as á-keto acid formation via MBTH.

FIG. 4

A, N-terminal (SEQ ID NO: 33) and internal peptide sequences (SEQ ID NOS 47,49-50, 77, 51, 37, and 52-55 disclosed respectively in order of appearance) of the APIT protein.

B, List of oligonucleotides used for cloning of the APIT gene (SEQ ID NOS 58-61, 63, 62, and 64-66 disclosed respectively in order of appearance).

C, Nucleotide sequence of the APIT CDNA (SEQ ID NO: 1) and the derived amino acid sequence (SEQ ID NO: 2). The dinucleotide binding fold (VAVVGAGPGGANSAYML-RDSG-LDIAVFE) (SEQ ID NO: 56) and the GG-motif (RVGGRLFT) (SEQ ID NO: 57) are indicated by boxes. Consensus amino acid residues are indicated by bold letters. The N-terminal sequence of mature APIT (dashed line) and of internal peptides (solid line) derived by Edman degradation and mass finger prints are indicated. Sequence variations of the three clones are indicated by small boxes (SEQ ID NOS 3 and 5 are also disclosed respectively in order of appearance).

D, Variation of the N-terminus of APIT in 11 further clones (SEQ ID NO: 78).

FIG. 5

A, Anion exchange chromatography of purified APIT. Proteins were eluted by a linear gradient from 0 to 800 mM NaCl and fractions were collected every minute. Absorption was measured at 280 nm (AU: Absorption unit).

B, Fractions 24, 27 and 29 were separated by SDS-PAGE and tested for metabolic activity by WST-1 assay. High activity (+;++) correlated with the presence of a prominent 60 kDa band (fractions 24 and 29). Activity is given as the dilution leading to >85% reduction of the metabolic activity of Jurkat cells (+/−=1:900; +=1:2700; ++=1:8100).

C, Absorption spectra of fractions 24 (black line), 27 (dashed line) and 29 (dotted line).

FIG. 6

A, APIT induced $H_2O_2$ production in medium in the absence of cells. APIT (260 ng/ml) was incubated in medium in the presence (open bar) or absence (black bar) of Jurkat cells ($5\times10^5$/ml). After 1 h of incubation at 37° C. supernatants were alkylated with N-ethylmaleimide and $H_2O_2$ was measured (mean values of 3 independent experiments +/−SD).

B, Catalase inhibits ink induced cell death. Jurkat T-cells were incubated for 8 h with ink in the presence (black bars) or absence (white bars) of catalase. Cytotoxicity was measured as PI uptake (mean of triplicates "SD).

C, Catalase protects from APIT induced loss of metabolic activity. Metabolic activity of Jurkat cells was measured after incubation with APIT (20 ng/ml) or anti-CD95 for 3 h in the presence (black bars) or absence (white bars) of catalase. (mean of 5 replicates "SD).

D, Phenotype of APIT induced cell death is mediated by hydrogen peroxide. Jurkat cells were cultured for 7 hours in the presence (APIT) or absence (medium) of APIT (60 ng/ml) or $H_2O_2$ (500 μM) and were analyzed by phase contrast microscopy. Catalase was added in combination with APIT to neutralize $H_2O_2$ (APIT+CAT).

E, Long-term exposure with ink from *Aplysia punctata* and catalase resulted in tumor cell death by amino acid deprivation. Metabolic activity of Jurkat T-cells was measured after overnight incubation (>18 h) with ink (white bars) or $H_2O_2$ (250 iM, black bars) in the presence (+) or absence (−) of catalase (2000 U/ml) (mean of triplicates "SD).

FIG. 7

A, Enzymatic activity of APIT in the presence of different medium supplements. APIT (200 ng/ml) was incubated for 60 min at RT with RPMI+/−10% FCS or KRG supplemented with different medium ingredients and $H_2O_2$ production was measured. (EAA=essential amino acids, NEAA=non essential amino acids, concentrations see Table 1).

B, Substrate specificity of APIT and ink. The enzymatic reaction of dialysed ink (open bars) with different L-amino acids in potassium phosphate buffer was measured as $H_2O_2$-production. 50 μM $H_2O_2$ and amino acid free medium (control) were used as control. Aliquots of dialyzed ink were digested with trypsin (hatched bars) or proteinase K (black bars) at 37° C. for 2 h prior to testing the substrate specificity. Arg=L-arginine, 1 mM; Lys=L-lysine, 1 mM; EAA=essential amino acids, 1 mM; NEAA=non essential amino acids, 1 mM.

C, APIT induced cell death depends on the presence of L-lysine or L-arginine. Jurkat cells were incubated with APIT (20 ng/ml) for 6 h in the presence (white bars) or absence of L-lysine and L-arginine (black bars). Cytotoxicity was measured as PI uptake (mean of triplicates "SD).

D, APIT induced loss of metabolic activity depends on the presence of L-lysine or L-arginine. Jurkat cells were incubated with APIT (20 ng/ml) or anti-CD95 (150 ng/ml) in the presence (open bars) or absence (black bars) of L-lysine or L-arginine and metabolic activity was measured (mean of 5 replicates "SD).

E, APIT transforms L-lysine into an á-keto acid. APIT was incubated with L-lysine and the formation of á-keto acid was measured photometrically by its reaction with MBTH.

F, Michaelis-Menten kinetic of APIT activity with L-lysine. $K_m$ value for L-lysine was determined as $H_2O_2$ production.

G, Proposed reaction mechanism of L-amino acid oxidases according to Macheroux et al. (2001 Eur. J. Biochem. 268: 1679-1686). Encircled are compounds which we demonstrated to participate in the reaction catalyzed by APIT.

FIG. 8

A, Quantification of the mRNAs of Lamin A/C and Prx I after transfection of specific siRNA (open bars) and control Luciferase siRNA (black bars) with quantitative realtime PCR. Shown are the relative mRNAs levels compared to the mRNA of GAPDH measured in the same RNA preparation.

B, Sensitization of HeLa cells by knock down of Prx I. Specific siRNAs directed against the mRNA of Luciferase (Luc, transfection control), Lamin A/C (control knock down) and Prx I were transfected in HeLa cells and the metabolic activity of transfectants treated in the presence (black bars) or absence of APIT (open bars) was measured. Note that the knock down of Prx I but not of the other genes sensitized cells for the cytotoxic activity of APIT.

FIG. 9

APIT did not induce actin depolymerisation in HeLa cells. Untreated HeLa cells (A) and HeLa cells treated with Cytochalasin (B) or APIT (C) were stained with Phalloidin-TRITC for actin and Hoechst 33258 for nuclei staining. Subsequently, fluorescence microscopy was performed. Actin staining is shown in bright white, nuclei are displayed in transient grey.

FIG. 10

HUVEC cells are resistant to the APIT induced cells death. HUVEC and Jurkat cells were incubated with APIT over night and subsequently LDH release in the culture supernatant was measure photometrically. Shown are the results of two independent experiments+/−standard deviation.

TABLE 1

Composition and concentrations of mixtures of essential and non-essential amino acids as well as single amino acids used in FIG. 7A.

TABLE 2

APIT kills different kinds of tumor cells. Different tumor cell lines (50,000 cells in 100 Fl) were incubated for 14 h in the presence of increasing amounts of APIT. Metabolic activity of the cells was measured via turnover of WST. The $IC_{50}$ values reflect the APIT concentration at which the metabolic activity is decreased to 50%. (* stands for $IC_{50} \geq 20$ ng/ml at the given cell concentration of 50,000/100 Fl.)

TABLE 3

List of proteins which were changed in their expression or modified after treatment with APIT (upregulation (+), downregulation (−), or modification (m) in column "effect"). The proteins are referenced by the genbank identifier and/or accession number and/or version number.

TABLE 4 AND TABLE 5

List of genes (referenced by unigene cluster number) and gene products (proteins) which were modulated in their expression more than 2 fold after incubation with APIT for two hours. The proteins are referenced by the genbank identifier and/or accession number. Transcription rates are indicated as increase (+, 2 to ≤4 times; ++, 4 to 6 times in Table 4 or 4 to 25 times in Table 5) or decrease (−, 2 to ≤4 times; −−, 4 to 6 times).

EXAMPLE 1

Purification of APIT

*Aplysia punctata* were gained from the Station Biologique Roscoff, Bretagne, France. Crude ink was prepared by gentle squeezing the sea hares in sterile seawater. Insoluble particles were removed by ultracentrifugation (82,000 g, 30 min, 4° C.) and supernatants were stored at −70° C.

Figure 2A:
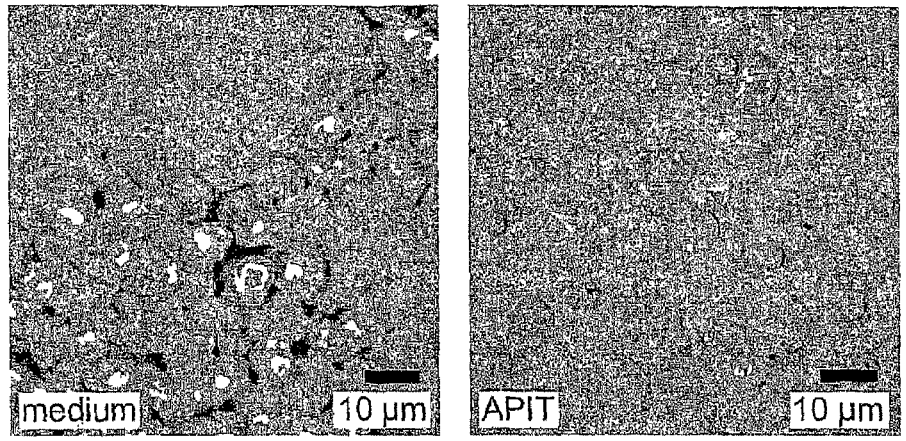
Figure 2B:
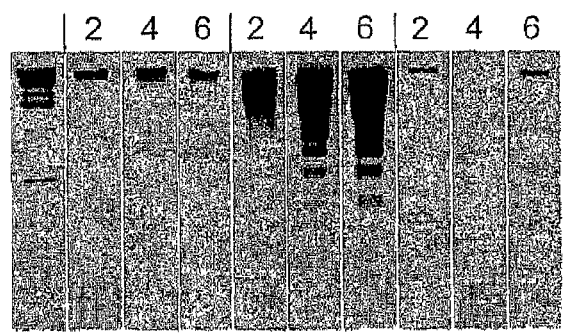

APIT was purified from crude ink via anion exchange chromatography and gelfiltration. The thawed ink was filtered through Whatman filter No. 4 under slight vacuum and subsequently through a 5 Fm and 0.45 Fm syringe filter. The filtrate was concentrated by using Ultrafree-15 Units (Millipore, exclusion weight 30 kDa) followed by three washing steps with 20 mM Tris HCl (pH 8.2). After centrifugation at 10.000 g for 5 min the supernatant of the concentrate (20-60 fold) was applied to a Source Q15 column ((10 mm, length 40 mm) equilibrated with 20 mM Tris HCl, pH 8.2. Proteins were eluted by a linear gradient from 0 to 800 mM NaCl over 50 ml at a flow rate of 2 ml/min (FIG. 1A). The purity of the fractions was determined by SDS-PAGE and subsequent rapid silver staining. APIT appears as a band at 60 kDa. Cytolytic activity was measured as APIT-induced reduction of the metabolic activity of Jurkat cells via turnover of WST (see example 2). Enzymatic activity was determined as described in example 3. Fractions which show high purity and cytotoxic respectively enzymatic activity (FIG. 1A; fraction 42 to 48) were pooled, concentrated and loaded onto a Superose 12 HR 10/30 column (Pharmacia). Proteins were eluted with 100 mM potassium phosphate buffer (pH 7.2) at a flow rate of 0.5 ml/min The first peak represents the active APIT (FIG. 2B; fraction 11 to 14).

EXAMPLE 2

Phenotype of APIT-Induced Cell Death

The purple fluid of *Aplysia punctata* contains a cytolytic activity which induces rapid and extensive death of Jurkat T cells in culture. APIT induces cell death of tumor cells which resembles neither apoptosis nor necrosis. In order to classify the APIT-induced cell death we looked for common features of apoptosis and necrosis.

Jurkat T cells were harvested in the log phase, centrifuged and adjusted to a density of $5 \times 10^5$/ml with fresh medium (RPM supplemented with 10% FCS, 100 U/ml penicillin and 100 µg/ml streptomycin). Cells were cultured with APIT, cycloheximide as a positive control or medium at 37° C., 5% $CO_2$ and 100% humidity for the indicated times. Fragmented DNA of apoptotic cells was analyzed according to Herrmann et al. (1994, Nucleic Acid Research 22: 5506-5507). Cell vitality was determined as metabolic activity via the turnover of WST-1 (ROCHE, Mannheim) to red formazan by the mitochondrial dehydrogenase of viable cells. Absorbance of the cell suspension was measured photometrically at 450 nm (690 nm reference). Toxicity was measured by quantifying propidium iodide uptake (1 µg/ml in PBS) by Flow Cytometry.

Figure 2C:
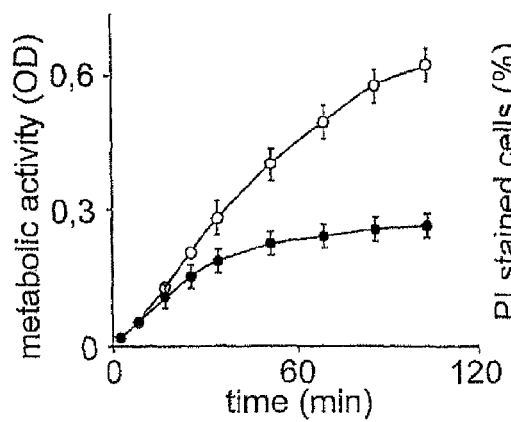
Figure 2D:
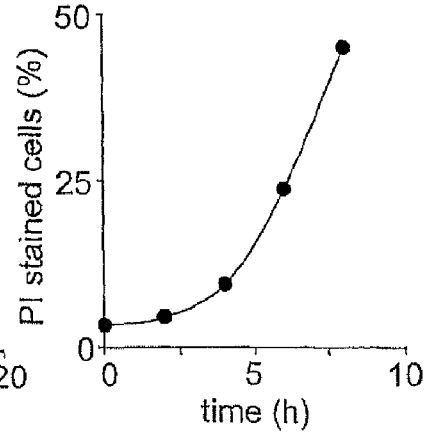

Morphologically, tumor cells treated with ink or APIT did not exhibit typical morphological apoptotic or necrotic signs of cell death (FIG. 2A), and neither blebbing nor swollen cells were detected when cells were treated with a lethal dose of ink. Cells did not form clusters anymore, cytoplasm became translucent and nuclei prominent (FIG. 2A). The intracellular movements of plasma and organelles stopped, detachment and formation of vacuoles were observed when adherent cells were incubated with APIT (data not shown). Consistent with the absence of apoptosis, fragmented DNA or nuclei were not detected in ink-treated tumor cells (FIG. 2 B); moreover, caspases were not activated (data not shown). Metabolic activity of tumor cells was blocked as early as 30 min after exposure to ink or APIT (FIG. 2C). Ink-treated tumor cells rapidly took up propidium iodide (PI) indicating plasma membrane permeabilization and cell death (FIG. 2D).

EXAMPLE 3

Stability of APIT

APIT was further characterized by its sensitivity to heat, low pH and high concentrations of urea.

For determination of its heat sensitivity native ink was dialyzed against PBS at 4° C. for several days to separate chromopeptides. Dialysed ink was incubated for 10 min at the indicated temperatures, and activity was measured immediately as enzymatic production of $H_2O_2$. This assay is based on the finding that APIT transforms L-lysine to $H_2O_2$ and á-keto acid. The production of $H_2O_2$ was determined via the turnover of ABTS (2,2-Azino-bis(3-ethylbenzthiazoline-6-sulfonic acid) to a green formazan in the presence of $H_2O_2$ by horseradish peroxidase. Heat-treated ink was incubated with L-lysine (1 mM) in 100 Fl 100 mM potassium phosphate buffer, pH 7.2 for 10 min at 25° C. The reaction was stopped by adding 1 Fl of 10 M phosphoric acid. To 25 Fl of this solution 1 mM ABTS and I Unit horseradish peroxidase was added in 225 Fl 100 mM potassium phosphate buffer, pH 5.0. Absorption was measured photometrically at 405 nm (reference 690 nm).

Purified APIT was challenged to different pH-values by adding a mixture of monobasic and dibasic potassium phosphate and phoshphoric acid rendering the desired pH. After a 10 min incubation pH of samples was adjusted to pH 7.2 by adding appropriate amounts of dibasic phosphate. Afterwards enzymatic activity was measured as $H_2O_2$-production as described above.

The activity of APIT after treatment with urea was measured via the production of á-keto acid, which was quantified photometrically by its reaction with the hydrazone MBTH (3-methyl-2-benzothiazolone hydrazone hydrochloride) as described by Soda (1968). Dialyzed ink was incubated with urea at indicated concentrations for 30 min. Subsequently the remaining enzymatic activity was measured without removing urea for 15 min at 25° C. As control, defined amounts of á-keto isocaproic acid (Sigma; K-0629) were treated equally.

Figure 3A:
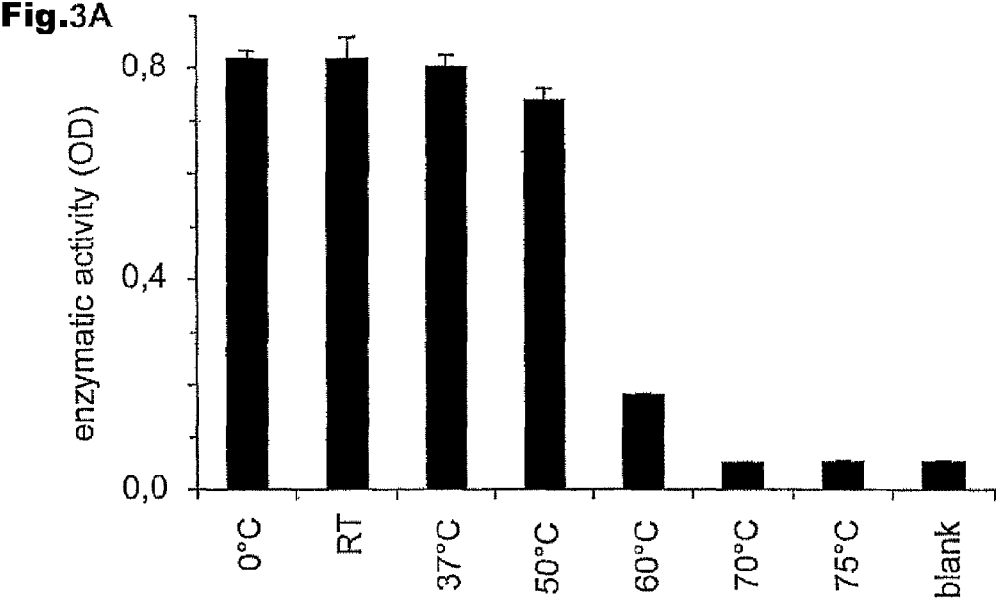
Figure 3B:
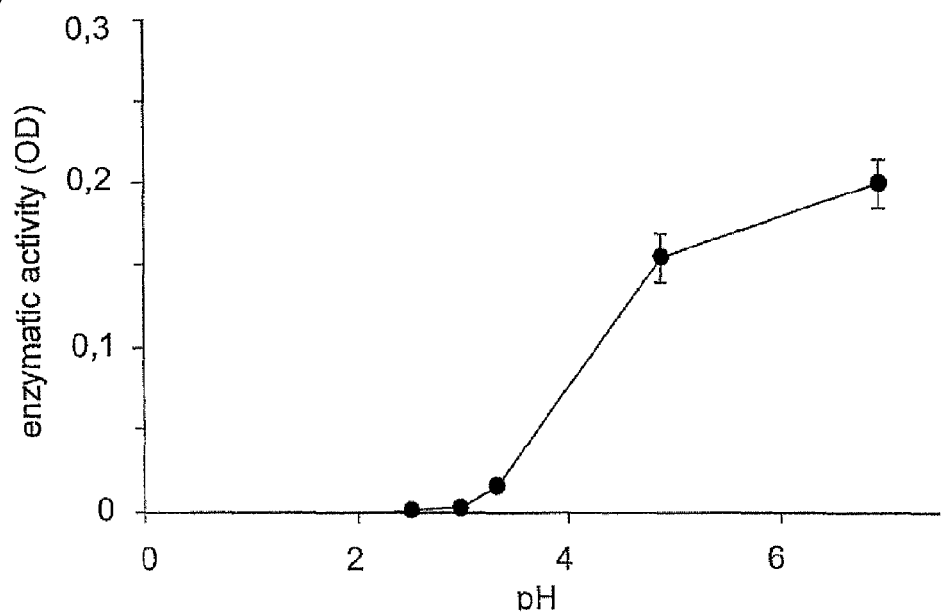
Figure 3C:
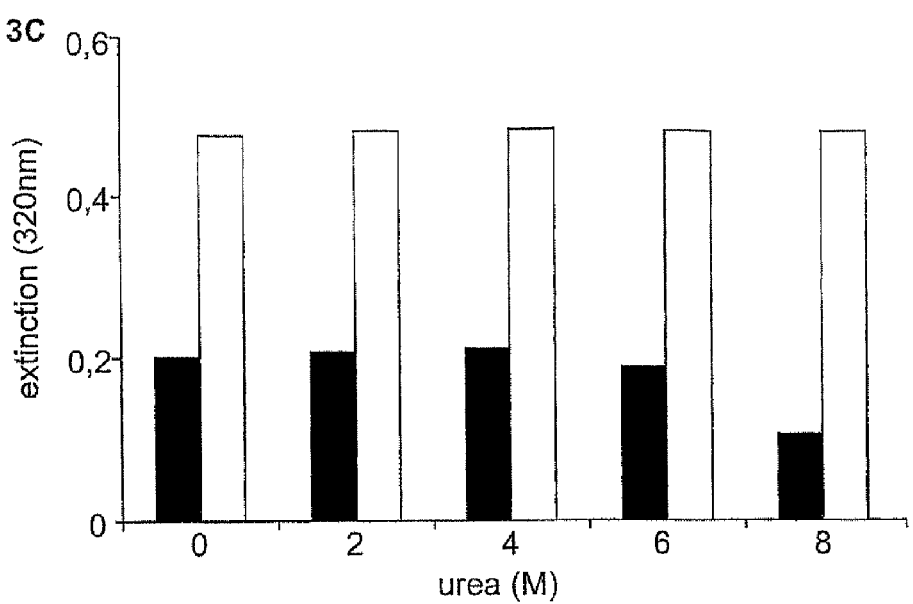

APIT was characterized by its heat sensitivity and was found to exhibit a high and constant activity after pre-incubation for 10 min at 0° C. to 50° C. Activity was clearly reduced at 60° C. and absent at temperatures of 70° C. or higher (FIG. 3A). APIT also shows a loss of activity with decreasing pH, with complete inactivation after a 10 min pre-incubation at pH 3 or lower (FIG. 3B). An outstanding feature of APIT is its resistance to urea (FIG. 3C). After 30 min treatment with 6 M urea, the activity of APIT was almost unaffected. At 8 M urea, the activity was reduced by about 50%.

EXAMPLE 4

Sequencing and Cloning of APIT

In order to clone the cDNA of APIT N-terminal and internal peptide sequences were identified by PMF (peptide mass fingerprint), ESI/MS and Edman degradation (FIG. 4A). A suitable internal peptide sequence was used to design a degenerated primer for PCR (FIG. 4A, underlined sequence) with reverse transcribed mRNA, prepared from *Aplysia punctata* tissues. Subsequent 5'-RACE yielded the full length cDNA which was cloned and analyzed.

Amino Acid Sequencing by Peptide Mass Fingerprint (PMF), ESI/MS and Edman Degradation.

Purified APIT was separated by SDS PAGE and 2 DE gel electrophoresis (Thiede et al., 2001, J. Biol. Chem. 276: 26044-26050). The N-terminus of APIT was identified from a single band/spot of a PVDF blot by Edmann degradation. For the identification of internal peptide sequences a single band/spot was punched from the gel, digested with trypsin and dissolved in aqueous trifluoroacetic acid (Thiede et al., 2001, J. Biol. Chem. 276:26044-26050). Tryptic peptides were separated using a Smart-HPLC system with a column of 2.1 mm inner diameter and 10 cm length (FRPC C2/C18 SC 2.1/10, Smart System, Pharmacia Biotech, Freiburg, Germany) and an acetonitrile gradient in 0.1% (v/v) trifluoroacetic acid at a flow rate of 100 Fl/min at room temperature. The peptide fractions were dried, dissolved in 6 Fl 0.3% (v/v) aqueous trifluoroacetic acid/acetonitrile (2:1) and analyzed by MALDI-MS. The mass spectra were recorded by using a time-of-flight delayed extraction MALDI mass spectrometer (Voyager-Elite, Perseptive Biosystems, Framingham, Mass., USA) as previously described (Thiede et al., 2001, J. Biol. Chem. 276:26044-26050). Briefly, fifty mg/ml 2,5-dihydroxybenzoic acid in 0.3% (v/v) aqueous trifluoroacetic acid/acetonitrile (2:1) was used as matrix and 0.3 Fl of the sample and 0.3 Fl of the matrix were mixed and applied to a gold-plated sample holder and introduced into the mass spectrometer after drying. The spectra were obtained in the reflectron mode by summing 50-150 laser shots. For N-terminal sequencing peptide fractions containing single masses were loaded onto a Biobrene-coated glass fiber filter, transferred to a PVDF membrane and excised. Sequencing was performed using a Procise sequencer (Applied Biosystems, Weiterstadt, Germany).

Cloning of the APIT Gene.

In order to dissect mantle gland, nidamental gland, digestive gland and opaline gland some animals were relaxized by injection of 5'10 ml sterile $MgCl_2$ solution (380 mM). Isolated tissues were frozen immediately in liquid nitrogen. Total RNA was prepared from these tissues using the 'peq gold TRIfast' reagent (Peqlab). mRNA was reverse transcribed using the tagged oligo dT oligonucleotide 5'-tcc taa cgt agg tct aga cct gtt gca $t_{(18)}$-3' (SEQ ID NO: 58) (FIG. 4B, oligo 1) and the Superscript II polymerase (LIFE) at 42EC. In order to amplify a fragment of the APIT gene the degenerated primer 5'-tc gtg ttc gar tac tci gay cg-3' (SEQ ID NO: 59) derived from the APIT peptide VFEYSDR SEQ ID NO: 48) (FIG. 4B, oligo 2) and the specific primer 5'-ctg tag gtc tag acc tgt tgc a-3' (SEQ ID NO: 60) (FIG. 4B, oligo 3) directed against the tag sequence of the oligo dT-primer was used. PCR was performed with the expand long template system (ROCHE, Mannheim) at 68EC and the product was cloned into the pCMV-vector (Stratgene) and sequenced. The 5' terminal cDNA of APIT was cloned using the 5' RACE System (LIFE) according to the manufacturers instructions. Primers 5'-ccg tgt aga tct cac tgc cat a-3' (SEQ ID NO: 61) (FIG. 4B, oligo 4) or 5'-ccg ttg agt tgt aga cct-3 (SEQ ID NO: 62) (FIG. 4B, oligo 6) were combined with the primers 5'-ggc cac gcg tcg act agt acg ggi igg gii ggg iig-3' (SEQ ID NO: 63) (FIG. 4B, oligo 5) or 5'-aatt ggc cac gcg tcg act agt ac-3' (SEQ ID NO: 64) (FIG. 4B, oligo 7) to yield a product which was cloned into the pCDNA3-vector (Invitrogen) and sequenced. Finally, full length APIT cDNA was obtained by amplifying the APIT using the specific primers 5" aa ttc tcg tct gct gtg ctt ctc ct (SEQ ID NO: 65) (FIG. 4B, oligo 8) and 5" gac tta gag gaa gta gtc gtt ga (SEQ ID NO: 66) (FIG. 4B, oligo 9) and cloned into the pGEX-4T3 Vector (Amersham). DNA from 3 clones of transfected *E. coli* was prepared and sequenced.

The identity of the isolated gene was confirmed by comparing the computed translational product (FIG. 4C) with the amino acid sequences of the tryptic peptides (FIG. 4A) and the peptide mass fingerprint. It consisted of 1608 bp coding for a protein of 535 amino acids (FIG. 4C) with the predicted mass of 60,167 dalton and a pI of 4.59. The N-terminal 18 amino acids of APIT comprised a putative secretion signal sequence which was absent from the mature protein, most likely due to posttranslational modification during secretion. Furthermore, APIT exhibited homology to FAD-binding oxidoreductases with a conserved dinucleotide binding fold around amino acids 39 to 66 followed by a so-called GG-motif typical for certain oxidases like LAAO, MAO (FIG. 4C) (Dailey et al., 1998, J. Biol. Chem. 273:13658-13662; Vallon et al., 2000, Proteins 38:95-114; Macheroux et al., 2001 Eur.

J. Biochem. 268:1679-1686). The highest degree of homology existed to the Cyplasin from *A. punctata*, the Aplysianin from *A. kurodai* and the mucus-toxin of the giant African snail *Achatina fulica*.

Comparing the 3 derived DNA-sequences we often found differences in the third position of coding triplets which nevertheless only seldom produced changes in the amino acid sequence of APIT (FIG. 4C).

By the method described above, further 11 clones were isolated from *Aplysia punctata* which have a homology to the sequences described in FIG. 4 of at least 95%. Several mutations of the amino acid sequence were found in the domain comprising the dinucleotide binding fold and the GG motif, which probably have no effect upon the function (FIG. 4D). In Pos. 22 of SEQ ID NO: 2, C is replaced by S in two clones. In Pos. 52, A is replaced by T in one clone. In Pos. 60, L is replaced by Q in 7 clones. In Pos. 69, D is replaced by H in one clone. In Pos. 77, T is replaced by S in one clone.

EXAMPLE 5

FAD Association

The toxic and enzymatic activity of APIT is due to the presence of an attached FAD.

Figure 5A:
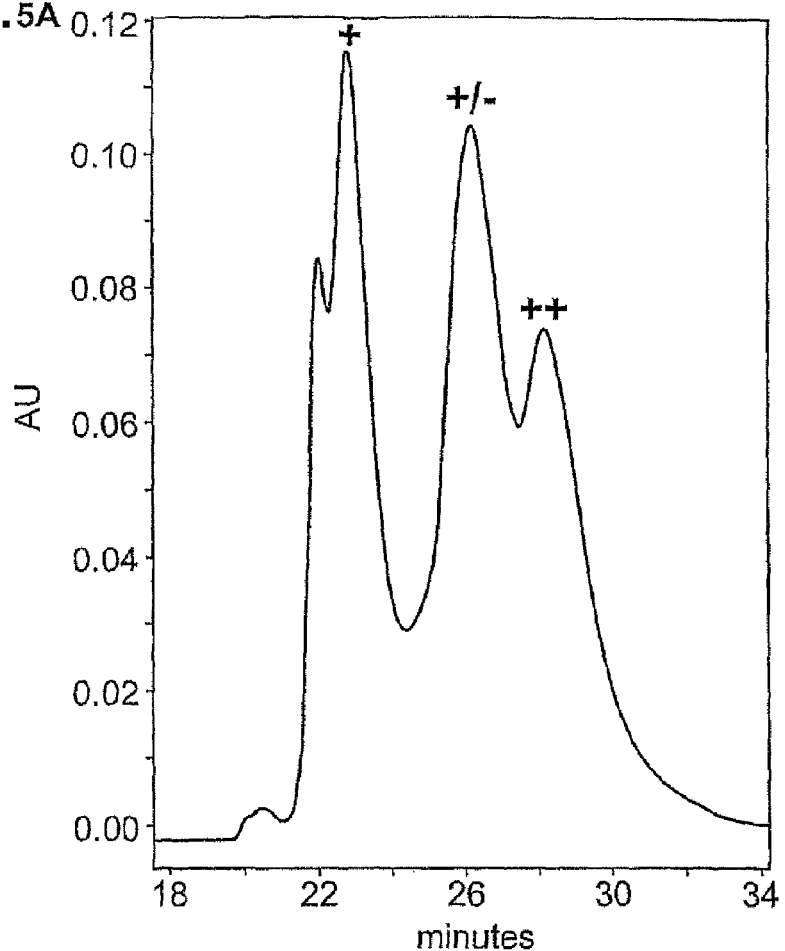
Figure 5B:
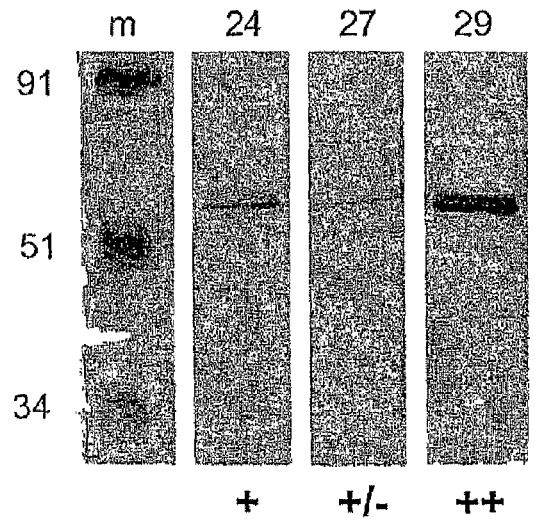
Figure 5:
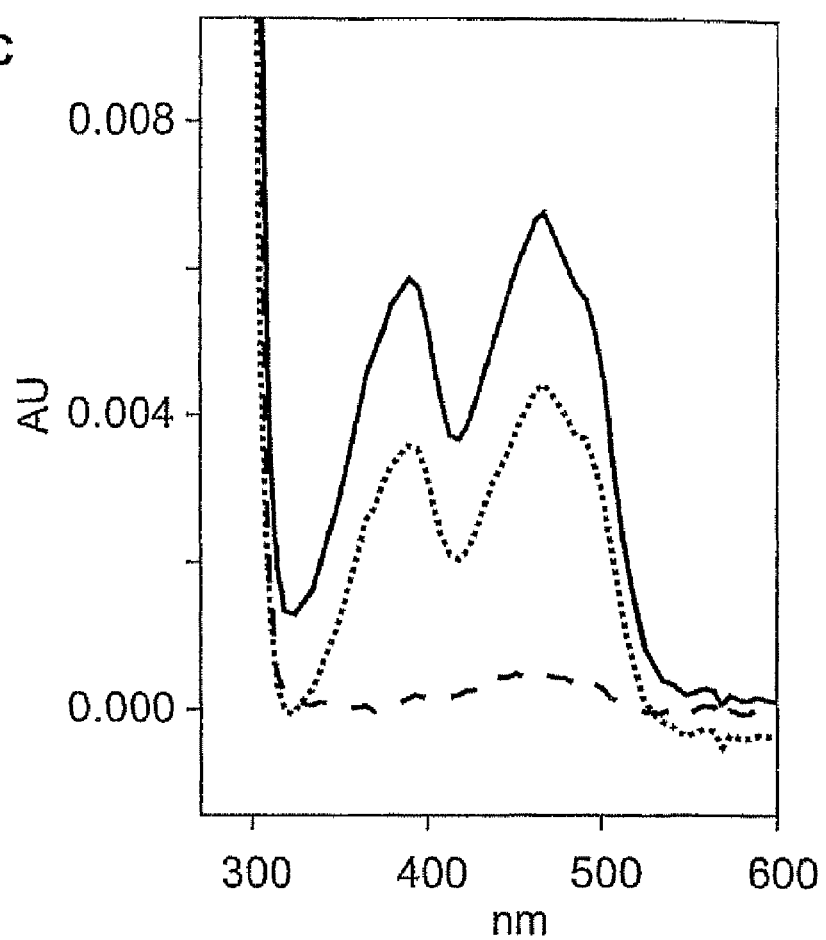

In order to purify the tumor lytic activity, ink from *A. punctata* was subjected to different purification protocols and afterwards each fraction was tested for its toxic activity (see example 1). Activity always correlated with the presence of a protein of approximately 60 kDa (FIGS. 5 A and B). Moreover, APIT was found to contain carbohydrate residues using the DIG Glycan/Protein double labeling method (Roche; data not shown). Furthermore, all spectra of the highly active fractions exhibited a double peak at 390/470 nm (FIG. 5C) which is characteristic for protein bound flavines (Massey et al., 2000, Biochem Soc. Trans. 28:283-96). Heating of APIT for 10 min to 60° C., which is accompanied by a substantial loss of activity also results in loss of detectable FAD-absorption, as is the case with lowering the pH to inactivating values around pH 3. Heating and pH-challenge of APIT was performed as described in example 3 (data not shown).

Consistently, APIT contained the conserved dinucleotide binding fold involved in pyrophosphate binding (Wierenga et al., 1986, J. Mol. Biol., 187:101-107) which is found in many flavoproteins (FIG. 4B; example 4). Moreover, in APIT like in many oxidases a so-called GG-motif is found adjacent to the dinucleotide binding fold (Dailey et al., 1998, J. Biol. Chem. 273:13658-13662, Vallon et al., 2000, Proteins, 38:95-114). Based on the structure of the dinucleotide binding fold and conserved sequence motifs, FAD containing proteins are ordered into 4 families (Dym et al., 2001, Protein Sci. 10:1712-28). According to this classification and based on homology APIT belongs to the Glutathione reductase 2 family (GR2) (Dym et al., 2001, Protein Sci. 10:1712-28). The data show that FAD is a necessary prosthetic group for toxic and enzymatic activity of APIT.

EXAMPLE 6

Cell-Death is Mediated Via $H_2O_2$

Proteome analysis revealed that thioredoxin peroxidase II is involved in the APIT mediated tumor cell death. Thioredoxinperoxidase II is involved in detoxification of reactive oxygen species (ROS) by reducing hydrogen peroxides as well as other peroxides. We therefore tested whether $H_2O_2$ is produced during APIT incubation and found that $H_2O_2$ is the mediator of APIT-induced cell death. Scavenging this toxic compound by catalase over a certain period of time (6-8 hours) results in survival of APIT treated cells. Notable long-term exposure of tumor cells (>18 hours) with APIT and catalase causes the death of tumor cells by the deprivation of L-lysine and L-arginine.

$H_2O_2$ production was measured after incubation of APIT in medium alone and in cell suspension as described in example 3. Toxicity was measured by quantifying propidium iodide uptake (1 µg/ml in PBS) by Flow Cytometry. Cell vitality was determined as metabolic activity via the turnover of WST-1 (ROCHE, Mannheim) to red formazan by the mitochondrial dehydrogenase of viable cells. Absorbance of the cell suspension was measured photometrically at 450 nm (690 nm reference).

Figure 6A:
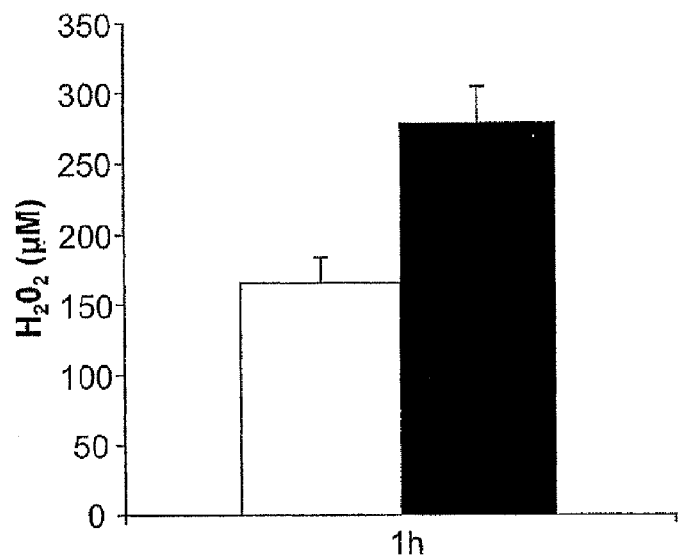
Figure 6B:
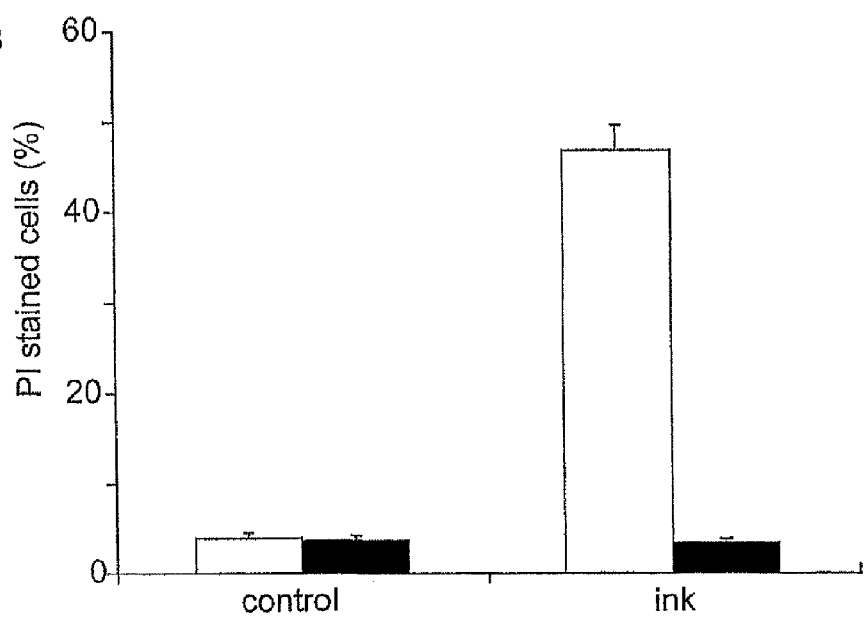
Figure 6C:
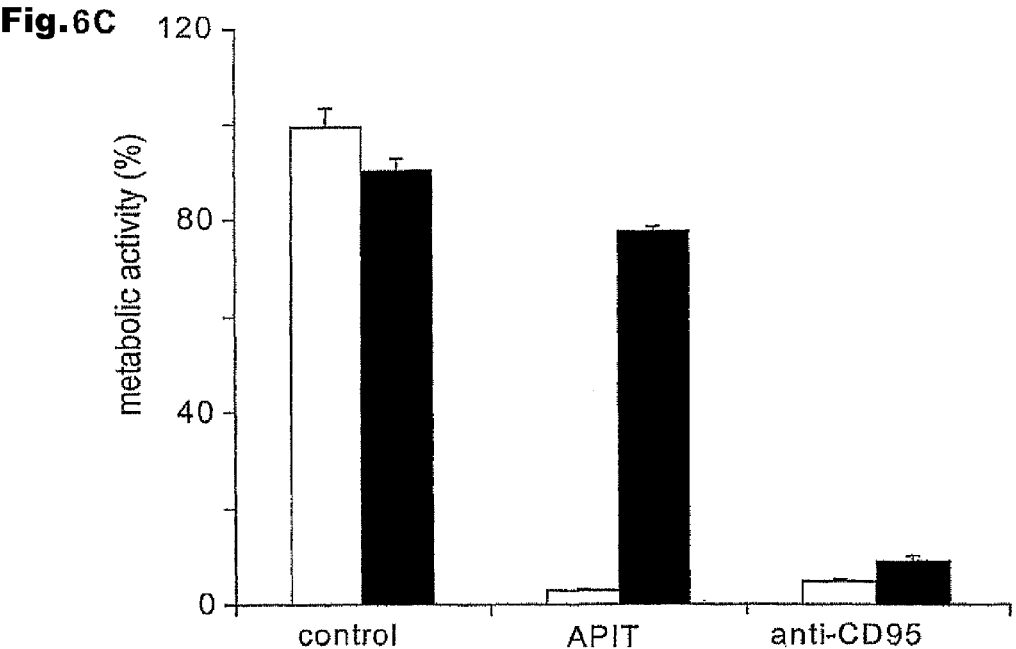
Figure 6D:
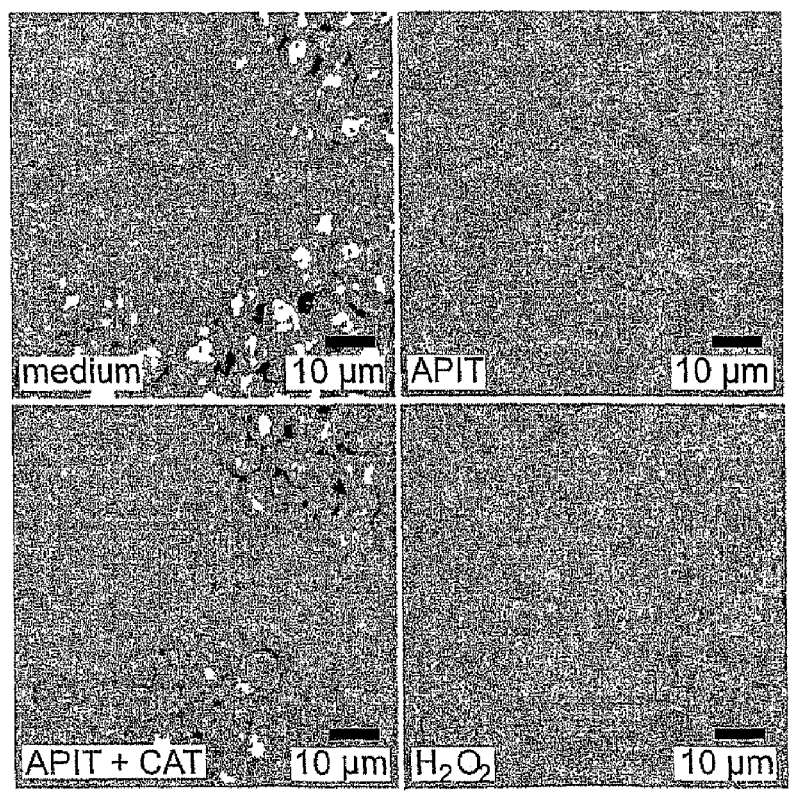

As shown in FIG. 6A, APIT induced the production of $H_2O_2$ in the presence (167 µM) as well as in absence of cells (280 µM). This strongly argues for an enzymatic activity of APIT which transforms medium ingredients under the production of hydrogen peroxide. In the presence of cells the measured $H_2O_2$ amount is somewhat lower which might be explained by cellular consumption and degradation of $H_2O_2$. In the absence of APIT $H_2O_2$ was not detectable. To investigate whether the APIT-induced cell death is mediated by $H_2O_2$, cells were treated with APIT in the presence of the $H_2O_2$ degrading enzyme catalase and then stained with PI. Catalase completely abolished the ink-induced increase of PI stained cells (FIG. 6B). Degradation of $H_2O_2$ by catalase also inhibited the rapid break-down of metabolic activity induced by APIT (FIG. 6C) but, as expected, was ineffective in blocking CD95 (Fas/Apo-1)-induced cell death in the same assay (FIG. 6C). In the presence of catalase APIT no longer induced morphological changes of tumor cells as judged by microscopic investigation (FIG. 6D). The highly efficient inhibition by catalase in particular suggested that no other substance than $H_2O_2$ elicits the toxic effect observed in APIT-treated samples. Consistently, $H_2O_2$ induced the phenotype typical for APIT-treated cells (FIG. 6D). Furthermore, proteome analyses revealed changes in $H_2O_2$ treated cells which were characteristic of APIT-treated cells. These data together clearly demonstrated that the cytotoxic activity depended on the $H_2O_2$ producing enzymatic activity of APIT.

Long-term exposure of Jurkat cells to ink from *Aplysia punctata* in combination with catalase resulted in metabolic activity being decreased to 20% (FIG. 6 E, right panel, white bar). The same result is achieved by treatment with purified APIT in combination with catalase (not shown). Since catalase was effective in inhibiting the $H_2O_2$-induced loss of metabolic activity completely (FIG. 6E, right panel, black bar), it was concluded that long-term treatment with APIT in the presence of an $H_2O_2$ scavenger, such as catalase, kills tumor cells not by the remaining low $H_2O_2$ concentrations but by the deprivation of L-lysine and L-arginine.

EXAMPLE 7

APIT is a L-Lysine/L-Arginine a-Oxidase. Enzymatic Activity is a Prerequisite for Toxicity APIT produced $H_2O_2$ in RPMI medium in the absence of cells. In order to identify the substrates in cell culture medium which are converted to $H_2O_2$ by APIT, we prepared different media with defined amino acid composition by supplementing HEPES buffered modified Krebs Ringer medium (KRG: 25 mM HEPES pH 7.4, 125 mM NaCl, 5 mM KCl, 1.2 mM $KH_2PO_4$, 5 mM $NaHCO_3$, 6 mM glucose, 1.2 mM $MgSO_4$, 1 mM $CaCl_2$) with 10% FCS, 2 mM glutamine, essential and non-essential amino acids (Invitrogen), or single essential amino acids in concentrations equivalent to RPMI medium (Invitrogen). Media were adjusted to pH 7.4 and filter sterilized. After incubation of these media with purified APIT the enzymatic activity was measured as $H_2O_2$ production via turnover of ABTS (2,2-Azino-bis(3-ethylbenzthiazoline-6-sulfonic acid) to a green formazan in the presence of $H_2O_2$ and horseradish peroxidase (FIG. 7A and Table 1).

In a next step we checked whether the substrate specificity could be impaired by digest of APIT. For proteolytic digest aliquots of dialysed ink were treated for 2 h with proteinase K (0.05 mg/ml final) in PBS at 37° C. Reaction was stopped by adding aprotinin (1 μg/ml final) or PEFA ([4-(2-aminoethyl)-benzolsulfonyl fluoride-hydrochloride]-hydrochloride; 0.25 mg/ml final), and digest was checked on a 15% SDS-PAGE. After incubation of digested ink with different amino acid compositions in potassium phosphate buffer the enzymatic activity was measured as $H_2O_2$ production (FIG. 7B).

In order to test whether withdrawal of L-lysine and L-arginine results in rescue of APIT-treated cells we incubated Jurkat cells in medium lacking L-lysine and L-arginine. Control cells were cultured in a medium containing L-lysine(HCl (40 mg/l) and L-arginine(HCl (240 mg/l). Toxicity was measured by quantifying propidium iodide uptake (1 μg/ml in PBS) by Flow Cytometry (FIG. 7C).

Cell vitality was determined as metabolic activity via the turnover of WST-1 (ROCHE, Mannheim) to red formazan by the mitochondrial dehydrogenase of viable cells. Absorbance of the cell suspension was measured photometrically at 450 nm (690 nm reference). As control tumor cells were killed by anti-CD95 treatment (FIG. 7D).

á-Keto acids were quantified photometrically by their reaction with the hydrazone MBTH (3-methyl-2-benzothiazolone hydrazone hydrochloride) as described (Soda et al., 1968, Anal. Biochem. 25:228-235) (FIG. 7E).

The $K_m$ value for L-lysine was determined as $H_2O_2$ production and calculated according to Michaelis Menten with the GraphPad Prism 3.0 software (GraphPad Software, San Diego Calif. USA) using non linear regression (FIG. 7F).

Figure 7D:
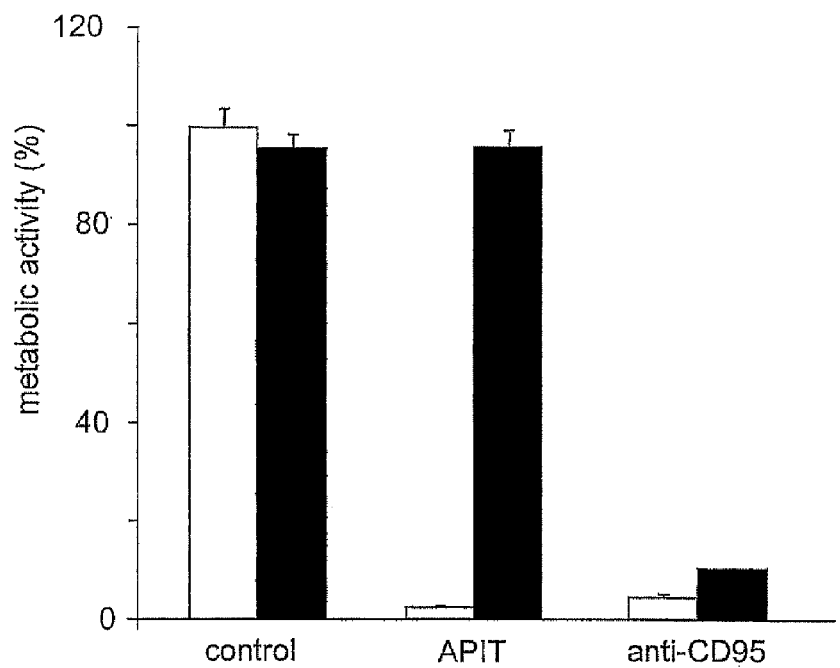

Surprisingly, from all amino acids tested only L-lysine and L-arginine served as substrates for APIT to produce hydrogen peroxide (FIG. 7A). Moreover, the restricted substrate specificity was even maintained when APIT was digested with protease K suggesting that the protease resistant fragment of APIT contains both, the active domain and the domain which determines the substrate specificity (FIG. 7B). These data were confirmed by functional analyses which showed that APIT was unable to induce cell death (FIG. 7C) or reduce metabolic activity (FIG. 7D) in tumor cells incubated in medium lacking L-lysine and L-arginine, indicating that the enzymatic activity of APIT is the prerequisite for its toxicity. L-lysine and L-arginine deprivation had no influence on the metabolic activity of tumor cells under the experimental conditions (FIG. 7D). Activation of CD95(Fas/Apo-1) efficiently impaired cell vitality irrespective of the presence of L-lysine or L-arginine (FIG. 7D), demonstrating that cell death can be induced under L-lysine and L-arginine limited conditions.

Figure 7E:
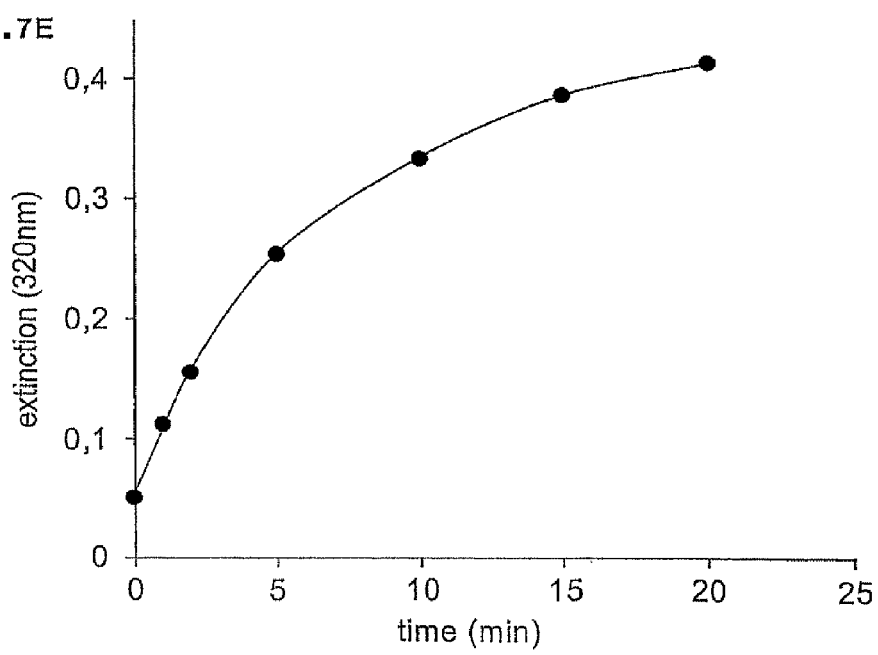
Figure 7F:
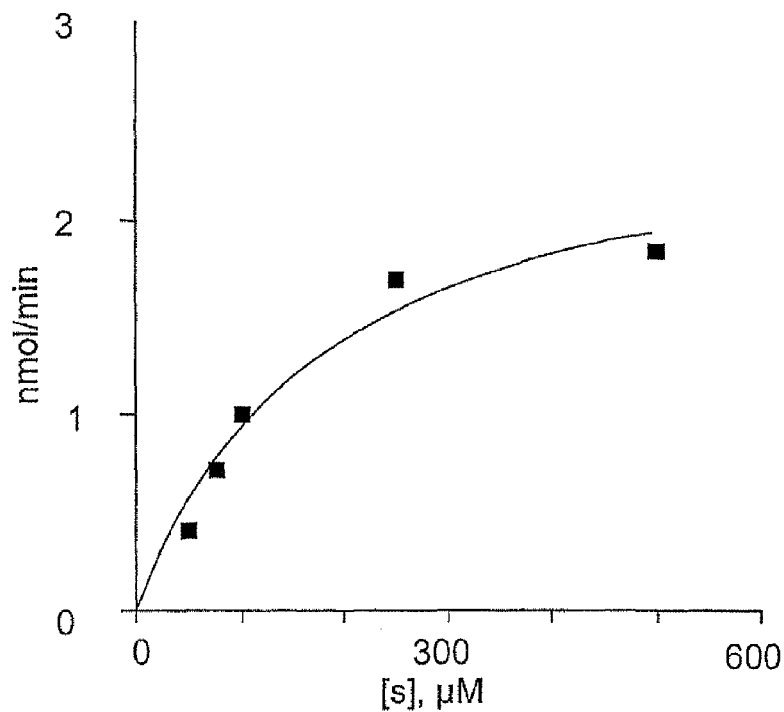
Figure 7G:
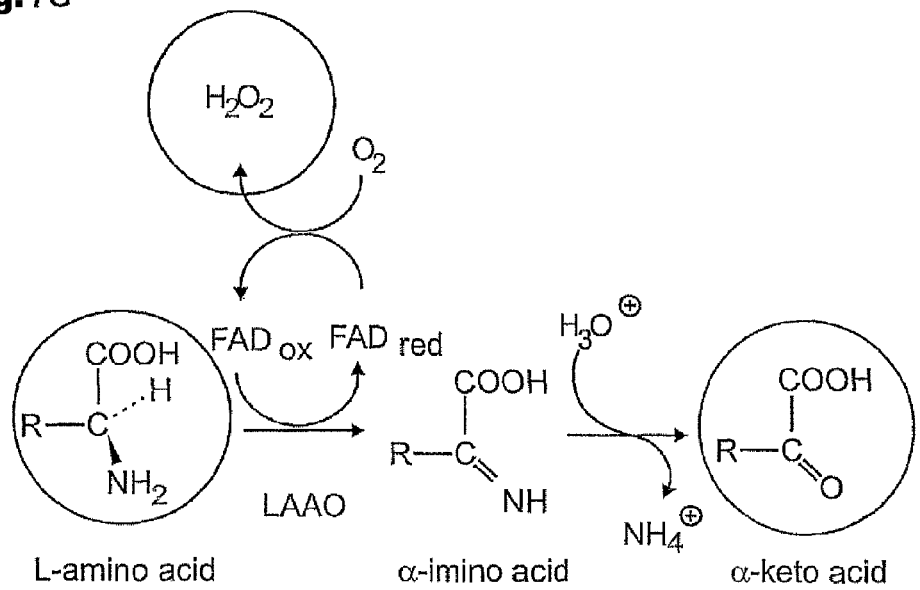

As shown in the reaction scheme in FIG. 7G, á-keto derivatives are produced by amino acid oxidases and these could indeed be demonstrated when L-lysine was used as substrate for APIT (FIG. 7E). These results suggested that APIT catalyses the formation of $H_2O_2$ by the reaction outlined in FIG. 7G. Kinetic studies analyzed according to Michaelis-Menten revealed a $K_m$ of 0.182 mM for L-lysine (FIG. 7F).

By adding L-lysine (2-50 μg/ml) to tumor cells which are cultured with APIT (20 ng/ml) in medium depleted of L-lysine and L-arginine or in pure FCS, the metabolic activity of the tumor cells can be reduced down to 16% respectively 50% of the control cells without additional L-lysine. This shows that the tumorolytic effect of APIT can be manipulated by changing the amount of available substrate which is of significance for in vivo studies and/or for application of APIT in pharmaceutical compositions and/or methods for treatment of cancer.

EXAMPLE 8

Sensitivity of Different Tumor Cell Lines to APIT Induced Cell Death

Tumor cells were harvested in the log phase. Triplicates of each 50,000 cells were cultured in a flat bottomed 96-well-plate in 100 Fl medium with increasing concentrations of APIT. After 14 hours the metabolic activity of the cells was determined by addition of 10 Fl WST-1 per well (ROCHE, Mannheim). The yellow tetrazolium salt is cleaved to red formazan by cellular enzymes of viable cells. The metabolic activity correlates with cell vitality and was quantified by measuring the absorbance of the dye solution with a spectrophotometer at 450 nm (reference 650 nm).

APIT is able to kill different tumor cells. T and B cell leukemia cell lines Jurkat neo, CEM neo, SKW neo), a chronic myelogenous leukemia cell line (1K562), and cells from an orphan and aggressive osteosarcoma (Ewings tumor: RDES, A673) showed the highest sensitivity to the APIT induced cell death $IC_{50} \le 5.6$ ng/ml), followed by cells derived from small cell lung cancer (GLC4, GLC4/ADR), cervix cancer (Chang) and acute monocytic leukemia (THP-1) $IC_{50} \le 10$ ng/ml). Most of the adherent growing cells of solid tumors (breast cancer: MCF-7, SK-BR-3; prostate cancer: PC3, DU-145; colon cancer: HT-29; cervix cancer: HeLa; uterus cancer: Hec-1-B; larynx cancer HEp-2; stomach cancer: AGS; liver cancer: Hep G2) and the monocyte leukemia cell line MonoMac 6 are less sensitive at the indicated cell concentration $IC_{50} \le 20$ ng/ml), but become more sensitive when lower cell concentrations were used $IC_{50}$ 5-10 ng/ml).

Resistance to apoptosis as well as multi drug resistance (MDR) represent severe problems in cancer therapy. It is therefore of particular interest that APIT kills apoptosis resistant cell lines as well as MDR cancer cell lines equally efficient as their non resistant counter parts (Tab. 2): Over-expression of apoptosis inhibitors of the Bcl-2 family in acute lymphoblastic leukemia cell lines (CEM Bcl-$X_L$, Jurkat Bcl-2) as well as in B cell leukemia (SKW Bcl-2) (Tab. 2; 4th row) does not protect from APIT mediated cell death and results in $IC_{50}$ values of $\le 6$ ng/ml, similar to the non-transfected parental cell lines, confirming that APIT induce cell death in an apoptosis independent way. The MDR cell line GLC4/ADR (Tab. 2, 5th row) was generated by selection with doxorubicin (Zijlstra et al., 1987, Cancer Res. 47:1780-1784). Its multifactorial MDR is caused by over-expression of MRP-1 and a decreased activity of the DNA topoisomerase II. GLC4/ADR cells possess almost the same sensitivity to APIT ($IC_{50}$ 10 ng/ml) as the parental line GLC4 does $IC_{50}$ 9 ng/ml).

EXAMPLE 9

Proteome Analysis: Change in Protein Expression Pattern in Jurkat T Cells after Treatment with APIT Treatment with APIT.

Jurkat T cells ($5 \times 10^5$/ml) were incubated with APIT (20 ng/ml) for 8 h at 37° C. in 5.0% $CO_2$ in the presence of 1 μg/ml cycloheximide. Controls were performed without APIT.

Total Cell Lysate.

The Jurkat T cells were solubilized in 5 volumes of a buffer containing 9 M urea, 25 mM Tris/HCl, pH 7.1, 50 mM KCl, 3 mM EDTA, 70 mM DTT, 2.9 mM benzamidine, 2.1 µM leupeptin, 0.1 µM pepstatin, 1 mM PMSF, and 2% carrier ampholytes (Servalyte pH 2-4, Serva, Heidelberg, Germany). After 30 minutes of gentle stirring at room temperature, the samples were centrifuged at 100000 g (Ultracentrifuge Optima TLX, Beckman, München, Germany) for 30 minutes with a TLA120.2 rotor, which were kept at room temperature before centrifugation. The clear supernatant was frozen at −70° C.

Proteomics.

The methods of preparing 2-DE gels, staining with Coomassie Blue G-250, staining with silver nitrate, in-gel tryptic digestion, peptide mass fingerprinting by MALDI-MS, and identification of the proteins are described in Jungblut et al., Molecular Microbiology, 2000, 36, 710-725.

Identification was performed using the peptide mass fingerprinting analysis software MS-Fit (available via the world wide web at prospector.ucsf.edu/ucsfhtml3.2/msfit.htm) or ProFound (available via the world wide web at canada.proteometrics.com/prowl-cgi/ProFound.exe?FORM=1).
Searches were performed in the databases NCBInr and SwissProt. The proteins are referenced by the genbank identifier, accession number and/or version number.

Results.

APIT induces either upregulation, downregulation, or modification of the proteins. Modification in the context of this example is a change in the apparent mass and/or the apparent pI value of the protein. By comparison of 2-DE patterns of APIT-treated whole cell lysates with the corresponding patterns of untreated cells, the proteins as described in Table 3 were identified to be affected by APIT.

EXAMPLE 10

Transcriptome Analysis

The influence of APIT on the gene expression of tumor cells was investigated by Microarray technology.

In situ Oligonucleotide Arrays.

A custom oligonucleotide glass array of specific 60 mer oligonucleotides representing the mRNA of about 8500 human genes was designed based on human Unigene clusters (Unigene build No. 148) including positive and negative control oligonucleotides (*Homo sapiens* house keeping genes and *Arabadopsis thaliana* genes respectively). The probe design included a base composition filter and a homology search to minimise cross-hybridisation.

RNA Isolation, Labelling and Hybridisation to Arrays.

Jurkat neo cells ($1 \times 10^7$ in 20 ml) were cultured for 2 hours in medium (RPMI+10% FCS) in the presence or absence of APIT (10 ng/ml) at 37° C., 5% $CO_2$. Cells were harvested and the pellet was dissolved in 2 ml Trizol (Life Technologies). Total RNA was extracted after addition of chloroform and subsequent centrifugation and precipitated with isopropanol. After washing the pellet with 75% ethanol it was briefly air-dried. Quality control of the RNA included exclusion of genomic DNA by PCR and "Lab on a chip technology" (Bioanalyser). RNA (5 µg) from each pool was amplified using a reverse transcriptase/T7 polymerase. 1.5 µg of test cRNAs labelled either with Cy3 or Cy5 were hybridised for 16 hours at 65° C. to arrays. Each sample was also labelled and hybridised with the reverse fluorophore to obviate possible dye bias. Slides were scanned using a Microarray scanner. Background signal was determined using negative control spots and subtracted, data were normalised relative to non-regulated genes. Data from duplicate hybridizations were combined.

Results.

Tables 4 and 5 summarize the genes with increased or decreased transcription rate of treated cells compared with untreated cells, indicating these genes and/or its gene products (proteins) to be targets of APIT and/or $H_2O_2$.

EXAMPLE 11

Knock Down of Prx I Sensitized Tumor Cells for APIT Induced Cell Death

Peroxiredoxin I (Prx I) exhibited the most significant modification observed in 2-DE protein patterns of APIT treated cells in comparison to untreated Jurkat cells (Table 3). The modification of Prx I which is observed in 2-DE gel analysis of APIT treated cells resembles that described for the oxidized and inactivated Prx I, indicating that APIT inactivates this detoxification system. In order to investigate the role of Prx I for the APIT induced cell death we performed knock down of Prx I expression by RNA interference (RNAi). If Prx I was involved in the detoxification of $H_2O_2$ produced by APIT, we expected to observe a sensitization in cells in which Prx I expression is decreased.

Therefore, 20.000 HeLa cells/well were seeded in a 96 well plate one day prior to transfection. Transfection was performed with 0.25 µg siRNA directed against Prx I having the sequence (SEQ ID NO: 9):

```
5'-GGCUGAUGAAGGCAUCUCGdTdT-3'      (SEQ ID NO: 73)

3'-dTdTCCGACUACUUCCGUAGAGC-5',
```

Lamin A/C having the sequence (SEQ ID NO: 30):

```
5'-CUGGACUUCCAGAAGAACAdTdT         (SEQ ID NO: 74)

3'-dTdTGACCUGAAGGUCUUCUUGU-5',
``` and Luciferase having the sequence (SEQ ID NO: 31):

```
5'-CUUACGCUGAGUACUUCGAdTdT-3'      (SEQ ID NO: 75)

3'-dTdTGAAUGCGACUCAUGAAGCU-5',
``` as control and 2 il transmessenger per well using the transmessenger transfection kit (Qiagen, Hilden, Germany) according to manufacturers instructions. For APIT treatment (40 ng/ml) transfections were conducted in triplicates. 24 h after transfection cells were splitted and grown for additional 48 h before fresh medium with or without APIT was added for 6 h. Assay conditions which led to a 50 to 70% reduction of the metabolic activity of treated cells were chosen for RNAi experiments. Metabolic activity was determined as described in Example 2. In parallel, RNA from about 50.000 cells was isolated using the RNeasy 96 BioRobot 8000 system (Qiagen) 48 h after transfection. The relative amount of mRNA was determined by realtime PCR using Quantitect™ SYBR Green RT-PCR Kit from Qiagen following manufacturers instructions. The expression level of Prx mRNA was normalised against the internal standard GAPDH. The following primers were used: Prx I 5': CTGTTATGCCAGATG-GTCAG (SEQ ID NO: 67), Prx I 3': GATACCAAAGGAAT- GTTCATG (SEQ ID NO: 68), Lamin A/C5′: CAAGAAGGAGGGTGACCTGA (SEQ ID NO: 69), Lamin A/C3′:GCATCTCATCCTGAAGTTGCTT (SEQ ID NO: 70), GAPDH 5′:GGTATCGTGGAAGGACTCATGAC (SEQ ID NO: 71), GAPDH 3′:ATGCCAGTGAGCTTC-CCGTTCAG (SEQ ID NO: 72).

Figure 8A:
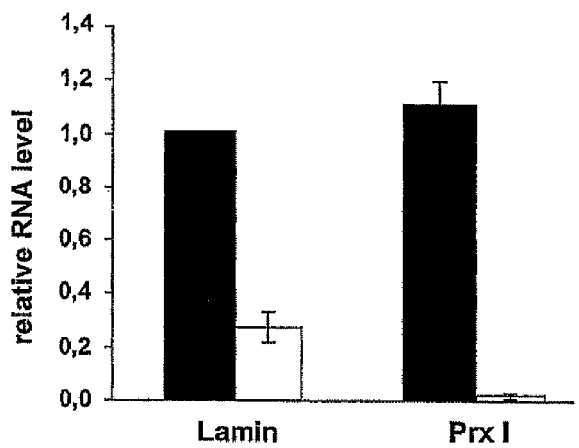
Figure 8B:
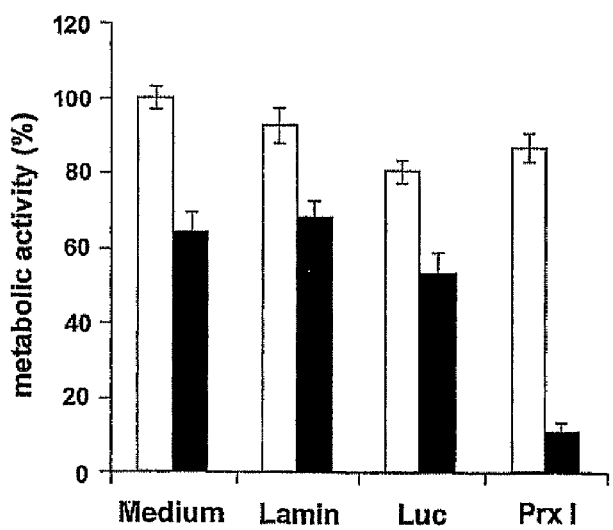

To measure sensitization, conditions were chosen under which the reduction of metabolic activity of treated cells was 50% or less of the untreated cells. siRNAs were transfected into HeLa cells and after 72 h cells were treated with APIT for 6 h and metabolic activity was determined. In parallel, cells were harvested for quantitative analysis of the respective mRNAs by realtime PCR (FIG. 8 A). The mRNA of Prx I was reduced by more than 90% compared to the mRNA level of GAPDH. Interestingly, this reduction of Prx I expression significantly sensitized the cells for killing by APIT whereas control siRNA directed against Luciferase and Lamin A/C had no effect (FIG. 8 B). Our data show that knock down of Prx I by RNAi rendered the cells hypersensitive for APIT suggesting that Prx I is part of an $H_2O_2$ detoxifying pathway which is modulated by APIT.

In summary, we identified the modification of Prx I, as an important step in the APIT of this detoxification system. The fact that the knock down of Prx I expression by RNAi increased the sensitivity of tumor cells for the cytolytic activity of APIT underlines the impact of Prx I RNA interference for cancer therapy.

EXAMPLE 12

APIT Does Not Induce Actin Depolymerisation

Cyplasin S and L, proteins from *Aplysia punctata* which induce cell death of tumor cells were described to cause fast actin depolymerisation in human tumor cells (see WO 03/057726). The influence of APIT treatment on actin filaments by fluorescence staining of actin by Phalloidin-TRITC (Tetramethylrhodamin-isothiocyanat) is investigated.

HeLa cells (1.5×105 cells/well/ml) were cultured over night on cover slips in 12 well plates. Subsequently, cells were incubated in the presence or absence of APIT (40 ng/ml) for 6 h or Cytochalasin D (1 ìM; Sigma 8273) for 30 min. After washing in PBS, cells on cover slips were fixed for 10 min in 3.7% PFA (paraformaldehyde), washed again and finally permeabilized by a 1 min incubation in 0.5% Triton X-100. Blocking of unspecific binding sites by incubation in PBS, 1% FCS, 0.05% Tween 20 was followed by actin staining with Phalloidin-TRITC in blocking puffer for 15 min and 3 fold washing. Nuclei were stained by the presence of Hoechst 33258 in the last washing step. Cover slips were investigated by fluorescence microscopy.

Figure 9A:
Figure 9B:
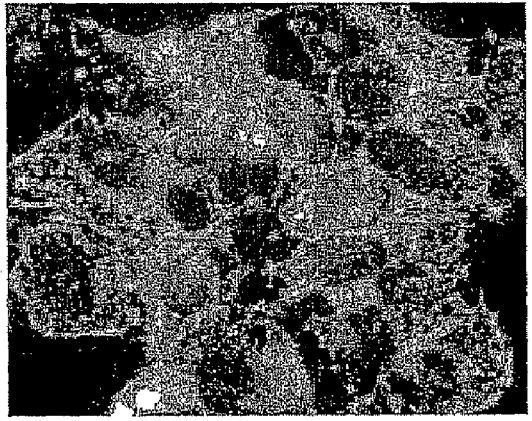
Figure 9C:
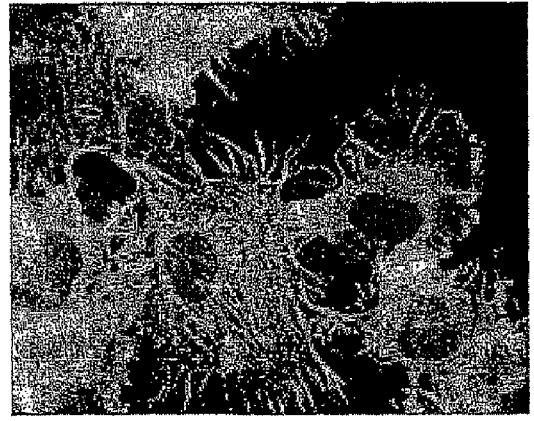

As shown in FIG. 9 untreated cells (A) possess a typical actin cytoskeleton. Incubation in the presence of Cytochalasin (B), an inducer of rapid actin depolymerisation, resulted in a massive loss of actin filaments and an accumulation of actin in clumps. In contrast, APIT(C) did not induce actin depolymerisation in HeLa cells. APIT treated cells remain their actin filaments, even after 6 h when the plasma membrane was already disrupted (see example 2, FIG. 2D). This clearly differentiates APIT induced cell death from that induced by Cyplasins.

EXAMPLE 13

Healthy Human Cells are Resistant Against the APIT-Induced Cell Death

To analyze the specificity of APIT for tumor cells, normal human umbilical vein endothelial cells (HUVEC) and tumor cells (Jurkat cells) were incubated with increasing amounts of purified APIT and analyzed for lactate dehydrogenase (LDH) release (FIG. 10).

HUVEC and Jurkat cells (50,000 cells/100 ìl/wells) were treated with increasing amounts of APIT in a 96 well plate. After over night incubation half of the culture supernatants (50 ìl) were transferred in fresh wells and mixed with 50ìl reagent of Cytotoxicity Detection Kit-LDH according to the manufacturers instruction (Roche 1644793). Release of LDH in the supernatant is found only, when cells were killed by APIT. LDH release was calculated as the ratio of LDH activity of APIT treated cells relative to the LDH activity of Triton X 100 lysed cells.

Jurkat cells showed a dramatic release of LDH upon incubation with APIT (FIG. 10). In contrast, even at the highest APIT concentrations used in this experiments (40 ng/ml), APIT treated HUVEC cells only showed a minor LDH release below 10%, indicating a strong resistance of these normal cells against the cytolytic activity of APIT. As several tumor cell lines showed a similar APIT sensitivity as the Jurkat cells (Table 2), the data suggest the toxic effect induced by APIT is tumor specific.

TABLE 1

| EAA (essential amino acids) | |
|---|---|
| L-arainine•HCl | 126.4 mg/l |
| L-cystine | 24.02 mg/l |
| L-histidine•HCl•H2O | 41.92 mg/l |
| L-isoleucine | 52.46 mg/l |
| L-leucine | 52.46 mg/l |
| L-lysine•HCl | 73.06 mg/l |
| L-methionine | 14.92 mg/l |
| L-phenylalanine | 33.02 mg/l |
| L-threonine | 47.64 mg/l |
| L-tryptophane | 10.2 mg/l |
| L-tyrosine | 36.22 mg/l |
| L-valine | 46.86 mg/l |
| NEAA (non-essential aino acids) | |
| L-alanine | 8.9 mg/l |
| L-asparagine | 13.2 mg/l |
| L-aspartic-acid | 13.3 mg/l |
| L-alutamic acid | 14.7 mg/l |
| glycine | 7.5 mg/l |
| L-prolin | 11.5 mg/l |
| L-serine | 10.5 mg/l |
| Single amino acids | |
| histidine•HCl•H2O | 20 mg/l |
| isoleucine | 50 mg/l |
| leucine | 50 mg/l |
| methionine | 15 mg/l |
| phenylalanine | 15 mg/l |
| threonine | 20 mg/l |
| tyrosine | 20 mg/l |
| arginine•HCl | 240 mg/l |
| lysine | 40 mg/l |
| D-lysine | 40 mg/l |
| cystine | 50 mg/l |
| tryptophane | 5 mg/l |
| valine | 20 mg/l |
| glutamine | 300 mg/l |

TABLE 2

APIT kills different tumor cell lines

| models for | kind of tumor | tumor cell line | IC50 (ng/ml) |
|---|---|---|---|
| 1. solid tumors | lung cancer | GLC4 | 9 |
| | breast cancer | MCF-7, SK-BR-3 | * |
| | prostate cancer | PC3, DU145 | * |
| | colon cancer | HT-29 | 20 |
| | cervix cancer | HeLa, Chang | *, 10 |
| | uterus carcinoma | Hec-1-B | * |
| | larynx cancer | HEp-2 | * |
| | stomach cancer | AGS | * |
| | liver cancer | Hep G2 | * |
| 2. leukemia | T cell leukemia (ALL) | Jurkat neo | 3.2 |
| | T cell leukemia (ALL) | CEM neo | 5.6 |
| | B cell leukemia | SKW neo | 3 |
| | Monocyte leukemia (AML) | Mono Mac 6 | * |
| | Monocyte leukemia (AML) | THP-1 | 10 |
| 3. "orphan" tumors | Ewings sarcoma | RDES | 4.5 |
| | | A673 | 5 |
| 4. apoptosis resistant tumors | (CML) | K562 | 4.25 |
| | T cell leukemia (ALL) | Jurkat Bcl-2 | 2.7 |
| | T cell leukemia (ALL) | CEM Bcl-$X_L$ | 4.0 |
| | B cell leukemia | SKW Bcl-2 | 5.5 |
| 5. MDR tumors | Lung cancer | GLC4-ADR | 10 |

TABLE 3

Proteome analysis

| Description | gi | NCBI | NCBI version | swissprot | effect |
|---|---|---|---|---|---|
| Aldolase A (E.C.4.1.2.13) | 229674 | 1ALD | 1ALD | P04075 | |
| 26S proteasome regulatory chain 12 | 2134660 | S65491 | S65491 | — | − |
| 3-Hydroxyacyl-CoA dehydrogenase | 2078327 | AAB54008 | AAB54008.1 | Q16836 | − |
| C-1-tetrahydrofolate synthase, cytoplasmic (C1-THF synthase) | 115206 | P11586 | P11586 | P11586 | − |
| Chain A, Structure Of Human Glutamate Dehydrogenase-Apo Form | 20151189 | 1L1F_A | 1L1F_A | — | m |
| or Glutamate dehydrogenase 1 | 4885281 | NP_005262 | NP_005262.1 | P00367 | |
| Cleavage and polyadenylation specific factor 5, 25 kD subunit | 5901926 | NP_008937 | NP_008937.1 | | + |
| Cofilin 1 | 5031635 | NP_005498 | NP_005498.1 | P23528 | − |
| Coronin, actin binding protein, 1A | 5902134 | NP_009005 | NP_009005.1 | P31146 | + |
| Dihydrolipoamide dehydrogenase precursor; E3 component of pyruvate dehydrogenase | 4557525 | NP_000099 | NP_000099.1 | P09822 | − |
| dJ553F4.4 (Novel protein similar to Drosophila CG8055 protein) | 12314022 | CAC14088 | CAC14088.1 | | + |
| DNA replication licensing factor MCM4 | 1705520 | | | P33991 | + |
| Elongation factor1-delta (EF-1-delta) | 20141357 | P29692 | P29692 | P29692 | − |
| Enolase 1, alpha; phosphopyruvate hydratase | 4503571 | NP_001419 | NP_001419.1 | Q05524 | + |
| Glyceraldehyde-3-phosphate dehydrogenase | 31645 | CAA25833 | CAA25833.1 | P04406* | + |
| or uracil DNAglycosylase | 35053 | CAA37794 | CAA37794.1 | P04406* | |
| Heat shock 60 kD protein 1 (chaperonin) | 14603309 | AAH10112 | AAH10112.1 | Q96FZ6 | − |
| Heat shock 60 kDa protein 1 (chaperonin) | 4504521 | NP_002147 | NP_002147.1 | P10809 | − |
| Heat shock 70 kD protein 9B (mortalin-2) | 4756570 | NP_004125 | NP_004125.1 | Q8N1C8 | − |
| Heterogeneous nuclear ribonucleoprotein C, isoform b | 4758544 | NP_004491 | NP_004491.1 | P07910 | m |
| Hspc117 | 6841456 | AAF29081 | AAF29081.1 | Q9P037 | m |
| Inosine-5'-monophosphate dehydrogenase 2 (IMP dehydrogenase 2) | 124419 | P12268 | P12268 | P12268 | + |
| Isocitrate dehydrogenase 3 (NAD+) alpha | 5031777 | NP_005521 | NP_005521.1 | P50213 | − |
| KH-type splicing regulatory protein (FUSE binding protein 2) | 4504851 | NP_003676 | NP_003676.1 | — | − |
| Nuclear matrix protein NMP200 related to splicing factor PRP19 | 7657381 | NP_055317 | NP_055317.1 | Q9UMS4 | − |
| Nucleobindin 2 | 4826870 | NP_005004 | NP_005004.1 | P80303 | − |
| 54 kDa nuclear RNA- and DNA-binding protein (p54(nrb)) (p54nrb) | 13124797 | Q15233 | Q15233 | Q15233 | + |
| Peroxiredoxin 1 (Thioredoxin peroxidase 2) | 548453 | Q06830 | Q06830 | Q06830 | m |
| Peroxiredoxin 1; Proliferation-associated gene A; proliferation-associated gene A | 4505591 | NP_002565.1 | NP_002565.1 | Q06830 | m |
| Peroxiredoxin 2 (Thioredoxin peroxidase 1) | 2507169 | P32119 | P32119 | P32119 | + |
| Peroxiredoxin 3; antioxidant protein 1; thioredoxin-dependent peroxide reductase precursor | 5802974 | NP_006784 | NP_006784.1 | P30048 | − |
| 2-phosphopyruvate-hydratase alpha-enolase; carbonate dehydratase | 693933 | CAA59331 | CAA59331.1 | P06733 | + |
| Proteasome subunit alpha type 7 | 12643540 | O14818 | O14818 | O14818 | + |
| Proteasome subunit beta type 1 (Proteasome component C5) (Macropain subunit C5) | 130853 | P20618 | P20618 | P20618 | + |
| Ras-GTPase-activating protein SH3-domain-binding protein; GAP binding protein | 5031703 | NP_005745.1 | NP_005745.1 | Q13283 | m |
| Replication protein A2, 32 kDa | 4506585 | NP_002937 | NP_002937.1 | P15927 | − |
| Rho GDP-dissociation inhibitor 2 (Rho GDI 2) (Rho-GDI beta) (Ly-GDI) | 1707893 | P52586 | P52566 | P52566 | − |
| Ribosomal protein P0; 60S acidic ribosomal protein P0 | 4506667 | NP_000993 | NP_00993.1 | P05388 | |
| or similar BLOCK 23 | 20536934 | XP_165448 | XP_165448.1 | Q8NHW5 | |
| Ribosomal protein, large, P0 | 12654583 | AAH01127 | AAH01127.1 | P05388 | − |
| RNA-binding protein regulatory subunit | 6005749 | NP_009193 | NP_009193.1 | O14805 | + |
| RNA-binding protein regulatory subunit | 12720028 | XP_001707 | XP_001707.2 | O14805 | + |

TABLE 3-continued

Proteome analysis

| Description | gi | NCBI | NCBI version | swissprot | effect |
|---|---|---|---|---|---|
| Semenogelin I; Semenogelin | 4506883 | NP_002998 | NP_002998.1 | P04279 | − |
| Similar to villin 2 (ezrin) | 15530243 | AAH13903 | AAH13903.1 | P15311 | − |
| Splicing factor proline/glutamine rich (polypyrimidine tract binding protein associated) | 4826998 | NP_005057 | NP_005057.1 | P23246 | − |
| Stathmin 1; metablastin; prosolin; oncoprotein 18; phosphoprotein 19; leukemia-associated phosphoprotein p18 | 5031851 | NP_005554 | NP_005554.1 | | − |
| U2 small nuclear ribonucleoprotein A' (UZ snRNP-A') | 134094 | P09661 | P09661 | P09661 | + |
| Vimentin | 4507895 | NP_003371 | NP_003371.1 | P08670 | − |
| Voltage-dependent anion-selective channel protein 2 (VDAC-2) (hVDAC2) | 1172554 | P45880 | P45880 | P45880 | − |

TABLE 4

Transcriptome analysis

| Unigene cluster | Description | GENE | gi | pir/NCBI/swissprot | effect |
|---|---|---|---|---|---|
| Hs.3833 | 3'-phosphoadenosine 5'-phosphosulfate synthase 1 | PAPSS1 | 4885537 | NP_005434.1 | − |
| Hs.166563 | replication factor C (activator 1) 1, 145 kDa | RFC1 | 15011931 | ref:NP_002904.2 | − |
| Hs.78991 | DNA segment, numerous copies, expressed probes (GS1 gene) | DXF68S1E | 6912346 | ref:NP_036212.1 | − |
| Hs.326035 | early growth response 1 | EGR1 | 119242 | sp:P18146 | ++ |
| Hs.108885 | collagen, type VI, alpha 1 | COL6A1 | 15011913 | ref:NP_001839.1 | ++ |
| Hs.78944 | regulator of G-protein signalling 2, 24 kDa | RGS2 | 2135146 | pir:I53020 | ++ |
| Hs.110571 | growth arrest and DNA-damage-inducible, beta | GADD45B | 9945332 | ref:NP_056490.1 | ++ |
| Hs.78465 | v-jun sarcoma virus 17 oncogene homolog (avian) | JUN | 135298 | sp:P05412 | + |
| Hs.82646 | DnaJ (Hsp40) homolog, subfmally B, member 1 | DNAJB1 | 1706473 | sp:P25685 | + |
| Hs.169840 | TTK protein kinase | TTK | 346403 | pir:A42861 | + |
| Hs.211601 | mitogen-activated protein kinase kinase kinase 12 | MAP3K12 | 18202489 | sp:Q12852 | + |
| Hs.345728 | suppressor of cytokine signaling 3 | SSI-3 | 4507235 | ref:NP_003946.1 | + |
| Hs.3776 | zinc finger protein 216 | ZNF216 | 5174755 | ref:NP_005998.1 | + |
| Hs.73037 | cannabinoid receptor 2 (macrophage) | CNR2 | 450068 | prf:1920360A | + |
| Hs.167578 | EST, FLJ25357 hypothetical protein FLJ25357 | | 740170 | 2004399A | + |
| Hs.8715 | hypothetical protein MGC3232 | MGC3232 | 3024681 | sp:O00268 | + |
| Hs.74520 | spinocerebellar ataxia 1 (olivopontocerebellar ataxia 1, autosomal dominant, ataxin 1) | SCA1 | 1082237 | pir:S46268 | + |
| Hs.6151 | pumilio homolog 2 (*Drosophila*) | PUM2 | 14277945 | pdb:1IB3 | + |
| Hs.8026 | EST, Highly similar to SES2_HUMAN Sestrin 2 [*H. sapiens*] | | 13633882 | sp:P58004 | + |
| Hs.82173 | TGFB inducible early growth response | TIEG | 11387050 | sp:Q13118 | + |
| Hs.198307 | von Hippel-Lindau binding protein 1 | VBP1 | 4507873 | ref:NP_003363.1 | + |
| Hs.179982 | tumor protein p53-binding protein | TP53BPL | 5032191 | ref:NP_005793.1 | + |
| Hs.2549 | adrenergic, beta-3-, receptor | ADRB3 | 1070630 | pir:QRHUBE | + |
| Hs.2128 | dual specificity phosphatase 5 | DUSP5 | 12707566 | ref:NP_004410.2 | + |
| Hs.36927 | heat shock 105 kD | HSP105B | 5729879 | ref:NP_006635.1 | + |
| Hs.77558 | high mobility group nucleosomal binding domain 3 | HMGN3 | 2495254 | sp:Q15651 | + |
| Hs.460 | activating transcription factor 3 | ATF3 | 88875 | pir:C34223 | + |
| Hs.104125 | adenylyl cyclase-associated protein | CAP | 399184 | sp:Q01518 | + |
| Hs.24719 | modulator of apoptosis 1 | MAP-1 | 11545896 | ref:NP_071434.1 | + |
| Hs.8257 | cytokine inducible SH2-containing protein | CISH | 13124022 | sp:Q9NSE2 | + |
| Hs.101383 | ESTs, Weakly similar to A43932 mucin 2 precursor, intestinal - human (fragments) | | 2135765 | pir:A43932 | + |
| Hs.276770 | CDW52 antigen (CAMPATH-1 antigen) | CDW52 | 4502761 | ref:NP_001794.1 | + |
| Hs.8084 | hypothetical protein dJ465N24.2.1 | DJ465N24.2.1 | 10092679 | ref:NP_064713.1 | + |
| Hs.78829 | ubiquitin specific protease 10 | USP10 | 11360280 | pir:T47164 | + |
| Hs.889 | Charot-Leyden crystal protein | CLC | 1942861 | pdb:1LCL | + |
| Hs.277401 | bromodomain adjacent to zinc finger domain, 2A | BAZ2A | 7304921 | ref:NP_038477.1 | + |
| Hs.300863 | lethal (3) malignant brain tumor l(3)mbt protein (*Drosophila*) homolog | H-L(3)M8T | 14141728 | ref:NP_056293.2 | + |
| Hs.4552 | ubiquilin 2 | UBQLN2 | 16753207 | ref:NP_038472.2 | + |
| Hs.151963 | GrpE-like protein cochaperone | HMGE | 18202951 | sp:Q9HAV7 | + |
| Hs.36606 | EST, Weakly similar to T29982 hypothetical protein F11G11.12 - [*C. elegans*] | | | | + |
| HS.85302 | adenosine deaminase, RNA-specific, B1 (RED1 homolog rat) | ADARB1 | 2829669 | sp:P78563 | + |
| Hs.113823 | ClpX caseinotytic protease X homolog (*E. coli*) | CLPX | 14916956 | sp:O76031 | + |
| Hs.25911 | HLA-B associated transcript 2 | BAT2 | 18375626 | ref:NP_542417.1 | + |
| Hs.95821 | osteoclast stimulating factor 1 | OSTF1 | 11134088 | sp:Q92882 | + |
| Hs.11217 | KIAA0877 protein | KIAA0877 | | | + |
| Hs.301064 | arfaptin 1 | HSU52521 | 1703203 | sp:P53367 | + |
| Hs.276238 | EST, Moderately similar to kinase suppressor of ras [(*Mus musculus*)] | | | | + |
| Hs.211569 | G protein-coupled receptor kinase 5 | GPRK5 | 2135145 | pir:A48277 | + |
| Hs.25524 | protein tyrosine phosphatase, non-receptor type 23 | PTPN23 | 7512735 | pir:T14756 | + |
| Hs.94498 | leukocyte immunoglobulin-like receptor, subfamily A (with TM domain), member 2 | LILRA2 | 5803068 | ref:NP_006857.1 | + |

TABLE 4-continued

Transcriptome analysis

| Unigene cluster | Description | GENE | gi | pir/NCBI/swissprot | effect |
|---|---|---|---|---|---|
| Hs.24427 | DKFZP566O1646 protein | DC8 | 7512839 | pir:T08737 | + |
| Hs.46 | platelet-activating factor receptor | PTAFR | 107346 | pir:A40191 | + |
| Hs.90800 | EST, Highly similar to matrix metalloproteinase 16, isoform 1; membrane-type matrix metalloproteinase 3; membrane-type-3 matrix metalloproteinase [Homo sapiens] | | 13027802 | ref:NP_005932.2 | + |
| Hs.81648 | hypothetical protein FLJ11021 similar to splicing factor, arginine/serine-rich 4 | FLJ11021 | 2833266 | sp:Q15696 | + |
| Hs.80338 | Bcl-2-associated transcription factor | BTF | 7661958 | ref:NP_055554.1 | + |
| Hs.238407 | EST, Weakly similar to hypothetical protein FLJ20489 [Homo sapiens] [H. sapiens] | | 8923452 | ref:NP_060312.1 | + |
| Hs.154668 | KIAA0391 gene product | KIAA0391 | 3024899 | sp:O15091 | + |
| Hs.76666 | chromosome 9 open reading frame 10 | C9orf10 | 13431358 | sp:Q9NZB2 | + |
| Hs.9701 | growth arrest and DNA-damage-inducible, gamma | GADD45G | 5729836 | ref:NP_006696.1 | + |
| Hs.100527 | connector enhancer of KSR2 | CNK2 | 7662368 | ref:NP_055742.1 | + |
| Hs.77274 | plasminogen activator, urokinase | PLAU | 224665 | prf:1110198A | + |
| Hs.93516 | ESTs | | | | + |
| Hs.376709 | Homo sapiens cDNA FLJ33768 fis, clone BRHIP2000021 | | | | + |
| Hs.110299 | mitogen-activated protein kinase kinase 7 | MAP2K7 | 4826946 | ref:NP_005034.1 | + |
| Hs.31396 | ESTs, Weakly similar to S28807 collagen alpha 1(X) chain precursor [M. musculus] | | | | + |
| Hs.129715 | gonadatropin-releasing hormone 2 | GNRH2 | 3913735 | sp:O43555 | + |
| Hs.169370 | FYN oncogene related to SRC, FGR, YES | FYN | 125370 | sp:P06241 | + |
| Hs.82007 | methionyl aminopeptidase 1 | METAP1 | 1703270 | sp:P53582 | + |
| Hs.239018 | RAB11B, member RAS oncogene family | RA811B | 1082426 | pir:JC2487 | + |
| Hs.126852 | solute carrier family 6 (neurotransmitter transporter, GABA), member 13 | SLC6A13 | 7705539 | ref:NP_057699.1 | + |

TABLE 5

Transcriptome analysis

| GENBANK | GENENAME | SYMBOL | EFFECT |
|---|---|---|---|
| NM_005252 | v-fos FBJ murine osteosarcoma viral oncogene homolog | FOS | ++ |
| NM_006705 | growth arrest and DNA-damage-inducible, gamma | GADD45G * | ++ |
| NM_001964 | early growth response 1 | EGR1 * | ++ |
| NM_002228 | v-jun sarcoma virus 17 oncogene homolog (avian) | JUN * | ++ |
| NM_015675 | growth arrest and DNA-damage-inducible, beta | GADD45B * | ++ |
| NM_001124 | adrenomedullin | ADM | ++ |
| NM_005346 | heat shock 70 kDa protein 1B | HSPA1B | ++ |
| NM_002166 | inhibitor of DNA binding 2, dominant negative helix-loop-helix protein | ID2 | ++ |
| NM_004417 | dual specificity phosphatase 1 | DUSP1 | ++ |
| NM_003745 | suppressor of cytokine signaling 1 | SOCS1 | ++ |
| NM_002923 | regulator of G-protein signalling 2, 24 kDa | RGS2 * | ++ |
| NM_005627 | serum/glucocorticoid regulated kinase | SGK | ++ |
| BC012321 | activity-regulated cytoskeleton-associated protein | ARC | ++ |
| NM_025195 | phosphoprotein regulated by mitogenic pathways | C8FW | + |
| NM_030751 | transcription factor 8 (represses interleukin 2 expression) | TCF8 | + |
| NM_014330 | protein phosphatase 1, regulatory (inhibitor) subunit 15A | PPP1R15A | + |
| NM_004083 | DNA-damage-inducible transcript 3 | DDIT3 | + |
| NM_001841 | cannabinoid receptor 2 (macrophage) | CNR2 * | + |
| NM_004024 | activating transcription factor 3 | ATF3 * | + |
| NM_001706 | B-cell CLL/lymphoma 6 (zinc finger protein 51) | BCL6 | + |
| NM_004428 | ephrin-A1 | EFNA1 * | + |
| NM_004419 | dual specificity phosphatase 5 | DUSP5 * | + |
| NM_003088 | fascin homolog 1, actin-bundling protein (Strongylocentrotus purpuratus) | FSCN1 | + |
| AB014566 | dishevelled associated activator of morphogenesis 1 | DAAM1 | + |
| NM_006145 | DnaJ (Hsp40) homolog, subfmaily B, member 1 | DNAJB1 * | + |
| NM_004962 | growth differentiation factor 10 | GDF10 | + |
| D79994 | kidney ankyrin repeat-containing protein | KANK | + |
| NM_006301 | mitogen-activated protein kinase kinase kinase 12 | MAP3K12 * | + |
| NM_002928 | regulator of G-protein signalling 16 | RGS16 | + |
| NM_003955 | suppressor of cytokine signaling 3 | SOCS3 | + |
| NM_004430 | early growth response 3 | EGR3 | + |
| NM_001731 | B-cell translocation gene 1, anti-proliferative | BTG1 | + |
| NM_012342 | putative transmembrane protein | NMA | + |
| NM_002262 | killer cell lectin-like receptor subfamily D, member 1 | KLRD1 | + |
| NM_006007 | zinc finger protein 216 | ZNF216 * | + |
| NM_000905 | neuropeptide Y | NPY | + |
| NM_004418 | dual specificity phosphatase 2 | DUSP2 | + |
| NM_031459 | sestrin 2 | SES2 | + |
| AF332558 | BCL2 binding component 3 | BBC3 | + |
| NM_006000 | tubulin, alpha 1 (testis specific) | TUBA1 | + |
| NM_006644 | heat shock 105 kDa/110 kDa protein 1 | HSPH1 | + |

TABLE 5-continued

Transcriptome analysis

| GENBANK | GENENAME | SYMBOL | EFFECT |
|---|---|---|---|
| L24498 | growth arrest and DNA-damage-inducible, alpha | GADD45A | + |
| AK024029 | modulator of apoptosis 1 | MOAP1 | + |
| NM_005409 | chemokine (C-X-C motif) ligand 11 | CXCL11 | + |
| NM_003383 | very low density lipoprotein receptor | VLDLR | + |
| AF267856 | hypothetical protein dJ465N24.2.1 | DJ465N24.2.1 * | + |
| NM_002450 | metallothionein 1L | MT1L | + |
| NM_001828 | Charot-Leyden crystal protein | CLC * | + |
| NM_013370 | pregnancy-induced growth inhibitor | OKL38 | + |
| AB014581 | l(3)mbt-like (Drosophila) | L3MBTL | + |
| NM_0008875 | pim-2 oncogene | PIM2 | + |
| AL031695 | actin, gamma pseudogene 3 | AGTGP3 | + |
| AI985514 | ribosomal protein S19 | RPS19 | + |
| NM_080686 | HLA-B associated transcript 2 | BAT2 | + |
| NM_021184 | chromosome 6 open reading frame 47 | C6orf47 | + |
| NM_015471 | DKFZP566O1646 protein | DCS * | + |
| NM_000952 | platelet-activating factor receptor | PTAFR | + |
| BC012625 | protein phosphatase 1, regulatory (inhibitor) subunit 3C | PPP1R3C | + |
| NM_023012 | hypothetical protein FLJ11021 similar to splicing factor, arginine/serine-rich 4 | FLJ11021 * | + |
| AK024358 | macrophage expressed gene 1 | LOC219972 | + |
| NM_002658 | plasminogen activator, urokinase | PLAU * | + |
| U12767 | nuclear receptor subfamily 4, group A, member 3 | NR4A3 | + |
| NM_016615 | solute carrier family 6 (neurotransmitter transporter, GABA), member 13 | SLC6A13 | + |
| NM_002135 | nuclear receptor subfamily 4, group A, member 1 | NR4A1 | + |
| AJ251595 | CD44 antigen (homing function and Indian blood group system) | CD44 | − |
| NM_005433 | v-yes-1 Yamaguchi sarcoma viral oncogene homolog 1 | YES1 | − |
| NM_006325 | RAN, member RAS oncogene family | RAN | − |
| NM_004775 | UDP-Gal:betaGlcNAc beta 1,4-galactosyltransferase, polypeptide 6 | B4GALT6 | − |
| AK056671 | upstream regulatory element binding protein 1 | UREB1 | − |
| NM_022817 | period homolog 2 (Drosophila) | PER2 | − |
| L07044 | calcium/calmodullin-dependent protein kinase (CaM kinase) II gamma | CAMK2G | − |
| NM_014890 | downregulated in ovarian cancer 1 | DOC1 | − |
| NM_001782 | CD72 antigen | CD72 | − |
| NM_005766 | FERM, RhoGEF (ARHGEF) and pleckstrin domain protein 1 (chondrocyte-derived) | FARP1 | − |
| NM_000566 | Fc fragment of IgG, high affinity Ia, receptor for (CD64) | FCGR1A | − |
| NM_003036 | v-ski sarcoma viral oncogene homolog (avian) | SKI | − |
| NM_001713 | betaine-homocysteine methyltransferase | BHMT | − |
| NM_001682 | ATPase, Ca++ transporting, plasma membrane 1 | ATP2B1 | − |
| NM_003985 | tyrosine kinase, non-receptor, 1 | TNK1 | − |
| NM_004752 | glial cells missing homolog 2 (Drosophila) | GCM2 | − |
| BC001619 | aldehyde dehydrogenase 1 family, member B1 | ALDH1B1 | − |
| NM_002422 | matrix metalloproteinase 3 (stromelysin 1, progelatinase) | MMP3 | − |
| NM_003024 | intersectin 1 (SH3 domain protein) | ITSN1 | − |
| NM_002613 | 3-phosphoinositide dependent protein kinase-1 | PDPK1 | − |
| NM_000098 | carnitine palmitoyltransferase II | CPT2 | − |
| BC002712 | v-myc myelocytomatosis viral related oncogene, neuroblastoma derived (avian) | MYCN | − |
| NM_003112 | Sp4 transcription factor | SP4 | − |
| NM_012062 | dynamin 1-like | DNM1L | − |
| NM_000880 | interleukin 7 | IL7 | − |
| NM_004564 | PET112-like (yeast) | PET112L | − |
| NM_001771 | CD22 antigen | CD22 | − |
| AA904067 | protein phosphatase 1, regulatory (inhibitor) subunit 12B | PPP1R12B | − |
| NM_001633 | alpha-1-microglobulin/bikunin precursor | AMBP | − |
| NM_007216 | Hermansky-Pudlak syndrome 5 | HPS5 | − |
| AV708310 | protein phosphatase 2 (formerly 2A), catalytic subunit, alpha isoform | PPP2CA | − |
| AF296765 | cerebral cavernous malformations 1 | CCM1 | − |
| AF155117 | kinesin family member 21A | KIF21A | − |
| NM_002006 | fibroblast growth factor 2 (basic) | FGF2 | − |
| NM_004362 | calmegin | CLGN | − |
| NM_021221 | lymphocyte antigen 6 complex, locus G5B | LY6G5B | − |
| AK001541 | secretory carrier membrane protein 1 | SCAMP1 | − |
| H08291 | acid phosphatase 1, soluble | ACP1 | − |
| NM_014636 | Ral guanine nucleotide exchange factor RalGPS1A | RALGPS1A | − |
| NM_053006 | serine/threonine kinase 22B (spermiogenesis associated) | STK22B | − |
| NM_000220 | potassium inwardly-rectifying channel, subfamily J, member 1 | KCNJ1 | − |
| NM_000633 | B-cell CLL/lymphoma 2 | BCL2 | − |
| NM_003605 | O-linked N-acetylglucosamine (GlcNAc) transferase (UDP-N-acetylglucosamine:polypeptide-N-acetylglucosaminyl transferase) | OGT | − |
| NM_006114 | translocase of outer mitochondrial membrane 40 homolog (yeast) | TOMM40 | − |
| NM_013404 | mesothelin | MSLN | − |
| NM_020974 | signal peptide, CUB domain, EGF-like 2 | SCUBE2 | − |
| NM_000439 | proprotein convertase subtilisin/kexin type 1 | PCSK1 | − |
| NM_002035 | follicular lymphoma variant translocation 1 | FVT1 | − |
| AL136924 | Ras and Rab interactor 2 | RIN2 | − |
| NM_006020 | alkB, alkylation repair homolog (E. coli) | ALKBH | − |
| NM_005433 | v-yes-1 Yamaguchi sarcoma viral oncogene homolog 1 | YES1 | − |
| NM_003423 | zinc finger protein 43 (HTF6) | ZNF43 | − |

TABLE 5-continued

Transcriptome analysis

| GENBANK | GENENAME | SYMBOL | EFFECT |
| --- | --- | --- | --- |
| AF056490 | phosphodiesterase 8A | PDE8A | − |
| NM_033480 | F-box only protein 9 | FBXO9 | − |
| NM_022789 | interleukin 17E | IL17E | − |
| NM_007150 | zinc finger protein 185 (LIM domain) | ZNF185 | − |
| NM_017450 | BAI1-associated protein 2 | BAIAP2 | − |
| AB037762 | myelin expression factor 2 | MYEF2 | − |
| NM_003263 | toll-like receptor 1 | TLR1 | − |
| NM_001089 | ATP-binding cassette, sub-family A (ABC1), member 3 | ABCA3 | − |
| NM_018240 | kin of IRRE like (Drosophila) | KIRREL | − |
| NM_003827 | N-ethylmaleimide-sensitive factor attachment protein, alpha | NAPA | − |
| NM_003569 | syntaxin 7 | STX7 | − |
| AB046797 | KIAA1577 protein | KIAA1577 | − |
| AV723914 | hypothetical protein LOC164729 | LOC164729 | − |
| NM_015967 | protein tyrosine phosphatase, non-receptor type 22 (lymphoid) | PTPN22 | − |
| AB007892 | CDC5 cell division cycle 5-like (S. pombe) | CDC5L | − |
| NM_022907 | hypothetical protein FLJ23053 | FLJ23053 | − |
| NM_004379 | cAMP responsive element binding protein 1 | CREB1 | − |
| AB023198 | KIAA0981 protein | KIAA0981 | − |
| NM_024958 | chromosome 20 open reading frame 98 | C20orf98 | − |
| NM_001186 | BTB and CNC homology 1, basic leucine zipper transcription factor 1 | BACH1 | − |
| NM_014639 | KIAA0372 gene product | KIAA0372 | − |
| NM_024641 | mannosidase, endo-alpha | MANEA | − |
| AK056671 | upstream regulatory element binding protein 1 | UREB1 | − |
| NM_003618 | mitogen-activated protein kinase kinase kinase kinase 3 | MAP4K3 | − |
| NM_005443 | 3'-phosphoadenosine 5'-phosphosulfate synthase 1 | PAPSS1 * | − |
| NM_022781 | ring finger protein 38 | RNF38 | − |
| NM_003874 | CD84 antigen (leukocyte antigen) | CD84 | − |
| NM_000091 | collagen, type IV, alpha 3 (Goodpasture antigen) | COL4A3 | − |
| NM_000160 | glucagon receptor | GCGR | − |
| NM_006019 | phosphodiesterase 1A, calmodulin-dependent | PDE1A | − |
| NM_012080 | family with sequence similarity 16, member A, X-linked | FAM16AX | − |

The invention claimed is:

1. A method of treating cancer comprising the step of administering to a subject in need thereof a polypeptide comprising the amino acid sequence shown in SEQ ID NO: 2, 4, or 6.

2. The method according to claim 1 wherein said cancer is selected from the group consisting of lung cancer, breast cancer, prostate cancer, colon cancer, cervix cancer, uterus cancer, larynx cancer, stomach cancer, liver cancer, Ewings sarcoma, acute lymphoid leukemia, chronic myeloid leukemia, apoptosis resistant leukemia, MDR lung cancer, pancreas cancer, gastric cancer, kidney cancer, gliomas, melanomas, chronic lymphoid leukemia, and lymphoma.

3. A method of treating cancer comprising the step of administering to a subject in need thereof a composition comprising an effective amount of a polypeptide that comprises the amino acid sequence shown in SEQ ID NO: 2, 4, or 6 and a diluent, a carrier and/or an adjuvant.

4. The method of claim 1, wherein the polypeptide is produced recombinantly.

5. The method of claim 4, wherein the polypeptide is produced by a host cell selected from the group consisting of a bacterial cell, a yeast cell, an insect cell, and a mammalian cell.

6. The method of claim 1, wherein the subject is a human subject.

7. The method of claim 3, wherein the composition is administered by a route of administration selected from the group consisting of oral, nasal, intravenous, intraperitoneal, intramuscular, and subcutaneous.

8. The method of claim 3, further comprising the step of administering a compound selected from the group consisting of L-lysine, L-arginine, a flavine nucleoside, and a mixture thereof.

9. The method according to claim 3, wherein said cancer is selected from the group consisting of lung cancer, breast cancer, prostate cancer, colon cancer, cervix cancer, uterus cancer, larynx cancer, stomach cancer, liver cancer, Ewings sarcoma, acute lymphoid leukemia, chronic myeloid leukemia, apoptosis resistant leukemia, MDR lung cancer, pancreas cancer, gastric cancer, kidney cancer, gliomas, melanomas, chronic lymphoid leukemia, and lymphoma.

10. The method of claim 3, wherein the subject is a human subject.

11. The method of claim 1, wherein the cancer is selected from the group consisting of lung cancer and melanoma.

12. The method of claim 1, wherein the cancer is selected from the group consisting of leukemia and liver cancer.

* * * * *